US009572349B2

(12) United States Patent
Alquezar García et al.

(10) Patent No.: US 9,572,349 B2
(45) Date of Patent: *Feb. 21, 2017

(54) REPELLENT COMPOSITIONS AND GENETIC APPROACHES FOR CONTROLLING HUANGLONGBING

(71) Applicants: FUNDO DE DEFESA DA CITRICULTURA-FUNDECITRUS, Araraquara-SP (BR); INSTITUTO VALENCIANO DE INVESTIGACIONES AGRARIAS, Moncada, Valencia (ES)

(72) Inventors: Berta Alquezar García, La Eliana (ES); Ana Rodriguez Baixauli, Picanya (ES); Josep Peris Rodrigo, Alboraia (ES); Leandro Peña García, Náquera (ES); Andréia Henrique, Botucatu (BR); Marcelo Pedreira De Miranda, Araraquara (BR); Pedro Takao Yamamoto, Araraquara (BR); Marcel Bellato Spósito, Araraquara (BR); Nelson Arno Wulff, Araraquara (BR); Diva do Carmo Teixeira, Araraquara (BR); Antonio Juliano Ayres, Araraquara (BR); Newton Cavalcanti De Noronha, Jr., Piracicaba (BR); José Maurício Simões Bento, Piracicaba (BR); José Roberto Postali Parra, Piracicaba (BR)

(73) Assignees: Fundo de Defesa da Citricultura—Fundecitrus, Araraquara-SP (BR); Instituto Valenciano de Investigaciones Agrarias, Moncada, Valencia (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,376

(22) Filed: Jun. 8, 2015

(65) Prior Publication Data

US 2015/0353954 A1 Dec. 10, 2015

Related U.S. Application Data

(63) Continuation of application No. 13/501,739, filed as application No. PCT/BR2010/000353 on Oct. 26, 2010, now Pat. No. 9,078,448.

(60) Provisional application No. 61/255,705, filed on Oct. 28, 2009.

(51) Int. Cl.
| | | |
|---|---|---|
| *C12N 15/82* | (2006.01) | |
| *A01N 65/28* | (2009.01) | |
| *C12N 9/10* | (2006.01) | |
| *A01N 45/02* | (2006.01) | |
| *C12N 9/88* | (2006.01) | |
| *A01N 27/00* | (2006.01) | |
| *A01N 65/00* | (2009.01) | |

(52) U.S. Cl.
CPC ............. *A01N 65/28* (2013.01); *A01N 27/00* (2013.01); *A01N 45/02* (2013.01); *A01N 65/00* (2013.01); *C12N 9/1085* (2013.01); *C12N 9/88* (2013.01); *C12N 15/8243* (2013.01); *C12N 15/8281* (2013.01); *C12N 15/8286* (2013.01); *C12Y 205/01001* (2013.01); *C12Y 402/03057* (2013.01); *C12Y 402/03133* (2015.07)

(58) Field of Classification Search
None
See application file for complete search history.

(56) References Cited

U.S. PATENT DOCUMENTS

| | | | |
|---|---|---|---|
| 4,518,584 | A | 5/1985 | Mark et al. |
| 4,737,462 | A | 4/1988 | Mark et al. |
| 5,608,148 | A | 3/1997 | John |
| 5,650,161 | A | 7/1997 | Cannelongo |
| 5,981,834 | A | 11/1999 | John et al. |
| 5,981,842 | A | 11/1999 | Wu et al. |
| 5,990,387 | A | 11/1999 | Tomes et al. |
| 6,103,955 | A | 8/2000 | Peña Garcia et al. |
| 6,291,745 | B1 | 9/2001 | Meyer et al. |
| 6,524,811 | B1 | 2/2003 | Cunningham, Jr. et al. |
| 6,943,010 | B1 | 9/2005 | Dodo et al. |
| 7,273,735 | B2 | 9/2007 | Schalk et al. |
| 7,615,681 | B2 | 11/2009 | Georges et al. |
| 8,017,835 | B2 | 9/2011 | Chappell et al. |
| 8,071,840 | B2 | 12/2011 | Sanz Molinero |

(Continued)

FOREIGN PATENT DOCUMENTS

| | | |
|---|---|---|
| EP | 1 878 792 A1 | 1/2008 |
| EP | 2 184 351 A1 | 5/2010 |

(Continued)

OTHER PUBLICATIONS

Chen et al, 2003, The Plant cell, 15:481-494.*

(Continued)

*Primary Examiner* — Jason Deveau Rosen
(74) *Attorney, Agent, or Firm* — Winston & Strawn LLP

(57) ABSTRACT

The invention provides a method for controlling Huanglongbing (HLB) disease of citrus plants through expressing genes encoding synthases for sesquiterpenes such as β-caryophyllene, and α-copaene, and combinations thereof, in citrus plants. Methods of controlling HLB comprising applying at least one purified sesquiterpene, which repels *Diaphorina citri* and/or *Tryoza erytrae* psyllid insects, so as to control the HLB disease of citrus plants, are also disclosed.

10 Claims, 12 Drawing Sheets

(56) References Cited

U.S. PATENT DOCUMENTS

| | | | |
|---|---|---|---|
| 8,372,443 | B2 | 2/2013 | Rouseff et al. |
| 2006/0257441 | A1 | 11/2006 | Komai et al. |
| 2009/0123984 | A1 | 5/2009 | Chappell et al. |
| 2009/0313718 | A1* | 12/2009 | Degenhardt ............. C12N 9/88 800/265 |
| 2010/0009002 | A1* | 1/2010 | Simonetta .............. A01N 65/28 424/490 |
| 2010/0074972 | A1* | 3/2010 | Rouseff .................. A01N 27/00 424/712 |
| 2010/0166896 | A1 | 7/2010 | Zhang et al. |
| 2013/0266535 | A1 | 10/2013 | Stelinski et al. |

FOREIGN PATENT DOCUMENTS

| | | |
|---|---|---|
| JP | 2005-097165 A | 4/2005 |
| JP | 2005-145863 A | 6/2005 |
| WO | 00/22150 A9 | 4/2000 |
| WO | 00/55338 A1 | 9/2000 |
| WO | 03/055311 A1 | 10/2003 |
| WO | 2004/031376 A2 | 4/2004 |
| WO | 2006/111924 A2 | 10/2006 |
| WO | 2010/027783 A2 | 3/2010 |

OTHER PUBLICATIONS

Wu et al., "Redirection of cytosolic or plastidic isoprenoid precursors elevates terpene production in plants," Nature Biotechnology, 24(11): 1441-1447 (Nov. 2006).
Yan et al., "Advances of studies on the effects of plant volatiles on insect behavior," Chinese Journal of Applied Ecology, 14(2): 310-313 (Feb. 2003) (English abstract).
Yang et al., "Chrysanthemum expressing a linalool synthase gene 'smell good', but 'tastes bad' to western flower thrips," Plant Biotechnology Journal, 11(7): 875-882 (Sep. 2013).
Yu et al., "Molecular cloning and functional characterization of α-humulene synthase, a possible key enzyme of zerumbone biosynthesis in shampoo ginger (*Zingiber zerumbet* Smith)," Planta, 227: 1291-1299 (2008).
International Search Report, Appl. No. PCT/BR2010/000353, Feb. 8, 2011.
U.S. Appl. No. 13/501,739, Non-Final Office Action, Nov. 5, 2013.
U.S. Appl. No. 13/501,739, Final Office Action, Feb. 11, 2014.
U.S. Appl. No. 13/501,739, Advisory Action, Apr. 10, 2014.
U.S. Appl. No. 13/501,739, Non-Final Office Action, Jul. 10, 2014.
U.S. Appl. No. 13/501,739, Final Office Action, Nov. 21, 2014.
U.S. Appl. No. 13/501,739, Advisory Action, Feb. 6, 2015.
U.S. Appl. No. 13/501,739, Notice of Allowance, Mar. 13, 2015.
Aharoni et al., "Terpenoid Metabolism in Wild-Type and Transgenic Arabidopsis Plants," The Plant Cell, 15: 2866-2884 (Dec. 2003).
Altschul et al., "Basic Local Alignment Search Tool," J. Mol. Biol., 215: 403-410 (1990).
Altschul et al., "Amino Acid Substitution Matrices from an Information Theoretic Perspective," J. Mol. Biol., 219: 555-565 (1991).
Bauer et al., "A genetic enrichment for mutations constructed by oligodeoxynucleotide-directed mutagenesis," Gene, 37: 73-81 (1985).
Bohlmann et al., "Plant terpenoid synthases: Molecular biology and phylogenetic analysis," Proc. Natl. Acad. Sci. USA, 95: 4126-4133 (Apr. 1998).
Cai et al., "A cDNA clone for β-caryophyllene synthase from Artemisia annua," Phytochemistry, 61: 523-529 (2002).
Chen et al., "Biosynthesis and Emission of Terpenoid Volatiles from Arabidopsis Flowers," The Plant Cell, 15: 481-494 (Feb. 2003).
Chen et al., "Characterization of Volatiles in Guava (*Psidium guajava* L. cv. Chung-Shan-Yeuh-Pa) Fruit from Taiwan," Journal of Food and Drug Analysis, 14(4): 398-402 (2006).
Chen et al., "The family of terpene synthases in plants: a mid-size family of genes for specialized metabolism that is highly diversified throughout the kingdom," The Plant Journal, 66: 212-229 (2011).

Cheng et al., "Plant Terpenoids: Biosynthesis and Ecological Functions," Journal of Integrative Plant Biology, 49(2): 179-186 (2007).
Cheng et al., "The rice (E)-β-caryophyllene synthase (OsTPS3) accounts for the major inducible volatile sesquiterpenes," Phytochemistry, 68: 1632-1641 (2007).
Corey et al., "Total Synthesis of d,l-Caryophyllene and d,l-lsocaryophyllene," J. Am. Chem. Soc., 86: 485-492 (1964).
Craik, "Use of Oligonucleotides for Site-Specific Mutagenesis," BioTechniques, 3(1): 12-19 (Jan./Feb. 1985).
Cunillera et al., "Arabidopsis thaliana Contains Two Differentially Expressed Farnesyl-Diphosphate Synthase Genes," The Journal of Biological Chemistry, 271(13): 7774-7780 (Mar. 1996).
Degenhardt et al., "Restoring a maize root signal that attracts insect-killing nematodes to control a major pest," PNAS, 106(32): 13213-13218.
Degenhardt et al., "Monoterpene and sesquiterpene synthases and the origin of terpene skeletal diversity in plants," Photochemistry, 70(15-16): 1621-1637 (Oct.-Nov. 2009).
Dudareva et al., "Biosynthesis, function and metabolic engineering of plant volatile organic compounds," New Phytologist, 198: 16-32 (2013).
Dudareva et al., "Plant Volatiles: Recent Advances and Future Perspectives," Critical Reviews in Plant Sciences, 25: 417-440 (2006).
Huang et al., "The major volatile organic compound emitted from *Arabidopsis thaliana* flowers, the sesquiterpene (E)-β-caryophyllene, is a defense against a bacterial pathogen," New Phytologist, 193: 997-1008 (2012).
Jacobson et al., "Optical Isomers of α-Copaene Derived from Several Plant Sources," J. Agric. Food Chem., 35: 798-800 (1987).
Jez et al., "Dissection of Malonyl-Coenzyme A Decarboxylation from Polyketide Formation in the Reaction Mechanism of a Plant Polyketide Synthase," Biochemistry, 39: 890-902 (2000).
Kappers et al., "Genetic Engineering of Terpenoid Metabolism Attracts Bodyguards to Arabidopsis," Science, 309: 2070-2072 (Sep. 2005).
Kessler et al., "Field Experiments with Transformed Plants Reveal the Sense of Floral Scents," Science, 321: 1200-1202 (2008).
Keszei et al., "Functional end evolutionary relationships between terpene synthases from Australian Myrtaceae," Phytochemistry, 71: 844-852 (2010).
Köllner et al., "A Maize (E)-β-Caryophyllene Synthase Implicated in Indirect Defense Responses against Herbivores is not Expressed in Most American Maize Varieties," The Plant Cell, 20: 482-494 (Feb. 2008).
Kunkel, "Rapid and efficient site-specific mutagenesis without phenotypic selection," Proc. Nat. Acad. Sci. USA, 82: 488-492 (Jan. 1985).
Kunkel, "Rapid and Efficient Site-Specific Mutagenesis without Phenotyic Selection," Methods in Enzymology, 154: 367-382.
Lavy et al., "Linalool and linalool oxide production in transgenic carnation flowers expressing the Clarkia breweri linalool synthase gene," Molecular Breeding, 9: 103-111 (2002).
Lücker et al., "Expression of Clarkia S-linalool synthase in transgenic petunia plants results in the accumulation of S-linalyl-β-D-glucopyranoside," The Plant Journal, 27(4): 315-324 (2001).
Lücker et al., "Increased and Altered Fragrance of Tobacco Plants after Metabolic Engineering Using Three Monoterpene Synthases from Lemon," Plant Physiology, 134: 510-519 (Jan. 2004).
Mahmoud et al., "Metabolic engineering of essential oil yield and composition in mint by altering expression of deoxyxylulose phosphate reductoisomerase and menthofuran synthase," PNAS, 98(15): 8915-8920 (Jul. 2001).
Mann et al., "Induced Release of a Plant-Defense Volatile 'Deceptively' Attracts Insect Vectors to Plants Infected with a Bacterial Pathogen," PLoS Pathogens, 8(3): e1002610-1-e1002610-13 (Mar. 2012).
Mann et al., "Repellency and toxicity of plant-based essential oils and their constituents against Diaphorina citri Kuwayama (Hemiptera: Psyllidae)," Journal of Applied Entomology, 136(1-2): 87-96 (Feb. 2012).

(56) References Cited

OTHER PUBLICATIONS

Mercke et al., "Combined Transcript and Metabolite Analysis Reveals Genes Involved in Spider Mite Induced Volatile Formation in Cucumber Plants," Plant Physiology, 135: 2012-2024 (Aug. 2004).
Mockutë et al., "Volatile constituents of cultivated *Organum volgare* L. inflorescences and leaves," Chemija, 15(1): 33-37 (2004).
Nishida et al., "α-Copaene, a Potential Rendezvous Cue for the Mediterranean Fruit Fly, *Ceratitis capitata*?," Journal of Chemical Ecology, 26(1): 87-100 (2000).
Ohara et al., "Monoterpene engineering in a woody plant *Eucalyptus camaldulensis* using a limonene synthase cDNA," Plant Biotechnology Journal, 8: 28-37 (2010).
Quispe-Condori et al., "Obtaining β-caryophyllene from Cordia verbenacea de Candolle by supercritical fluid extraction," The Journal of Supercritical Fluids, 46: 27-32 (2008).
Raal et al., "Comparacion de aceites esenciales de *Matricaria recutita* L. de origen diverso," Ars Pharmaceutica, 44(2): 159-165 (2003).
Rodríguez et al., "Terpene Down-Regulation in Orange Reveals the Role of Fruit Aromas in Mediating Interactions with Insect Herbivores and Pathogens," Plant Physiology, 156: 793-802 (Jun. 2011).
Rouseff et al., "Sulfur Volatiles in Guava (*Psidium guajava* L.) Leaves: Possible Defense Mechanism," J. Agric. Food Chem., 56: 8905-8910 (2008).
Schnee et al., "The products of a single maize sesquiterpene synthase form a volatile defense signal that attracts natural enemies of maize herbivores," PNAS, 103(4): 1129-1134 (Jan. 2006).
Shelly et al., "Exposure to α-Copaene and α-Copaene-Containing Oils Enhances Mating Success of Male Mediterranean Fruit Flies (*Diptera*: *Tephritidae*)," Annals of the Entomological Society of America, 94(3): 497-502 (2001).
Tholl et al., "Two sesquiterpene synthases are responsible for the complex mixture of sesquiterpenes emitted from Arabidopsis flowers," The Plant Journal, 42: 757-771 (2005).
Verma et al., "Essential oil composition of Lavandula angustifolia Mill. cultivated in the med hills of Uttarakhand, India," J. Serb. Chem. Soc., 75(3): 343-348 (2010).
Walder et al., "Oligodeoxynucleotide-directed mutagenesis using the yeast transformation system," Gene, 42: 133-139 (1986).
Wang et al., "Cloning, expression and wounding induction of β-caryophyllene synthase gene from Mikania micrantha H.B.K. and allelopathic potential of β-caryophyllene," Allelopathy Journal, 24(1): 35-44 (2009).
Alma et al., "Chemical Composition and Content of Essential Oil from the Bud of Cultivated Turkish Clove (*Syzygium aromaticum* L.)," BioResources, 2(2):265-269 (2007).
Beattie et al., "Aspects and Insights of Australia-Asia Collaborative Research on Huanglongbing," Multilateral Research Network for Food and Agricultural Safety, The International Workshop for Prevention of Citrus Greening Disease in Severely Infested Areas. Tropical Agriculture Research Front (TARF), Japan International Research Center for Agricultural Sciences (JIRCAS), Ishigaki, Japan, pp. 47-64, Dec. 6-7, 2006.
Hashinaga et al., "Production of Volatile Components of Guava during Maturation," Bull. Fac. Agric., Kagoshima Univ., 37:59-64 (1987).
Mayer et al., "Phytopathogen Lures Its Insect Vector by Altering Host Plant Odor," Journal of Chemical Ecology, 34:1045-1049 (2008).
Silva et al., "Repellency of selected Psidium guajava cultivars to the Asian citrus psyllid, *Diaphorina citri*," Crop Protection, 84:14-20 (2016).
Communication under Rule 71(3) EPC, Application No. EP 10825870.8, Jul. 4, 2016.

* cited by examiner

SEQ ID NO:1

| | | | | | |
|---|---|---|---|---|---|
| 1 | ATGTCCGCTC | AAGTTCTAGC | AACGGTTTCC | AGTTCAACAG | AAAAAACTGT | TCGTCCCATT |
| 61 | GCTGGTTTCC | ATCCTAACTT | ATGGGGAGAC | TATTTCCTGA | CCCTCGCTTC | TGATTGCAAG |
| 121 | ACAAATGATA | CTACGCACCA | AGAGGAATAC | GAAGCGCTGA | AGCAAGAAGT | CAGAAGCATG |
| 181 | ATAACGGCTA | CGGCAGATAC | ACCTGCCCAG | AAGTTGCAAT | TGGTTGATGC | AGTCCAACGA |
| 241 | TTGGGTGTGG | CCTATCACTT | CGAACAGGAG | ATAGAAGATG | CAATGGAAAA | GATTTATCAC |
| 301 | GATGACTTTG | ATAATAACGA | TGATGTCGAT | CTCTACACTG | TTTCTCTTCG | TTTTCGACTG |
| 361 | CTTAGGCAGC | AAGGATTTAA | GGTTCCGTGT | GATGTGTTCG | CGAAGTTCAA | AGATGATGAA |
| 421 | GGTAAATTCA | AGGCATCATT | GGTGCAGGAT | GTTCATGGCA | TTCTAAGTTT | GTATGAGGCA |
| 481 | GGACACTTGG | CCATTCGCGG | AGAAGGGATA | TTAGATGAAG | CCATTGCTTT | CACTAGAACT |
| 541 | CACCTTCAGT | CAATGGTATC | TCAGGATGTA | TGCCCTAATA | ATCTTGCTGA | ACAAATTAAT |
| 601 | CATACTCTCG | ACTGTCCTCT | CCGCAGAGCC | CTTCCAAGAG | TGGAGACAAG | ATTTTCTTG |
| 661 | TCTGTCTATC | CAAGAGATGA | TAAACACGAT | AAAACTTTGT | TAAAGTTTTC | AAAGTTAGAC |
| 721 | TTTAACCATG | TGCAAAGAAT | ACATCAGAAG | GAATTAAGTG | CCATCACACG | GTGGTGGAAA |
| 781 | GATTAGACT | TCACTACAAA | GCTACCTTAT | GCAAGAGACA | GAATCGTAGA | GTTGTATTTT |
| 841 | TGGATTGTAG | GGACGTATTT | TGAACCAAAG | TACACTTTAG | CGAGAAAAAT | AATGACCAAA |
| 901 | ACAATTTACA | CGGCATCTAT | CATAGATGAC | ACTTTCGACG | CTTATGGTTT | CTTTGAAGAG |
| 961 | CTCAAACTCT | TAGCAGAAGC | AGTCCAGAGG | TGGGACATTG | GAGCCATGGA | TATACTTCCA |
| 1021 | GAATACATGA | AAGTGCTTTA | TAAGGCCCTT | TTAGATACTT | TCAATGAAAT | TGAGCAAGAC |
| 1081 | TTGGCCAAGG | AAGGAAGATC | GTCCTGCTTA | CCTTATGGCA | AGAAAAAGAT | GCAAGAGCTT |
| 1141 | GTTCAAATGT | ACTTTGTTCA | AGCCAAGTGG | TTCAGTGAAG | GTTATGTTCC | GACATGGGAC |
| 1201 | GAATATTATC | CGGTTGGACT | TGTAAGTTGC | GGCTACTTCA | TGCTTGCGAC | AAATTCCTTC |
| 1261 | CTTGGCATGT | GTGATGTTGC | AAACAAGGAA | GCTTTTGAAT | GGATATCCAA | GGACCCTAAG |
| 1321 | ATTTCAACAG | CGTCATCAGT | TATCTGCAGA | CTTAGGAATG | ACATTGTTTC | CCACCAGTTT |
| 1381 | GAACAGAAGA | GAGGACATAT | TGCCTCAGGA | GTTGAATGCT | ACATTAAGCA | GTATGGTGTT |
| 1441 | TCAGCAGAAG | AGGTAGTTAC | AGTTTTTACT | GAAGAAGTTG | AGAATGCATG | GAAAGATATG |
| 1501 | AATGAGGAAT | TCCTGAAACC | AACTGCTTTT | CCTGTGGCTT | TGATTGAGAG | ACCTTTCAAT |
| 1561 | ATCGCACGTG | TGATTGAATT | TCTAAACAAG | AAGGGTGATT | GGTACACTCA | TTCTCATGCG |
| 1621 | ATTAAAGACC | AGATTGCCGC | AGTGCTCAGA | GACCCTGTTA | CCATCTGA | |

SEQ ID NO:2

| | | | | | |
|---|---|---|---|---|---|
| 1 | MSAQVLATVS | SSTEKTVRPI | AGFHPNLWGD | YFLTLASDCK | TNDTTHQEEY | EALKQEVRSM |
| 61 | ITATADTPAQ | KLQLVDAVQR | LGVAYHFEQE | IEDAMEKIYH | DDFDNNDDVD | LYTVSLRFRL |
| 121 | LRQQGFKVPC | DVFAKFKDDE | GKFKASLVQD | VHGILSLYEA | GHLAIRGEGI | LDEAIAFTRT |
| 181 | HLQSMVSQDV | CPNNLAEQIN | HTLDCPLRRA | LPRVETRFFL | SVYPRDDKHD | KTLLKFSKLD |
| 241 | FNHVQRIHQK | ELSAITRWWK | DLDFTTKLPY | ARDRIVELYF | WIVGTYFEPK | YTLARKIMTK |
| 301 | TIYTASIIDD | TFDAYGFFEE | LKLLAEAVQR | WDIGAMDILP | EYMKVLYKAL | LDTFNEIEQD |
| 361 | LAKEGRSSCL | PYGKEKMQEL | VQMYFVQAKW | FSEGYVPTWD | EYYPVGLVSC | GYFMLATNSF |
| 421 | LGMCDVANKE | AFEWISKDPK | ISTASSVICR | LRNDIVSHQF | EQKRGHIASG | VECYIKQYGV |
| 481 | SAEEVVTVFT | EEVENAWKDM | NEEFLKPTAF | PVALIERPFN | IARVIEFLNK | KGDWYTHSHA |
| 541 | IKDQIAAVLR | DPVTI | | | | |

FIG. 1A

SEQ ID NO:3

```
1     ATGAGGGATG TTAAGAGTGT TCTTTCTTCA AAAGAAAGCA CGAAAGCCGA TGTGAACCGT
61    CGATCCTCGA ATTATCATCC TAGCATTTGG GGTGATCATT TCATTAATGT GTCATCAAAT
121   GAAAAGTACA CCAATACGGA AGTCGAAAAG CGGTTTGAAA CATTAAAAGC AGAAATTGAA
181   AAGTTGCTGG TGAGCAATAA TACAGCATGG AAAACACTTG AAGAAATTGT GGCTATTGTT
241   AATCAACTTC AACGCCTTGG TGTGGCCTAT CATTTTGAAA ATGAGATCAA AGAGGCCTTA
301   CAAACAATCT ATGATAGCCA TGTTAACGGC AATTGTGATG TTAATTACGA TCATAATAAC
361   GATCTCTACA TAGTTGCTCT TCGATTTCGG CTTCTAAGGC AGCATGGTTA CAAGGTGTCA
421   GCAGATATAT TTAAAAAATT CAGAGATGAA AAAGGTGAAT TCAAGGCCAT GTTAACAAAT
481   GACGCGAAAG GCTTGCTATG TTTGTATGAG GCGTCATATC TGAGAGTACA AGGGGAGAAT
541   ATATTGGAAG AAGCATGTGA ATTTTCTAGG AAGCACTTAA AATCTTTATT GTCCCATTTA
601   AGCACTCCTC TAGCTGACCA AGTTGAGCAC TCCCTGGAGA TACCTTTGCA CAGAGGGATG
661   CCAAGATTGG AGGCAAGGCA GTATATTTCC ATCTATGAAG CAGACAATTC AACACGAAAT
721   GAGCTAATAT TAGAACTTGC AAAGCTAGAT TTAATCTTT  TGCAGGCGTT ACACCGGATA
781   GAGCTAAGTG AGATCTCAAG GTGGTGGAAA GATATTGATT TTGCAACAAA GCTACCTTTT
841   GCAAGAGATA GAGTGGTGGA GGGCTATTTC TGGATTTTGG GAGTATATTT TGAGCCAAAA
901   TTTTTATTGG CTAGAAAAAT TCTAACCAAA GTGATATCAA TGGCTTCAAT TATTGATGAC
961   ATTTATGATG CTTATGGTAC AATAGAAGAA CTTGAGCTTT TTGCCACAGC AATTGAGAGG
1021  TGGGATCTCA GTGCCATAGA TCTGCTTCCT GAGTACATGA AGTTGTGCTA TTGCGCTCTC
1081  CTGGATGCTT ACAGCGAATT TGAGAAAGAT TTGGCCAGCA AAGGAATATT GTACGGCCTA
1141  CCTTTTGCTA AAGAATCGAT GAAGATTTTG GTGAGAAGTT ACATCATCGA AGCTAGATGG
1201  TGTGACCAAC AATATGTACC GACAATGGAG GAATACATGC GCGTTGCACT ACTTTCATGT
1261  GGCTACTTAC TGTTATCAAC ATCTTCATTT CTGGGAATGG AAGATATTGT AACAAAAGAA
1321  GCCTTTGAAT GGGTATCCGG CAACCCTAAA ATCGTTCAGG CTTCCTCAAT AATTTGCAGA
1381  CTCATGGATG ACATTGTCTC TCATAAGTTT GAGCAACAGA GAGGACATGT GGCCTCAGCT
1441  GTTGAATGCT ACATGAAGCA GCATGGAGTT TCTGAGGAAG AGGCAGTTAA AGTGTTTCGG
1501  GAGAAAGTTG GGAATGCGTG GAAAGATATA AATGAGGAGC TCATGAGACC ACCTGTTGTT
1561  CCTATGCCTT TGCTCGAACG GGTTCTTAAT CTTGCTCGTT TAATGGATGT GCTGTACCAA
1621  AATAATGATT CCTATACAAA TCCTCACTTG ATGAAAGATC ATGTAGCCGC ATTGCTTAAG
1681  GATCCTGTTT TCTTTGAAGA CTAG
```

SEQ ID NO:4

```
1     MRDVKSVLSS KESTKADVNR RSSNYHPSIW GDHFINVSSN EKYTNTEVEK RFETLKAEIE
61    KLLVSNNTAW KTLEEIVAIV NQLQRLGVAY HFENEIKEAL QTIYDSHVNG NCDVNYDHNN
121   DLYIVALRFR LLRQHGYKVS ADIFKKFRDE KGEFKAMLTN DAKGLLCLYE ASYLRVQGEN
181   ILEEACEFSR KHLKSLLSHL STPLADQVEH SLEIPLHRGM PRLEARQYIS IYEADNSTRN
241   ELILELAKLD FNLLQALHRI ELSEISRWWK DIDFATKLPF ARDRVVEGYF WILGVYFEPK
301   FLLARKILTK VISMASIIDD IYDAYGTIEE LELFATAIER WDLSAIDLLP EYMKLCYCAL
361   LDAYSEFEKD LASKGILYGL PFAKESMKIL VRSYIIEARW CDQQYVPTME EYMRVALLSC
421   GYLLLSTSSF LGMEDIVTKE AFEWVSGNPK IVQASSIICR LMDDIVSHKF EQQRGHVASA
481   VECYMKQHGV SEEEAVKVFR EKVGNAWKDI NEELMRPPVV PMPLLERVLN LARLMDVLYQ
541   NNDSYTNPHL MKDHVAALLK DPVFFED
```

FIG. 1B

```
AAL79181  .SKLLIDMSVKEEKVIRPIVHFPPSVWADQFLIFDDKQAEQANVEQVVNELREDVRKDLVSSLDVQTEHTNLLKLIDA.......    77
ACN67535  FQLSIHLSMGCKQESFRFFRSTSPSVWGDMFLNYEKK.AEQCDVELTVEDLKEKVREATTGALGNPKEHVNLLKLIDA.......    77
AAU05952  ...............KVMSSHFPASIMKTNDIYDTKRSLANFHPTIWKEHFLSFTFDDALKVDGGMKERIEKLKEEIRMMVIASV    70
AAO85539  ........................MGSEVNRPLADFPANIWEDPLTSESKSDLGTETFKERHST...LKEAVKEAFMSS         52
ABY79206  ................MAADEARSVSRLHSEEDMHGKHHSTLNGDFFLHHVPCRPGQYLTMKDNVEIMKEEV.KKMLLDVG       64
ABJ16553  ....MATSVPSVLLLPVPTCTDMLVSPVEGGDLLHCKPHFDHHPNVWGDYFLTFSPCTPSMLLNMKRKAHVS.EEQ.VRRMILEC   79

AAL79181  ..............IQRLGIAYHFEEEIEQALCHIYDTYGDWKGRSPSLW..............BRLRCCCFYVSCLIEKN.     132
ACN67535  ..............IQRLGIPYYFEEEITNALCHLYEAYGEWVGGSPSIW..............BRLRCCCFYVSCLINKY      133
AAU05952  QNPLVK..LNLVDSIQRLGVSYHEEEEIDQFLEEMYVSYNNSLLFSSNDSQDD.....DLHISALLRLLSCHCYRTSCDLELK.   147
AAO85539  KANPIE..NIKFIDALCRLGVSCHFEKDIVEQLDKSFDCLPFPQMVRQEGC.......DLYTVGITRQVLRQFCKLSADVLEKF   128
ABY79206  SSDLSH..KLDCIDTLERLGLDYHYTKEIDELMCNVFEARCQDL.............DLTITTSQLRYLLRKHCYHLSDVRLKF   133
ABJ16553  SSGPNLHVKLELVLDTLERLCIDYHYFKEIENVLRRVHEERDDTDNHY..........DLHTTALRYLLRKHCYASLDVEQRF   153

AAL79181  YKKEDGSFKESLTNDVEGLLELYEALYLRVQGEGVLDDALVFTRTCLEKIAKDLVHTNPTLSTYIQEALKQFLHKRLTRLEALRY   217
ACN67535  YKDKHGDFKESLINDDEEMVELYEAUSLRVRGEVVLDEAFEFTRNHFANLAKEPRCSNATLSTHIQVALETPLHKRIPRLDALRY   218
AAU05952  FMDNNGKFKESLVEDERGILSLYEASIMRGHGEALLEFALEFTTTHLKAYIHLYSNINPNFASEVSNALKLPI..RKCVPRVKAR   230
AAO85539  KDENGKFKGHLVTDAYGMLSLYEAQWGTHGEDIIDEALAFSRSHLEEISSRSSPH......LAIRIKNALKHPYHKGISRIETR   207
ABY79206  REDKGDIVTNDARCLLRMYE....AAHVRVNGEEILDNILIHTKRQLQCTVDDLEPTLQEEVRY.....ALETPLFRRINRVQAR   209
ABJ16553  RDEEGNFTRDDNNNGTRSMLSLYNAAHIRIHGEEILDDAIVFTRNYLQSVVKHLQSPMADEVCS.....ALRTPLFRRPRKVEAR   233

AAL79181  IPMYEQQASHNESLLKIAKLGFNLLQSLHRKELSEVSRWWKGLDVPNNLPYARDRMVECYFWALGVYFEPKYSQARIFLAKVISL   302
ACN67535  IRFYEKQASHNESLLKIAKLGFNLLQSLHRSELSQVSKWWKDVDVQKNLPYARDRMVESYFWAIGVYSEPKYSLGRVFLAKVIQL   303
AAU05952  EYFEIYQQQPSHNETLITFSKLDFNILQKLHQKEIABICRWWKDLNVSTNFPFARDRIVECYFWILSIYF..EPYFKFGRKILTK   313
AAO85539  QYISYEEEESCDP..TLLEFAKLEFNLQILHREELACVTRWHHEMEFKSKVTYTRHRITEAYLWSLGTYFEPQYSQARVITTM   290
ABY79206  QFISTYEKSTTRINMLEE..FSKLDFNILLTLYCEELKDLTLWWKEFQAQANTTIYARDRMVEMHFWMMGVFFEPQYSYSRKMLT   292
ABJ16553  HYISVYDKLPTRNETTLE..FAKLDFGILQSLYCEELNILMWKELQLQDHLSF.ARDRMVEMHFWMLGVLFEPQYSYGRIMLT   315

AAL79181  ATVLDDTYDAYGTYEELKIFTEAIQRWSITCIDMLPEYLKLL..YQGVLDTYIEMEEINGKEFGKAHHLSYAKESMKFPIRSYMME   385
ACN67535  ATAIDDTFDAYGTYEELQTFTRAVERWSITCILEIPEYMKLL..YQVLLDLYGEMEPIMEKEQLTPLFNCSKEFMIETVKAYMVE   386
AAU05952  VIAMTSIMEDIYDAYGTFEELQLFTLAIKRWDMSMVNLLPQY..MKVHYTTLLLLFERMDKGIVNDGISYRSCFGKEAMKRQAES   396
AAO85539  ALILFTALLDMYDAYGIMEELELFTDAVDEWLPVVFDEIPIPDSMKFIYNVTVEFYDKLDEELEKEGRSGCGFHLKKSLQKTANG   375
ABY79206  QLFMIVSVLDDLYDSHCTTEEGNAFTAALQRWLEEGVEQCPTYLRTLYTNIRATIKAIEEDLNFQNNKHAKLVKGLIIDMAMCYN   377
ABJ16553  KLFIFVSIFDDIYDNYSTLEESKLFTEAIERWDEEAAEELPGYMKFFYKKVLTTMKSIETDLKLQGNKHVDYVKNLLIDATRCFY   400

AAL79181  AKWANEGYVPTAEEHMSVAFVSSGY....SMLATTCFVGMGDIVTDFAFKWALTKPPIIKASCAIARLMDDIHSQKEEKFRIHVA   466
ACN67535  AKWVYEGHIPTKDEHTSIAFATGGG....PLLMSSCYLGMGDILTNDSINWVISEPPLLKATNMIGRLLNDIVSSKKEQERVHFQ   467
AAU05952  YFKEAEWLNKNYKPKYGEYMEVALA....SSGYELLSTISFVCMGE.IATKEVFEWLFDCPQILKASTTISRLMDDVVSYKFEKE   476
AAO85539  YMQEAKWLKKDYIATFDEYKENAIL....SSGYYGLIAMTFVRMILVAKLDAFEWLNSHEKIRVASEIISRFTDLISSYEFEIIKR   456
ABY79206  AET..LWRDKKYVP..ATVDEHLKISARSSGCMHLVSQGFISMG.IVATSEALEWASTYFKIVRAVCIIARLANDIMSYKREASN   457
ABJ16553  NEV..KWRSEGADQVAATVEEHLKISVPSSCCMHVPVYAFVAMGNIVTIDDAINWGMAYFKIITSSCIVGRLLNCIASHEREQGS   483

AAL79181  SSVESYMKCYDVTEEHVL.KVFNKKIEDAWKDITRESLVRKDIEMPLMMRVINIAQVMDVLYKHKDGFTNVGE.ELKDHIKSLIV   549
ACN67535  SIVQCYKKCYDVSEEHAI.NLVREEIEDVWKDINKDSLTAKDVPRPLILVVVNYARTLYYLYKYNDNFPEVEE.DIKEDIKSLLI   550
AAU05952  REHIVSAVECYMSNHGRS.EDETCAELLKQVEDAWKTINECCLHPMNVPMPFLICLLNLTRVMALLYSHEDGY.TNSKGRTKLL   559
AAO85539  EHVATGIDCYMQQFGVSK.ERAVEVMGNIVSDAWKDLNQELMRPHVFPF..PLIMRVLNLSRVIDVFYRYQDA.YTNPKLLKEHI   537
ABY79206  NIMV.STVQTCAKEYGTTTVEQAIEKIRELIEEAWMCITHECLRCP..QPKALLERAVNLARTMDFLYKDADGYTDSRSIKGILD   539
ABJ16553  SSSSSSTVEACMREHGGITKEEAYAKLRELVEESWMDIAGECIRFAAAQPPPLLEAVVNATRVLDFVYKDDQDAYTHPSSLKDTI   568

AAL79181  HPIPL.....                                                                            554
ACN67535  HPMSI.....                                                                            555
AAU05952  QSLLIDPLHL                                                                            569
AAO85539  VSLLIETIPI                                                                            547
ABY79206  SLYVHLID..                                                                            547
ABJ16553  HSIYILSV..                                                                            576
```

| | | |
|---|---|---|
| AAL79181 | .SKLLIDMSVKEEKVIRPIVHFPPSVWADQFLIFDDKQAEQANVEQVVNEIREDVRKELVSSLDVQTEHTNLLKLIDA....... | 77 |
| ACN67535 | FQLSIHLSMGCKQESFRPFRSTSPSVWGDMFLNYERK.AEQCDVELTVEDLKEKVREAITGALGNPKEHVNLLKLIDA...... | 77 |
| AAU05952 | ............KVMSSHFPASIMKTNDIYDTKRSLANFHPTIWKEHPLSFTFDDALKVLGGMKERIEKLKEEIRMMVIASV | 70 |
| AAO85539 | ............................MGSEVNRPLADFPANIWEDPLTSFSKSELGTETFFKEKHST...LKEAVKEAFMSS | 52 |

| | | |
|---|---|---|
| AAL79181 | ...............IQRLGIAVHFEETIEQALQHIYDTYGDWKGRSPSLW..............ERLIRCCGFYVSCDIEKN. | 132 |
| ACN67535 | ...............IQRLGIPYYFEDTLTNALQHLMEAYGDEWVGGSPSIW..............ERLLRCHGIYVSCDIENKY | 133 |
| AAU05952 | QNPLVK..LNLVDSIQRLGVSYHFEEDEIDQFLEHMYVSYNNSLLFSSNDSQDD.....DLHISALLERLLRQHGYRIESCDIBLK. | 147 |
| AAO85539 | KANPIE...NIKFIDALCRLGVSCHFEKDIVEQLDKSFDCLDFPQMVRQEGC.......DLYTVGIIEQVERQFCKKLSADVEFKF | 128 |

| | | |
|---|---|---|
| AAL79181 | YKKEDGSFKESITNDVEGLLELYEATYLHVQGEGVLDLALVTRTCLEKIAKDLVHTNPTLSTYIQEALKDLHKKLTRLEALRY | 217 |
| ACN67535 | YKDKIGDFKESLINDDEEMVELYEATSLIVRGEVVLDEAFEETRNHFANIAKEFRCSNATLSTHIQVALETPLHKRIPRLDALRY | 218 |
| AAU05952 | FMDNNGKFKESIVEDERGIILSLYEASHMRGHGEALLEEALEFITTHLKAYIHLYSNINPNFASEVSNALKLPI..RKCVPRVKAR | 230 |
| AAO85539 | KDENGKFKGHLVTDAYGMLSLYEAAQWGTHGEDIIDEALAFSRSHLEEISSSRSSPH......LAIRIKNALKHPYHKGISRIETR | 207 |

| | | |
|---|---|---|
| AAL79181 | IPMYEQQASHNESLLKLAKLGFNLLQSLHRKELSEVSRWWKGLCVPNNLPYARDRMVECYFWALGVYFEEKYSQARIELAKVISL | 302 |
| ACN67535 | IREYEKQASHNESLLKLAKLGFNLLQSLHRSELSQVSKWWKDVDVQKNLPYARDRMVESYFWAIGVYSEEKYSLGRVELAKVIQL | 303 |
| AAU05952 | EYFEIYQQQFSHNETLETFSKLDFNILQKLHQKIAEICRWWKELNVSTNFPFARDRIVECYFWILSIYF..EPYFKEGRKILTK | 313 |
| AAO85539 | QYISYYEEESCDP..TLLEFAKIDFNELQILHREELACVTRWHHEMEFKSKVTYTRHRITEAYLWSLGTYFEPQYSQARVITTM | 290 |

| | | |
|---|---|---|
| AAL79181 | ATVLDDTYDAYGTYEELKIFTEAIQRWSITCIDMLPEYLKLL..YQGVLDIYIEMEEIMGKEGKAHHLSYAKESMKEFIRSYMME | 385 |
| ACN67535 | ATAIDDTFDAYGTYEELQTFTRAVERWSITCLDELEEYMKLL..YQVLLDLYGEMEPIMEKEQLTPLFNCSKEFMIEIVKAYMVE | 386 |
| AAU05952 | VIAMTSIMDDIYDAYGTFEEIQLFTIAIKRWDMSMVNLLPQY..MKVHYTTLLDLFEEMDKGIVNDGISYRSCFGKEAMKRQAES | 396 |
| AAO85539 | ALILFTALDDMYDAYGTMEELELFTDAMDEWLPVVEDEIPIPDSMKFIYNVIVEFYDKLDEELEKEGRSGCGFHLKKSLQKTANG | 375 |

| | | |
|---|---|---|
| AAL79181 | AKWANEGYVPTAEEHMSVAFVSSGY....SMLATTCFVGMGDIVIFDEAFKWALTKPPIIKASCAIARLMDDIHSQKEEKERIHVA | 466 |
| ACN67535 | AKWVYEGHIPTKDEHTSIAFATGGG....PLLMSSCYLGMGDIIINDSINWVISEPPLLKATNMIGRLLNDIVSSKKEQERVIFQ | 467 |
| AAU05952 | YFKEAKWLNKNYKPKYGEYMEVALA....SSGYELLSTISFVCMGD.IATKEVFEWLFDCPQILKASTTISRLMDDVVSYKFEKE | 476 |
| AAO85539 | YMQEAKWLKKDYIATFDEYKENAIL....SSGYYGLIAMTFVRMTDVAKLDAFEWLNSHPKIRVASEIISRFTDDISSYEFEHKR | 456 |

| | | |
|---|---|---|
| AAL79181 | SSVESYMKQYDVTEEHVL..KVFNKKIEDAWKDITRESLVRKDIPMPIMMRVINLAQVMDVLYKHKDGFINVGE..ELKDHIKSLLV | 549 |
| ACN67535 | SIVQCYKKQYDVSEEHAI..NLVREEIEDVWKDINKCSLTAKDVPRPLILVVVNYARTLYYLYKYNDNFFEVEE.DIKEDIKSLLI | 550 |
| AAU05952 | REHIVSAVECYMSNHGRS..EDETCAELLKQVEDAWKTINECCLHPMNVPMPFLICLLNLTRVMALLYSHEDGY.TNSKGRTKLLI | 559 |
| AAO85539 | EHVATGIDCYMQQFGVSK..ERAVEVMGNIVSDAWKDLNQELMREHVFPF..PLLMRVLNLSRVIDVFYRYQDA.YTNPKLLKEHI | 537 |

| | | |
|---|---|---|
| AAL79181 | HPIPI..... | 554 |
| ACN67535 | HPMSI..... | 555 |
| AAU05952 | QSLLIDPLHL | 569 |
| AAO85539 | VSLLETIPI | 547 |

B

| | | |
|---|---|---|
| ABY79206 | ................MAADEARSVSRLHSEEDMHGKHESTIWGDFFIHHVFGRFGQYLIMKDNVEIMKEEV.KKMLLDVG | 64 |
| ABJ16553 | ....MATSVPSVLLLPVPTCTIMLVSPVEGGDILHCKFFDHFPNVWGDYFLTFSEGTPSMLINMKRKAHVS.EEQ.VRRMILEC | 79 |

| | | |
|---|---|---|
| ABY79206 | SSDISH..KIDCIDTLERIGIDYHYIKEIDEIMCNVEEARCQDL..............DITTTSCLFYLIRKHGYHISSDVELKF | 133 |
| ABJ16553 | SSGPNLHVKLELVDTLERICTDYHYDKEIENVLRPVEEBDDTDNHY..........DLETIALRFYLIRKHGYYASPDVEQRF | 153 |

| | | |
|---|---|---|
| ABY79206 | REDKGDIVTNDARCLIRMYE....AAHVRVNGEEBILDNILIHIKRQLCCIVDDIEEPTLQEEVRY.....ALETPLFRRLNRVQAR | 209 |
| ABJ16553 | REEECNFTRDDNNNGTRSMLSLYNAAHLRIHGEEBILDCAIVFIRNYLQSVVKIQSPMADEVCS.....ALFRTPLFRRPRRVEAR | 233 |

| | | |
|---|---|---|
| ABY79206 | QEISTNYEKSTTRINMLLE..FSKLDENILTLYCEEIKDITLWWKEFCACANTTIYARDRMVEMHFWMMGVIFEPQYSYSRRMLT | 292 |
| ABJ16553 | HYISVNDKLFTRNETILE..FARLDFGILQSLYCEELNILTMWKRDLQLQHLSF.ARDRMVEMHFWMLGVIFEPQYSYGRTMLT | 315 |

| | | |
|---|---|---|
| ABY79206 | QLEMIVSVLDDLYDSHCTIEEGNAFIAALQRWDEEGVEQGFTMLRTIYTNIRAIIRAIEEDLNEQNKHAKLVEGILIDMAMCYN | 377 |
| ABJ16553 | KLFIEVSIPDDIYDNYSTLEESKLFITAIRWDEEAAEEILGGMKEFIYKKVLTIMKSIETFLRIGGNKHVDYVKNILIDATRCFY | 400 |

| | | |
|---|---|---|
| ABY79206 | AET..EWRDKKYVP..ATVEEHLKISARSSGCMHLVSCGFISMG.DVAITSEALEWASTYPKIVRAVCIIARLANDIMSYKREASN | 457 |
| ABJ16553 | NEV..PWRSEGADQVAATVEEHLKTSVPSSCCMHVPVYAEVAMGNDVITDDAINWGMAYPKIITSSCIVGRLLNDIASHDRECGS | 483 |

| | | |
|---|---|---|
| ABY79206 | NTMV.STVQTCAREYGTTIVEGAIDFRETIEEAWMDITHECLRCP..CEKALLERAVNLARHDFIYKDALGYTDSRSIKGILD | 539 |
| ABJ16553 | SSSSSSTVEACMREHCGILREEAYARIRELVEESWMDIAGECLRPAAACQPPLLEAVNAIRVLDFVYKDDCQDAYTHESSLKDTI | 568 |

| | | |
|---|---|---|
| ABY79206 | SLYVHID.. | 547 |
| ABJ16553 | HSIYILSV.. | 576 |

```
1    ACTGCTCGCG ATGCATCTAG ATTGGAGTGT CCTATCATTT TGAAAATGAG ATCAAAGAGG
61   CCTTACAAAC AATCTATGAT AGCCATGTTA ACGGCAATTG TGATGTTAAT TACGATCATA
121  ATAACGATCT CTACATAGTT GCTCTTCGAT TTCGGCTTCT AAGGCAGCAT GGTTACAAGG
181  TGTCAGCAGA TATATTTAAA AAATTCAGAG ATGAAAAAGG TGAATTCAAG GCCATGTTAA
241  CAAATGACGC GAAAGGCTTG CTATGTTTGT ATGAGGCGTC ATATCTGAGA GTACAAGGGG
301  AGAATATATT GGAAGAAGCA TGTGAATTTT CTAGGAAGCA CTTAAAATCT TTATTGTCCC
361  ATTTAAGCAC TCCTCTAGCT GACCAAGTTG AGCACTCCCT GGAGATACCT TTGCACAGAG
362      ← B63R (SP3)
421  GGATGCCAAG ATTGGAGGCA AGGCAGTATA TTTCCATCTA TGAAGCAGAC AATTCAACAC
422                      ← B62R (SP2)
481  GAAATGAGCT AATATTAGAA CTCGCAAAGC TAGATTTTAA TCTTTTGCAG GCGTTACACC
541  GGATAGAGCT AAGTGAGATC TCAAGGTGGT GGAAAGATAT TGATTTTGCA ACAAAGCTAC
              B61F →
601  CTTTTGCAAG AGATAGAATC
         ← B48R (SP1)
```

FIG. 10

```
   1    AGTAATTTAGCTGAGAAGTCTTGGTGGGAGTCTCTATCGTCGTCGTATCCAAAGCTCTTC
   1       V  I  *  L  R  S  L  G  G  S  L  Y  R  R  R  I  Q  S  S  S
  61    AATGGAGACCGATCTCAAGTCAACCTTTCTCAACGTTTATTCTGTTCTCAAGTCTGACCT
  21       M  E  T  D  L  K  S  T  F  L  N  V  Y  S  V  L  K  S  D  L
 121    TCTTCATGACCCTTCCTTCGAATTCACCAATGAATCTCGTCTCTGGGTTGATCGGATGCT
  41       L  H  D  P  S  F  E  F  T  N  E  S  R  L  W  V  D  R  M  L
 181    GGACTACAATGTACGTGGAGGGAAACTCAATCGGGGTCTCTCTGTTGTTGACAGTTTCAA
  61       D  Y  N  V  R  G  G  K  L  N  R  G  L  S  V  V  D  S  F  K
 241    ACTTTTGAAGCAAGGCAATGATTTGACTGAGCAAGAGGTCTTCCTCTCTTGTGCTCTCGG
  81       L  L  K  Q  G  N  D  L  T  E  Q  E  V  F  L  S  C  A  L  G
 301    TTGGTGCATTGAATGGCTCCAAGCTTATTTCCTTGTGCTTGATGACATTATGGATAACTC
 101       W  C  I  E  W  L  Q  A  Y  F  L  V  L  D  D  I  M  D  N  S
 361    TGTCACCCGCCGTGGTCAACCTTGCTGGTTCAGAGTTCCTCAGGTTGGTATGGTTGCCAT
 121       V  T  R  R  G  Q  P  C  W  F  R  V  P  Q  V  G  M  V  A  I
 421    CAATGATGGGATTCTACTTCGCAATCACATCCACAGGATTCTCAAAAAGCATTTCCGTGA
 141       N  D  G  I  L  L  R  N  H  I  H  R  I  L  K  K  H  F  R  D
 481    TAAGCCTTACTATGTTGACCTTGTTGATTTGTTTAATGAGGTTGAGTTGCAAACAGCTTG
 161       K  P  Y  Y  V  D  L  V  D  L  F  N  E  V  E  L  Q  T  A  C
 541    TGGCCAGATGATAGATTTGATCACCACCTTTGAAGGCGAAAAGGATTTGTCCAAGTACTC
 181       G  Q  M  I  D  L  I  T  T  F  E  G  E  K  D  L  S  K  Y  S
 601    ATTGTCAATCCACCGTCGTATTGTCCAGCACAAAACGGCTTATTACTCATTTTATCTCCC
 201       L  S  I  H  R  R  I  V  Q  H  K  T  A  Y  Y  S  F  Y  L  P
 661    TGTTGCTTGTGCGTTGCTTATGGCGGGCGAAAATTTGGAAAACCATATTGACGTGAAAAA
 221       V  A  C  A  L  L  M  A  G  E  N  L  E  N  H  I  D  V  K  N
 721    TGTTCTTGTTGACATGGGAATCTACTTCCAAGTGCAGGATGATTATCTGGATTGTTTTGC
 241       V  L  V  D  M  G  I  Y  F  Q  V  Q  D  D  Y  L  D  C  F  A
 781    TGATCCCGAGACGCTTGGCAAGATAGGAACAGATATAGAAGATTTCAAATGCTCTTGGTT
 261       D  P  E  T  L  G  K  I  G  T  D  I  E  D  F  K  C  S  W  L
 841    GGTGGTTAAGGCATTAGAACGCTGCAGCGAAGAACAAACTAAGATATTATATGAGAACTA
 281       V  V  K  A  L  E  R  C  S  E  E  Q  T  K  I  L  Y  E  N  Y
 901    TGGTAAAACCGACCCATCGAACGTTGCTAAAGTGAAGGATCTCTACAAAGAGCTGGATCT
 301       G  K  T  D  P  S  N  V  A  K  V  K  D  L  Y  K  E  L  D  L
 961    TGAGGGAGTGTTCATGGAGTATGAGAGCAAAAGCTACGAGAAGCTGACTGGAGCGATTGA
 321       E  G  V  F  M  E  Y  E  S  K  S  Y  E  K  L  T  G  A  I  E
1021    GGGACACCAAAGTAAAGCAATCCAAGCAGTGCTAAAATCCTTCTTGGCTAAGATCTACAA
 341       G  H  Q  S  K  A  I  Q  A  V  L  K  S  F  L  A  K  I  Y  K
1081    GAGGCAGAAGTAGTAGAGACAGACAAACATAAGTCTCAGCCCTCAAAAATTTCCTGTTAT
 361       R  Q  K  *  *  R  Q  T  N  I  S  L  S  P  Q  K  F  P  V  M
1141    GTCTTTGATTCTTGGTTGGTGATTTGTGTAATTCTGTTAAGTGCTCTGATTTTCAGGGGG
 381       S  L  I  L  G  W  *  F  V  *  F  C  *  V  L  *  F  S  G  G
1201    AATAATAAACCTGCCTCACTCTGT
 401       I  I  N  L  P  H  S
```

FIG. 11

SEQUENCE LISTING

```
<160> NUMBER OF SEQ ID NOS: 28

<210> SEQ ID NO 1
<211> LENGTH: 1668
<212> TYPE: DNA
<213> ORGANISM: Artificial Sequence
<220> FEATURE:
<223> OTHER INFORMATION: Synthetic Sequence

<400> SEQUENCE: 1
atgtccgctc aagttctagc aacggtttcc agttcaacag aaaaaactgt tcgtcccatt      60
gctggtttcc atcctaactt atggggagac tatttcctga ccctcgcttc tgattgcaag     120
acaaatgata ctacgcacca agaggaatac gaagcgctga agcaagaagt cagaagcatg     180
ataacggcta cggcagatac acctgcccag aagttgcaat tggttgatgc agtccaacga     240
ttgggtgtgg cctatcactt cgaacaggag atagaagatg caatggaaaa gatttatcac     300
gatgactttg ataataacga tgatgtcgat ctctacactg tttctcttcg ttttcgactg     360
cttaggcagc aaggatttaa ggttccgtgt gatgtgttcg cgaagttcaa agatgatgaa     420
ggtaaattca aggcatcatt ggtgcaggat gttcatggca ttctaagttt gtatgaggca     480
ggacacttgg ccattcgcgg agaagggata ttagatgaag ccattgcttt cactagaact     540
```

-continued

```
caccttcagt caatggtatc tcaggatgta tgccctaata atcttgctga acaaattaat    600
catactctcg actgtcctct ccgcagagcc cttccaagag tggagacaag attttttcttg   660
tctgtctatc caagagatga taaacacgat aaaactttgt taaagttttc aaagttagac    720
tttaaccatg tgcaaagaat acatcagaag gaattaagtg ccatcacacg tggtggaaaa    780
gatttagact tcactacaaa gctaccttat gcaagagaca gaatcgtaga gttgtatttt    840
tggattgtag ggacgtattt tgaaccaaag tacactttag cgagaaaaat aatgaccaaa    900
acaatttaca cggcatctat catagatgac actttcgacg cttatggttt ctttgaagag    960
ctcaaactct tagcagaagc agtccagagg tgggacattg gagccatgga tatacttcca   1020
gaatacatga aagtgcttta taaggccctt ttagatactt tcaatgaaat tgagcaagac   1080
ttggccaagg aaggaagatc gtcctgctta ccttatggca aagaaaagat gcaagagctt   1140
gttcaaatgt actttgttca agccaagtgg ttcagtgaag ttatgttcc gacatgggac    1200
gaatattatc cggttggact tgtaagttgc ggctacttca tgcttgcgac aaattccttc   1260
cttggcatgt gtgatgttgc aaacaaggaa gcttttgaat ggatatccaa ggaccctaag   1320
atttcaacag cgtcatcagt tatctgcaga cttaggaatg acattgtttc ccaccagttt   1380
gaacagaaga gaggacatat tgcctcagga gttgaatgct acattaagca gtatggtgtt   1440
tcagcagaag aggtagttac agtttttact gaagaagttg agaatgcatg gaaagatatg   1500
aatgaggaat tcctgaaacc aactgctttt cctgtggctt tgattgagag accttttcaat  1560
atcgcacgtg tgattgaatt tctaaacaag aagggtgatt ggtacactca ttctcatgcg   1620
attaaagacc agattgccgc agtgctcaga gaccctgtta ccatctga                1668
```

<210> SEQ ID NO 2
<211> LENGTH: 555
<212> TYPE: PRT
<213> ORGANISM: Artificial Sequence
<220> FEATURE:
<223> OTHER INFORMATION: Synthetic Peptide

<400> SEQUENCE: 2

```
Met Ser Ala Gln Val Leu Ala Thr Val Ser Ser Thr Glu Lys Thr
 1               5                  10                  15

Val Arg Pro Ile Ala Gly Phe His Pro Asn Leu Trp Gly Asp Tyr Phe
                20                  25                  30

Leu Thr Leu Ala Ser Asp Cys Lys Thr Asn Asp Thr Thr His Gln Glu
            35                  40                  45

Glu Tyr Glu Ala Leu Lys Gln Glu Val Arg Ser Met Ile Thr Ala Thr
        50                  55                  60

Ala Asp Thr Pro Ala Gln Lys Leu Gln Leu Val Asp Ala Val Gln Arg
65                  70                  75                  80

Leu Gly Val Ala Tyr His Phe Glu Gln Glu Ile Glu Asp Ala Met Glu
                85                  90                  95

Lys Ile Tyr His Asp Asp Phe Asp Asn Asn Asp Val Asp Leu Tyr
                100                 105                 110

Thr Val Ser Leu Arg Phe Arg Leu Leu Arg Gln Gln Gly Phe Lys Val
            115                 120                 125

Pro Cys Asp Val Phe Ala Lys Phe Lys Asp Asp Glu Gly Lys Phe Lys
        130                 135                 140

Ala Ser Leu Val Gln Asp Val His Gly Ile Leu Ser Leu Tyr Glu Ala
145                 150                 155                 160
```

Gly His Leu Ala Ile Arg Gly Glu Gly Ile Leu Asp Glu Ala Ile Ala
            165                 170                 175

Phe Thr Arg Thr His Leu Gln Ser Met Val Ser Gln Asp Val Cys Pro
        180                 185                 190

Asn Asn Leu Ala Glu Gln Ile Asn His Thr Leu Asp Cys Pro Leu Arg
        195                 200                 205

Arg Ala Leu Pro Arg Val Glu Thr Arg Phe Phe Leu Ser Val Tyr Pro
        210                 215                 220

Arg Asp Asp Lys His Asp Lys Thr Leu Leu Lys Phe Ser Lys Leu Asp
225                 230                 235                 240

Phe Asn His Val Gln Arg Ile His Gln Lys Glu Leu Ser Ala Ile Thr
            245                 250                 255

Arg Trp Trp Lys Asp Leu Asp Phe Thr Thr Lys Leu Pro Tyr Ala Arg
        260                 265                 270

Asp Arg Ile Val Glu Leu Tyr Phe Trp Ile Val Gly Thr Tyr Phe Glu
        275                 280                 285

Pro Lys Tyr Thr Leu Ala Arg Lys Ile Met Thr Lys Thr Ile Tyr Thr
        290                 295                 300

Ala Ser Ile Ile Asp Asp Thr Phe Asp Ala Tyr Gly Phe Phe Glu Glu
305                 310                 315                 320

Leu Lys Leu Leu Ala Glu Ala Val Gln Arg Trp Asp Ile Gly Ala Met
            325                 330                 335

Asp Ile Leu Pro Glu Tyr Met Lys Val Leu Tyr Lys Ala Leu Leu Asp
        340                 345                 350

Thr Phe Asn Glu Ile Glu Gln Asp Leu Ala Lys Glu Gly Arg Ser Ser
        355                 360                 365

Cys Leu Pro Tyr Gly Lys Glu Lys Met Gln Glu Leu Val Gln Met Tyr
        370                 375                 380

Phe Val Gln Ala Lys Trp Phe Ser Glu Gly Tyr Val Pro Thr Trp Asp
385                 390                 395                 400

Glu Tyr Tyr Pro Val Gly Leu Val Ser Cys Gly Tyr Phe Met Leu Ala
            405                 410                 415

Thr Asn Ser Phe Leu Gly Met Cys Asp Val Ala Asn Lys Glu Ala Phe
        420                 425                 430

Glu Trp Ile Ser Lys Asp Pro Lys Ile Ser Thr Ala Ser Ser Val Ile
        435                 440                 445

Cys Arg Leu Arg Asn Asp Ile Val Ser His Gln Phe Glu Gln Lys Arg
450                 455                 460

Gly His Ile Ala Ser Gly Val Glu Cys Tyr Ile Lys Gln Tyr Gly Val
465                 470                 475                 480

Ser Ala Glu Glu Val Val Thr Val Phe Thr Glu Glu Val Glu Asn Ala
            485                 490                 495

Trp Lys Asp Met Asn Glu Glu Phe Leu Lys Pro Thr Ala Phe Pro Val
        500                 505                 510

Ala Leu Ile Glu Arg Pro Phe Asn Ile Ala Arg Val Ile Glu Phe Leu
        515                 520                 525

Asn Lys Lys Gly Asp Trp Tyr Thr His Ser His Ala Ile Lys Asp Gln
530                 535                 540

Ile Ala Ala Val Leu Arg Asp Pro Val Thr Ile
545                 550                 555

<210> SEQ ID NO 3
<211> LENGTH: 1704
<212> TYPE: DNA

<213> ORGANISM: Artificial Sequence
<220> FEATURE:
<223> OTHER INFORMATION: Synthetic sequence

<400> SEQUENCE: 3

```
atgagggatg ttaagagtgt tctttcttca aagaaagca cgaaagccga tgtgaaccgt      60
cgatcctcga attatcatcc tagcatttgg ggtgatcatt tcattaatgt gtcatcaaat    120
gaaaagtaca ccaatacgga agtcgaaaag cggtttgaaa cattaaaagc agaaattgaa    180
aagttgctgg tgagcaataa tacagcatgg aaaacacttg aagaaattgt ggctattgtt    240
aatcaacttc aacgccttgg tgtggcctat cattttgaaa atgagatcaa agaggcctta    300
caaacaatct atgatagcca tgttaacggc aattgtgatg ttaattacga tcataataac    360
gatctctaca tagttgctct tcgatttcgg cttctaaggc agcatggtta caaggtgtca    420
gcagatatat ttaaaaaatt cagagatgaa aaaggtgaat tcaaggccat gttaacaaat    480
gacgcgaaag gcttgctatg tttgtatgag gcgtcatatc tgagagtaca aggggagaat    540
atattggaag aagcatgtga attttctagg aagcacttaa atctttatt gtcccattta    600
agcactcctc tagctgacca agttgagcac tccctggaga tacctttgca cagagggatg    660
ccaagattgg aggcaaggca gtatatttcc atctatgaag cagacaattc aacacgaaat    720
gagctaatat tagaacttgc aaagctagat tttaatcttt tgcaggcgtt acaccggata    780
gagctaagtg agatctcaag gtggtggaaa gatattgatt ttgcaacaaa gctaccttt    840
gcaagagata gagtggtgga gggctatttc tggattttgg gagtatattt tgagccaaaa    900
tttttattgg ctagaaaaat tctaaccaaa gtgatatcaa tggcttcaat tattgatgac    960
atttatgatg cttatggtac aatagaagaa cttgagcttt ttgccacagc aattgagagg   1020
tgggatctca gtgccataga tctgcttcct gagtacatga agttgtgcta ttgcgctctc   1080
ctggatgctt acagcgaatt tgagaaagat ttggccagca aggaatatat gtacggccta   1140
ccttttgcta aagaatcgat gaagattttg gtgagaagtt acatcatcga agctagatgg   1200
tgtgaccaac aatatgtacc gacaatggag gaatacatgc gcgttgcact actttcatgt   1260
ggctacttac tgttatcaac atcttcattt ctgggaatgg aagatattgt aacaaaagaa   1320
gcctttgaat gggtatccgg caaccctaaa atcgttcagg cttcctcaat aattgcaga    1380
ctcatggatg acattgtctc tcataagttt gagcaacaga gaggacatgt ggcctcagct   1440
gttgaatgct acatgaagca gcatggagtt tctgaggaag aggcagttaa agtgtttcgg   1500
gagaaagttg ggaatgcgtg gaaagataya aatgaggagc tcatgagacc acctgttgtt   1560
cctatgcctt tgctcgaacg ggttcttaat cttgctcgtt taatggatgt gctgtaccaa   1620
aataatgatt cctatacaaa tcctcacttg atgaaagatc atgtagccgc attgcttaag   1680
gatcctgttt tctttgaaga ctag                                          1704
```

<210> SEQ ID NO 4
<211> LENGTH: 567
<212> TYPE: PRT
<213> ORGANISM: Artificial Sequence
<220> FEATURE:
<223> OTHER INFORMATION: Synthetic peptide

<400> SEQUENCE: 4

```
Met Arg Asp Val Lys Ser Val Leu Ser Ser Lys Glu Ser Thr Lys Ala
1               5                   10                  15

Asp Val Asn Arg Arg Ser Ser Asn Tyr His Pro Ser Ile Trp Gly Asp
            20                  25                  30
```

-continued

His Phe Ile Asn Val Ser Ser Asn Glu Lys Tyr Thr Asn Thr Glu Val
            35                  40                  45

Glu Lys Arg Phe Glu Thr Leu Lys Ala Glu Ile Glu Lys Leu Leu Val
 50                  55                  60

Ser Asn Asn Thr Ala Trp Lys Thr Leu Glu Glu Ile Val Ala Ile Val
 65                  70                  75                  80

Asn Gln Leu Gln Arg Leu Gly Val Ala Tyr His Phe Glu Asn Glu Ile
                85                  90                  95

Lys Glu Ala Leu Gln Thr Ile Tyr Asp Ser His Val Asn Gly Asn Cys
                100                 105                 110

Asp Val Asn Tyr Asp His Asn Asn Asp Leu Tyr Ile Val Ala Leu Arg
                115                 120                 125

Phe Arg Leu Leu Arg Gln His Gly Tyr Lys Val Ser Ala Asp Ile Phe
 130                 135                 140

Lys Lys Phe Arg Asp Glu Lys Gly Glu Phe Lys Ala Met Leu Thr Asn
145                 150                 155                 160

Asp Ala Lys Gly Leu Leu Cys Leu Tyr Glu Ala Ser Tyr Leu Arg Val
                165                 170                 175

Gln Gly Glu Asn Ile Leu Glu Glu Ala Cys Glu Phe Ser Arg Lys His
                180                 185                 190

Leu Lys Ser Leu Leu Ser His Leu Ser Thr Pro Leu Ala Asp Gln Val
                195                 200                 205

Glu His Ser Leu Glu Ile Pro Leu His Arg Gly Met Pro Arg Leu Glu
                210                 215                 220

Ala Arg Gln Tyr Ile Ser Ile Tyr Glu Ala Asp Asn Ser Thr Arg Asn
225                 230                 235                 240

Glu Leu Ile Leu Glu Leu Ala Lys Leu Asp Phe Asn Leu Leu Gln Ala
                245                 250                 255

Leu His Arg Ile Glu Leu Ser Glu Ile Ser Arg Trp Trp Lys Asp Ile
                260                 265                 270

Asp Phe Ala Thr Lys Leu Pro Phe Ala Arg Asp Arg Val Val Glu Gly
                275                 280                 285

Tyr Phe Trp Ile Leu Gly Val Tyr Phe Glu Pro Lys Phe Leu Leu Ala
                290                 295                 300

Arg Lys Ile Leu Thr Lys Val Ile Ser Met Ala Ser Ile Ile Asp Asp
305                 310                 315                 320

Ile Tyr Asp Ala Tyr Gly Thr Ile Glu Glu Leu Glu Leu Phe Ala Thr
                325                 330                 335

Ala Ile Glu Arg Trp Asp Leu Ser Ala Ile Asp Leu Leu Pro Glu Tyr
                340                 345                 350

Met Lys Leu Cys Tyr Cys Ala Leu Leu Asp Ala Tyr Ser Glu Phe Glu
                355                 360                 365

Lys Asp Leu Ala Ser Lys Gly Ile Leu Tyr Gly Leu Pro Phe Ala Lys
                370                 375                 380

Glu Ser Met Lys Ile Leu Val Arg Ser Tyr Ile Ile Glu Ala Arg Trp
385                 390                 395                 400

Cys Asp Gln Gln Tyr Val Pro Thr Met Glu Glu Tyr Met Arg Val Ala
                405                 410                 415

Leu Leu Ser Cys Gly Tyr Leu Leu Leu Ser Thr Ser Ser Phe Leu Gly
                420                 425                 430

Met Glu Asp Ile Val Thr Lys Glu Ala Phe Glu Trp Val Ser Gly Asn
                435                 440                 445

```
Pro Lys Ile Val Gln Ala Ser Ser Ile Ile Cys Arg Leu Met Asp Asp
            450                 455                 460

Ile Val Ser His Lys Phe Glu Gln Gln Arg Gly His Val Ala Ser Ala
465                 470                 475                 480

Val Glu Cys Tyr Met Lys Gln His Gly Val Ser Glu Glu Ala Val
                485                 490                 495

Lys Val Phe Arg Glu Lys Val Gly Asn Ala Trp Lys Asp Ile Asn Glu
                500                 505                 510

Glu Leu Met Arg Pro Val Val Pro Met Pro Leu Leu Glu Arg Val
            515                 520                 525

Leu Asn Leu Ala Arg Leu Met Asp Val Leu Tyr Gln Asn Asn Asp Ser
530                 535                 540

Tyr Thr Asn Pro His Leu Met Lys Asp His Val Ala Ala Leu Leu Lys
545                 550                 555                 560

Asp Pro Val Phe Phe Glu Asp
                565

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence

<400> SEQUENCE: 5
aaaaatgtcc gctcaagttc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic sequence

<400> SEQUENCE: 6
tcagatggta acagggtctc                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic sequence

<400> SEQUENCE: 7
gcatgaggga tgttaagag                                                19

<210> SEQ ID NO 8
<211> LENGTH: 22
<212> TYPE: DNA
<213> ORGANISM: Artificial Sequence
<220> FEATURE:
<223> OTHER INFORMATION: Synthetic sequence

<400> SEQUENCE: 8
ctgttttctt tgaagactag gc                                            22

<210> SEQ ID NO 9
<211> LENGTH: 50
<212> TYPE: DNA
<213> ORGANISM: Artificial Sequence
<220> FEATURE:
<223> OTHER INFORMATION: Synthetic sequence
```

<400> SEQUENCE: 9
gcgatcgcca tgcatcacca tcaccatcac ggatccgctc aagttctagc         50

<210> SEQ ID NO 10
<211> LENGTH: 29
<212> TYPE: DNA
<213> ORGANISM: Artificial Sequence
<220> FEATURE:
<223> OTHER INFORMATION: Synthetic sequence

<400> SEQUENCE: 10
gtttaaactc agatggtaac agggtctct                                29

<210> SEQ ID NO 11
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: k=G or T
<220> FEATURE:
<221> NAME/KEY: misc_feature
<222> LOCATION: (5)..(5)
<223> OTHER INFORMATION: k=G or T
<220> FEATURE:
<221> NAME/KEY: misc_feature
<222> LOCATION: (8)..(8)
<223> OTHER INFORMATION: r=A or G
<220> FEATURE:
<221> NAME/KEY: misc_feature
<222> LOCATION: (9)..(9)
<223> OTHER INFORMATION: k=G or T
<220> FEATURE:
<221> NAME/KEY: misc_feature
<222> LOCATION: (17)..(17)
<223> OTHER INFORMATION: y=T or C

<400> SEQUENCE: 11
tkggkgtrkc ktatcayttt ga                                       22

<210> SEQ ID NO 12
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: r=a or g
<220> FEATURE:
<221> NAME/KEY: misc_feature
<222> LOCATION: (7)..(7)
<223> OTHER INFORMATION: k=g or t
<220> FEATURE:
<221> NAME/KEY: misc_feature
<222> LOCATION: (9)..(9)
<223> OTHER INFORMATION: m=c or a
<220> FEATURE:
<221> NAME/KEY: misc_feature
<222> LOCATION: (12)..(12)
<223> OTHER INFORMATION: y=t or c

<400> SEQUENCE: 12
ggagtrkcmt aycattttga a                                        21

<210> SEQ ID NO 13

```
<211> LENGTH: 23
<212> TYPE: DNA
<213> ORGANISM: Artificial Sequence
<220> FEATURE:
<223> OTHER INFORMATION: Synthetic sequence

<400> SEQUENCE: 13
ggsatgttaa gtttgtayga rgc                                              23

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: y=t or c
<220> FEATURE:
<221> NAME/KEY: misc_feature
<222> LOCATION: (9)..(9)
<223> OTHER INFORMATION: w=t or a
<220> FEATURE:
<221> NAME/KEY: misc_feature
<222> LOCATION: (11)..(11)
<223> OTHER INFORMATION: w=t or a
<220> FEATURE:
<221> NAME/KEY: misc_feature
<222> LOCATION: (18)..(18)
<223> OTHER INFORMATION: k=g or t
<220> FEATURE:
<221> NAME/KEY: misc_feature
<222> LOCATION: (21)..(21)
<223> OTHER INFORMATION: y=t or c

<400> SEQUENCE: 14
gatgayacwt wtgacgckta ygg                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: r=a or g
<220> FEATURE:
<221> NAME/KEY: misc_feature
<222> LOCATION: (6)..(6)
<223> OTHER INFORMATION: m=c or a
<220> FEATURE:
<221> NAME/KEY: misc_feature
<222> LOCATION: (13)..(13)
<223> OTHER INFORMATION: w=t or a
<220> FEATURE:
<221> NAME/KEY: misc_feature
<222> LOCATION: (15)..(15)
<223> OTHER INFORMATION: w=t or a
<220> FEATURE:
<221> NAME/KEY: misc_feature
<222> LOCATION: (18)..(18)
<223> OTHER INFORMATION: r=a or g

<400> SEQUENCE: 15
ccrtamgcgt cawtwgtrtc atc                                              23

<210> SEQ ID NO 16
<211> LENGTH: 23
<212> TYPE: DNA
<213> ORGANISM: Artificial Sequence
```

<220> FEATURE:
<223> OTHER INFORMATION: Synthetic sequence

<400> SEQUENCE: 16
tcctcatcat tcatatcttt cca                                            23

<210> SEQ ID NO 17
<211> LENGTH: 17
<212> TYPE: DNA
<213> ORGANISM: Artificial Sequence
<220> FEATURE:
<223> OTHER INFORMATION: Synthetic sequence

<400> SEQUENCE: 17
ctatctcttg caaaagg                                                   17

<210> SEQ ID NO 18
<211> LENGTH: 548
<212> TYPE: PRT
<213> ORGANISM: Artemisia annua

<400> SEQUENCE: 18

```
Met Ser Val Lys Glu Glu Lys Val Ile Arg Pro Ile Val His Phe Pro
1               5                   10                  15

Pro Ser Val Trp Ala Asp Gln Phe Leu Ile Phe Asp Asp Lys Gln Ala
            20                  25                  30

Glu Gln Ala Asn Val Glu Gln Val Val Asn Glu Leu Arg Glu Asp Val
        35                  40                  45

Arg Lys Asp Leu Val Ser Ser Leu Asp Val Gln Thr Glu His Thr Asn
50                  55                  60

Leu Leu Lys Leu Ile Asp Ala Ile Gln Arg Leu Gly Ile Ala Tyr His
65                  70                  75                  80

Phe Glu Glu Glu Ile Glu Gln Ala Leu Gln His Ile Tyr Asp Thr Tyr
                85                  90                  95

Gly Asp Asp Trp Lys Gly Arg Ser Pro Ser Leu Trp Phe Arg Ile Leu
            100                 105                 110

Arg Gln Gln Gly Phe Tyr Val Ser Cys Asp Ile Phe Lys Asn Tyr Lys
        115                 120                 125

Lys Glu Asp Gly Ser Phe Lys Glu Ser Leu Thr Asn Asp Val Glu Gly
    130                 135                 140

Leu Leu Glu Leu Tyr Glu Ala Thr Tyr Leu Arg Val Gln Gly Glu Gly
145                 150                 155                 160

Val Leu Asp Asp Ala Leu Val Phe Thr Arg Thr Cys Leu Glu Lys Ile
                165                 170                 175

Ala Lys Asp Leu Val His Thr Asn Pro Thr Leu Ser Thr Tyr Ile Gln
            180                 185                 190

Glu Ala Leu Lys Gln Pro Leu His Lys Arg Leu Thr Arg Leu Glu Ala
        195                 200                 205

Leu Arg Tyr Ile Pro Met Tyr Glu Gln Gln Ala Ser His Asn Glu Ser
    210                 215                 220

Leu Leu Lys Leu Ala Lys Leu Gly Phe Asn Leu Leu Gln Ser Leu His
225                 230                 235                 240

Arg Lys Glu Leu Ser Glu Val Ser Arg Trp Trp Lys Gly Leu Asp Val
                245                 250                 255

Pro Asn Asn Leu Pro Tyr Ala Arg Asp Arg Met Val Glu Cys Tyr Phe
            260                 265                 270

Trp Ala Leu Gly Val Tyr Phe Glu Pro Lys Tyr Ser Gln Ala Arg Ile
```

```
            275                 280                 285
Phe Leu Ala Lys Val Ile Ser Leu Ala Thr Val Leu Asp Asp Thr Tyr
290                 295                 300
Asp Ala Tyr Gly Thr Tyr Glu Glu Leu Lys Ile Phe Thr Glu Ala Ile
305                 310                 315                 320
Gln Arg Trp Ser Ile Thr Cys Ile Asp Met Leu Pro Glu Tyr Leu Lys
                325                 330                 335
Leu Leu Tyr Gln Gly Val Leu Asp Ile Tyr Ile Glu Met Glu Glu Ile
            340                 345                 350
Met Gly Lys Glu Gly Lys Ala His His Leu Ser Tyr Ala Lys Glu Ser
        355                 360                 365
Met Lys Glu Phe Ile Arg Ser Tyr Met Met Glu Ala Lys Trp Ala Asn
370                 375                 380
Glu Gly Tyr Val Pro Thr Ala Glu Glu His Met Ser Val Ala Phe Val
385                 390                 395                 400
Ser Ser Gly Tyr Ser Met Leu Ala Thr Thr Cys Phe Val Gly Met Gly
                405                 410                 415
Asp Ile Val Thr Asp Glu Ala Phe Lys Trp Ala Leu Thr Lys Pro Pro
            420                 425                 430
Ile Ile Lys Ala Ser Cys Ala Ile Ala Arg Leu Met Asp Asp Ile His
        435                 440                 445
Ser Gln Lys Glu Lys Glu Arg Ile His Val Ala Ser Ser Val Glu
450                 455                 460
Ser Tyr Met Lys Gln Tyr Asp Val Thr Glu His Val Leu Lys Val
465                 470                 475                 480
Phe Asn Lys Lys Ile Glu Asp Ala Trp Lys Asp Ile Thr Arg Glu Ser
                485                 490                 495
Leu Val Arg Lys Asp Ile Pro Met Pro Leu Met Met Arg Val Ile Asn
            500                 505                 510
Leu Ala Gln Val Met Asp Val Leu Tyr Lys His Lys Asp Gly Phe Thr
        515                 520                 525
Asn Val Gly Glu Glu Leu Lys Asp His Ile Lys Ser Leu Leu Val His
530                 535                 540
Pro Ile Pro Ile
545

<210> SEQ ID NO 19
<211> LENGTH: 547
<212> TYPE: PRT
<213> ORGANISM: Mikrania micrantha

<400> SEQUENCE: 19

Met Gly Cys Lys Gln Glu Ser Phe Arg Pro Phe Arg Ser Thr Ser Pro
1               5                   10                  15
Ser Val Trp Gly Asp Met Phe Leu Asn Tyr Glu Lys Lys Ala Glu Gln
            20                  25                  30
Cys Asp Val Glu Leu Thr Val Glu Asp Leu Lys Glu Lys Val Arg Glu
        35                  40                  45
Ala Ile Thr Gly Ala Leu Gly Asn Pro Lys Glu His Val Asn Leu Leu
    50                  55                  60
Lys Leu Ile Asp Ala Ile Gln Arg Leu Gly Ile Pro Tyr Tyr Phe Glu
65                  70                  75                  80
Asp Glu Ile Thr Asn Ala Leu Gln His Leu Tyr Glu Ala Tyr Gly Asp
                85                  90                  95
```

-continued

Glu Trp Val Gly Gly Ser Pro Ser Ile Trp Phe Arg Leu Leu Arg Gln
                100                 105                 110

His Gly Phe Tyr Val Ser Cys Asp Ile Phe Asn Lys Tyr Tyr Lys Asp
            115                 120                 125

Lys His Gly Asp Phe Lys Glu Ser Leu Ile Asn Asp Asp Glu Glu Met
        130                 135                 140

Val Glu Leu Tyr Glu Ala Thr Ser Leu Arg Val Arg Gly Glu Val Val
145                 150                 155                 160

Leu Asp Glu Ala Phe Glu Phe Thr Arg Asn His Phe Ala Asn Ile Ala
                165                 170                 175

Lys Glu Pro Arg Cys Ser Asn Ala Thr Leu Ser Thr His Ile Gln Val
            180                 185                 190

Ala Leu Glu Thr Pro Leu His Lys Arg Ile Pro Arg Leu Asp Ala Leu
        195                 200                 205

Arg Tyr Ile Arg Phe Tyr Glu Lys Gln Ala Ser His Asn Glu Ser Leu
210                 215                 220

Leu Lys Leu Ala Lys Leu Gly Phe Asn Leu Leu Gln Ser Leu His Arg
225                 230                 235                 240

Ser Glu Leu Ser Gln Val Ser Lys Trp Trp Lys Asp Val Asp Val Gln
                245                 250                 255

Lys Asn Leu Pro Tyr Ala Arg Asp Arg Met Val Glu Ser Tyr Phe Trp
            260                 265                 270

Ala Ile Gly Val Tyr Ser Glu Pro Lys Tyr Ser Leu Gly Arg Val Phe
        275                 280                 285

Leu Ala Lys Val Ile Gln Leu Ala Thr Ala Ile Asp Asp Thr Phe Asp
290                 295                 300

Ala Tyr Gly Thr Tyr Glu Glu Leu Gln Thr Phe Thr Arg Ala Val Glu
305                 310                 315                 320

Arg Trp Ser Ile Thr Cys Leu Asp Glu Leu Pro Glu Tyr Met Lys Leu
                325                 330                 335

Leu Tyr Gln Val Leu Leu Asp Leu Tyr Gly Glu Met Glu Pro Ile Met
            340                 345                 350

Glu Lys Glu Gln Leu Thr Pro Leu Phe Asn Cys Ser Lys Glu Phe Met
        355                 360                 365

Ile Glu Thr Val Lys Ala Tyr Met Val Glu Ala Lys Trp Val Tyr Glu
370                 375                 380

Gly His Ile Pro Thr Lys Asp Glu His Thr Ser Ile Ala Phe Ala Thr
385                 390                 395                 400

Gly Gly Gly Pro Leu Leu Met Ser Ser Cys Tyr Leu Gly Met Gly Asp
                405                 410                 415

Ile Ile Thr Asn Asp Ser Ile Asn Trp Val Ile Ser Glu Pro Pro Leu
            420                 425                 430

Leu Lys Ala Thr Asn Met Ile Gly Arg Leu Leu Asn Asp Ile Val Ser
        435                 440                 445

Ser Lys Lys Glu Gln Glu Arg Val His Phe Gln Ser Ile Val Gln Cys
450                 455                 460

Tyr Lys Lys Gln Tyr Asp Val Ser Glu Glu His Ala Ile Asn Leu Val
465                 470                 475                 480

Arg Glu Glu Ile Glu Asp Val Trp Lys Asp Ile Asn Lys Asp Ser Leu
                485                 490                 495

Thr Ala Lys Asp Val Pro Arg Pro Leu Ile Leu Val Val Val Asn Tyr
            500                 505                 510

Ala Arg Thr Leu Tyr Tyr Leu Tyr Lys Tyr Asn Asp Asn Phe Phe Glu

```
            515                 520                 525
Val Glu Glu Asp Ile Lys Glu Asp Ile Lys Ser Leu Leu Ile His Pro
    530                 535                 540

Met Ser Ile
545

<210> SEQ ID NO 20
<211> LENGTH: 567
<212> TYPE: PRT
<213> ORGANISM: Cucumis sativus

<400> SEQUENCE: 20

Met Ser Ser His Phe Pro Ala Ser Ile Met Lys Thr Asn Asp Ile Tyr
1               5                   10                  15

Asp Thr Lys Arg Ser Leu Ala Asn Phe His Pro Thr Ile Trp Lys Glu
            20                  25                  30

His Phe Leu Ser Phe Thr Phe Asp Asp Ala Leu Lys Val Asp Gly Gly
        35                  40                  45

Met Lys Glu Arg Ile Glu Lys Leu Lys Glu Glu Ile Arg Met Met Val
    50                  55                  60

Ile Ala Ser Val Gln Asn Pro Leu Val Lys Leu Asn Leu Val Asp Ser
65                  70                  75                  80

Ile Gln Arg Leu Gly Val Ser Tyr His Phe Glu Asp Glu Ile Asp Gln
                85                  90                  95

Phe Leu Glu His Met Tyr Val Ser Tyr Asn Asn Ser Leu Leu Phe Ser
            100                 105                 110

Ser Asn Asp Ser Gln Asp Asp Leu His Ile Ser Ala Leu Leu Phe
        115                 120                 125

Arg Leu Leu Arg Gln His Gly Tyr Arg Ile Ser Cys Asp Ile Phe Leu
    130                 135                 140

Lys Phe Met Asp Asn Asn Gly Lys Phe Lys Glu Ser Leu Val Glu Asp
145                 150                 155                 160

Glu Arg Gly Ile Leu Ser Leu Tyr Glu Ala Ser His Met Arg Gly His
                165                 170                 175

Gly Glu Ala Leu Leu Glu Glu Ala Leu Glu Phe Thr Thr Thr His Leu
            180                 185                 190

Lys Ala Tyr Ile His Leu Tyr Ser Asn Ile Asn Pro Asn Phe Ala Ser
        195                 200                 205

Glu Val Ser Asn Ala Leu Lys Leu Pro Ile Arg Lys Cys Val Pro Arg
    210                 215                 220

Val Lys Ala Arg Glu Tyr Phe Glu Ile Tyr Gln Gln Pro Ser His
225                 230                 235                 240

Asn Glu Thr Leu Leu Thr Phe Ser Lys Leu Asp Phe Asn Ile Leu Gln
                245                 250                 255

Lys Leu His Gln Lys Glu Ile Ala Glu Ile Cys Arg Trp Trp Lys Asp
            260                 265                 270

Leu Asn Val Ser Thr Asn Phe Pro Phe Ala Arg Asp Arg Ile Val Glu
        275                 280                 285

Cys Tyr Phe Trp Ile Leu Ser Ile Tyr Phe Glu Pro Tyr Phe Lys Phe
    290                 295                 300

Gly Arg Lys Ile Leu Thr Lys Val Ile Ala Met Thr Ser Ile Met Asp
305                 310                 315                 320

Asp Ile Tyr Asp Ala Tyr Gly Thr Phe Glu Glu Leu Gln Leu Phe Thr
                325                 330                 335
```

```
Leu Ala Ile Lys Arg Trp Asp Met Ser Met Val Asn Leu Leu Pro Gln
            340                 345                 350

Tyr Met Lys Val His Tyr Thr Thr Leu Leu Asp Leu Phe Glu Glu Met
        355                 360                 365

Asp Lys Gly Ile Val Asn Asp Gly Ile Ser Tyr Arg Ser Cys Phe Gly
    370                 375                 380

Lys Glu Ala Met Lys Arg Gln Ala Glu Ser Tyr Phe Lys Glu Ala Glu
385                 390                 395                 400

Trp Leu Asn Lys Asn Tyr Lys Pro Lys Tyr Gly Glu Tyr Met Glu Val
                405                 410                 415

Ala Leu Ala Ser Ser Gly Tyr Glu Leu Leu Ser Thr Ile Ser Phe Val
            420                 425                 430

Cys Met Gly Asp Ile Ala Thr Lys Glu Val Phe Glu Trp Leu Phe Asp
        435                 440                 445

Cys Pro Gln Ile Leu Lys Ala Ser Thr Thr Ile Ser Arg Leu Met Asp
    450                 455                 460

Asp Val Val Ser Tyr Lys Phe Glu Lys Glu Arg Glu His Ile Val Ser
465                 470                 475                 480

Ala Val Glu Cys Tyr Met Ser Asn His Gly Arg Ser Glu Asp Glu Thr
                485                 490                 495

Cys Ala Glu Leu Leu Lys Gln Val Glu Asp Ala Trp Lys Thr Ile Asn
            500                 505                 510

Glu Cys Cys Leu His Pro Met Asn Val Pro Met Pro Phe Leu Ile Cys
        515                 520                 525

Leu Leu Asn Leu Thr Arg Val Met Ala Leu Leu Tyr Ser His Glu Asp
    530                 535                 540

Gly Tyr Thr Asn Ser Lys Gly Arg Thr Lys Leu Leu Ile Gln Ser Leu
545                 550                 555                 560

Leu Ile Asp Pro Leu His Leu
                565

<210> SEQ ID NO 21
<211> LENGTH: 547
<212> TYPE: PRT
<213> ORGANISM: Arabidopsis thaliana

<400> SEQUENCE: 21

Met Gly Ser Glu Val Asn Arg Pro Leu Ala Asp Phe Pro Ala Asn Ile
1               5                   10                  15

Trp Glu Asp Pro Leu Thr Ser Phe Ser Lys Ser Asp Leu Gly Thr Glu
            20                  25                  30

Thr Phe Lys Glu Lys His Ser Thr Leu Lys Glu Ala Val Lys Glu Ala
        35                  40                  45

Phe Met Ser Ser Lys Ala Asn Pro Ile Glu Asn Ile Lys Phe Ile Asp
    50                  55                  60

Ala Leu Cys Arg Leu Gly Val Ser Cys His Phe Glu Lys Asp Ile Val
65                  70                  75                  80

Glu Gln Leu Asp Lys Ser Phe Asp Cys Leu Asp Phe Pro Gln Met Val
                85                  90                  95

Arg Gln Glu Gly Cys Asp Leu Tyr Thr Val Gly Ile Ile Phe Gln Val
            100                 105                 110

Phe Arg Gln Phe Gly Phe Lys Leu Ser Ala Asp Val Phe Glu Lys Phe
        115                 120                 125

Lys Asp Glu Asn Gly Lys Phe Lys Gly His Leu Val Thr Asp Ala Tyr
    130                 135                 140
```

```
Gly Met Leu Ser Leu Tyr Glu Ala Ala Gln Trp Gly Thr His Gly Glu
145                 150                 155                 160

Asp Ile Ile Asp Glu Ala Leu Ala Phe Ser Arg Ser His Leu Glu Glu
                165                 170                 175

Ile Ser Ser Arg Ser Ser Pro His Leu Ala Ile Arg Ile Lys Asn Ala
                180                 185                 190

Leu Lys His Pro Tyr His Lys Gly Ile Ser Arg Ile Glu Thr Arg Gln
            195                 200                 205

Tyr Ile Ser Tyr Tyr Glu Glu Glu Ser Cys Asp Pro Thr Leu Leu
210                 215                 220

Glu Phe Ala Lys Ile Asp Phe Asn Leu Leu Gln Ile Leu His Arg Glu
225                 230                 235                 240

Glu Leu Ala Cys Val Thr Arg Trp His His Glu Met Glu Phe Lys Ser
                245                 250                 255

Lys Val Thr Tyr Thr Arg His Arg Ile Thr Glu Ala Tyr Leu Trp Ser
                260                 265                 270

Leu Gly Thr Tyr Phe Glu Pro Gln Tyr Ser Gln Ala Arg Val Ile Thr
            275                 280                 285

Thr Met Ala Leu Ile Leu Phe Thr Ala Leu Asp Asp Met Tyr Asp Ala
290                 295                 300

Tyr Gly Thr Met Glu Glu Leu Glu Leu Phe Thr Asp Ala Met Asp Glu
305                 310                 315                 320

Trp Leu Pro Val Val Pro Asp Glu Ile Pro Ile Pro Asp Ser Met Lys
                325                 330                 335

Phe Ile Tyr Asn Val Thr Val Glu Phe Tyr Asp Lys Leu Asp Glu Glu
                340                 345                 350

Leu Glu Lys Glu Gly Arg Ser Gly Cys Gly Phe His Leu Lys Lys Ser
            355                 360                 365

Leu Gln Lys Thr Ala Asn Gly Tyr Met Gln Glu Ala Lys Trp Leu Lys
            370                 375                 380

Lys Asp Tyr Ile Ala Thr Phe Asp Glu Tyr Lys Glu Asn Ala Ile Leu
385                 390                 395                 400

Ser Ser Gly Tyr Tyr Gly Leu Ile Ala Met Thr Phe Val Arg Met Thr
                405                 410                 415

Asp Val Ala Lys Leu Asp Ala Phe Glu Trp Leu Asn Ser His Pro Lys
                420                 425                 430

Ile Arg Val Ala Ser Glu Ile Ile Ser Arg Phe Thr Asp Asp Ile Ser
            435                 440                 445

Ser Tyr Glu Phe Glu His Lys Arg Glu His Val Ala Thr Gly Ile Asp
            450                 455                 460

Cys Tyr Met Gln Gln Phe Gly Val Ser Lys Glu Arg Ala Val Glu Val
465                 470                 475                 480

Met Gly Asn Ile Val Ser Asp Ala Trp Lys Asp Leu Asn Gln Glu Leu
                485                 490                 495

Met Arg Pro His Val Phe Pro Phe Leu Leu Met Arg Val Leu Asn
                500                 505                 510

Leu Ser Arg Val Ile Asp Val Phe Tyr Arg Tyr Gln Asp Ala Tyr Thr
            515                 520                 525

Asn Pro Lys Leu Leu Lys Glu His Ile Val Ser Leu Leu Ile Glu Thr
            530                 535                 540

Ile Pro Ile
545
```

<210> SEQ ID NO 22
<211> LENGTH: 547
<212> TYPE: PRT
<213> ORGANISM: Zea mays

<400> SEQUENCE: 22

```
Met Ala Ala Asp Glu Ala Arg Ser Val Ser Arg Leu His Ser Glu Glu
1               5                   10                  15

Asp Met His Gly Lys His His Ser Thr Leu Trp Gly Asp Phe Phe Leu
            20                  25                  30

His His Val Pro Cys Arg Pro Gly Gln Tyr Ser Ile Met Lys Asp Asn
        35                  40                  45

Val Lys Ile Met Lys Glu Glu Val Lys Lys Met Leu Leu Asp Val Gly
50                  55                  60

Ser Ser Asp Leu Ser His Lys Leu Glu Cys Ile Asp Thr Leu Glu Arg
65                  70                  75                  80

Leu Gly Leu Asp Tyr His Tyr Thr Lys Glu Ile Asp Glu Leu Met Cys
                85                  90                  95

Asn Val Phe Glu Ala Arg Asp Gln Asp Leu Asp Leu Thr Thr Thr Ser
            100                 105                 110

Gln Leu Phe Tyr Leu Leu Arg Lys His Gly Tyr His Val Ser Ser Asp
        115                 120                 125

Val Phe Leu Lys Phe Gly Asp Asp Lys Gly Asp Ile Val Thr Asp Asp
130                 135                 140

Ala Arg Cys Leu Leu Arg Met Tyr Glu Ala Ala His Val Arg Val Asn
145                 150                 155                 160

Gly Glu Glu Ile Leu Asp Asn Ile Leu Ile His Thr Lys Arg Gln Leu
                165                 170                 175

Gln Cys Ile Val Asp Asp Leu Glu Pro Thr Leu Gln Glu Val Arg
            180                 185                 190

Tyr Ala Leu Glu Thr Pro Leu Phe Arg Arg Leu Asn Arg Val Gln Ala
        195                 200                 205

Arg Gln Phe Ile Ser Thr Tyr Glu Lys Ser Thr Met Arg Asn Asn Met
210                 215                 220

Leu Leu Glu Phe Ser Lys Leu Asp Phe Asn Ile Leu Leu Thr Leu Tyr
225                 230                 235                 240

Cys Glu Glu Leu Lys Asp Leu Thr Met Trp Trp Lys Glu Phe Gln Ala
                245                 250                 255

Gln Ala Asn Thr Thr Ile Tyr Ala Arg Asp Arg Met Val Glu Met His
            260                 265                 270

Phe Trp Met Met Gly Val Phe Phe Glu Pro Gln Tyr Ser Tyr Ser Arg
        275                 280                 285

Lys Met Leu Thr Gln Leu Phe Met Ile Val Ser Val Leu Asp Asp Leu
290                 295                 300

Tyr Asp Ser His Cys Thr Thr Glu Glu Gly Asn Ala Phe Thr Ala Ala
305                 310                 315                 320

Leu Gln Arg Trp Asp Glu Gly Val Glu Gln Cys Pro Thr Tyr Leu
                325                 330                 335

Arg Thr Leu Tyr Thr Asn Ile Arg Ala Thr Val Lys Ala Ile Glu Glu
            340                 345                 350

Asp Leu Asn Leu Gln Asn Asn Lys His Ala Lys Leu Val Lys Gly Leu
        355                 360                 365

Ile Ile Asp Met Ala Met Cys Tyr Asn Ala Glu Thr Glu Trp Arg Asp
370                 375                 380
```

-continued

```
Lys Lys Tyr Val Pro Ala Thr Val Asp Glu His Leu Lys Ile Ser Ala
385                 390                 395                 400

Arg Ser Ser Gly Cys Met His Leu Val Ser Gln Gly Phe Ile Ser Met
            405                 410                 415

Gly Asp Val Ala Thr Ser Glu Ala Leu Glu Trp Ala Ser Thr Tyr Pro
        420                 425                 430

Lys Ile Val Arg Ala Val Cys Ile Ile Ala Arg Leu Ala Asn Asp Ile
    435                 440                 445

Met Ser Tyr Lys Arg Glu Ala Ser Asn Asn Thr Met Val Ser Thr Val
450                 455                 460

Gln Thr Cys Ala Lys Glu Tyr Gly Thr Thr Thr Val Glu Gln Ala Ile
465                 470                 475                 480

Glu Lys Ile Arg Glu Leu Ile Glu Glu Ala Trp Met Asp Ile Thr His
            485                 490                 495

Glu Cys Leu Arg Gln Pro Gln Pro Met Ala Leu Leu Glu Arg Ala Val
        500                 505                 510

Asn Leu Ala Arg Thr Met Asp Phe Leu Tyr Lys Asp Val Asp Gly Tyr
    515                 520                 525

Thr Asp Ser Trp Ser Ile Lys Gly Ile Leu Asp Ser Leu Tyr Val His
530                 535                 540

Leu Ile Asp
545

<210> SEQ ID NO 23
<211> LENGTH: 576
<212> TYPE: PRT
<213> ORGANISM: Oryza sativa

<400> SEQUENCE: 23

Met Ala Thr Ser Val Pro Ser Val Leu Leu Leu Pro Val Pro Thr Cys
1               5                   10                  15

Thr Asp Met Leu Val Ser Pro Val Glu Gly Gly Asp Leu Leu His Cys
            20                  25                  30

Lys Pro His Phe Asp His His Pro Asn Val Trp Gly Asp Tyr Phe Leu
        35                  40                  45

Thr Phe Ser Pro Cys Thr Pro Ser Met Leu Leu Asn Met Lys Arg Lys
    50                  55                  60

Ala His Val Ser Glu Glu Gln Val Arg Arg Met Ile Leu Glu Cys Ser
65                  70                  75                  80

Ser Gly Pro Asn Leu His Val Lys Leu Glu Leu Val Asp Thr Leu Glu
            85                  90                  95

Arg Leu Cys Ile Asp Tyr His Tyr Glu Lys Glu Ile Glu Asn Val Leu
        100                 105                 110

Arg Arg Val His Glu Glu Asp Thr Asp Asn His Tyr Asp Leu
    115                 120                 125

His Thr Thr Ala Leu Arg Phe Tyr Leu Leu Arg Lys His Gly Tyr Tyr
130                 135                 140

Ala Ser Pro Asp Val Phe Gln Arg Phe Arg Asp Glu Glu Gly Asn Phe
145                 150                 155                 160

Thr Arg Asp Asp Asn Asn Gly Thr Arg Ser Met Leu Ser Leu Tyr
            165                 170                 175

Asn Ala Ala His Leu Arg Ile His Gly Glu Glu Ile Leu Asp Asp Ala
        180                 185                 190

Ile Val Phe Thr Arg Asn Tyr Leu Gln Ser Val Val Lys His Leu Gln
```

```
                195                 200                 205
Ser Pro Met Ala Asp Glu Val Cys Ser Ala Leu Arg Thr Pro Leu Phe
210                 215                 220

Arg Arg Pro Arg Val Glu Ala Arg His Tyr Ile Ser Val Tyr Asp
225                 230                 235                 240

Lys Leu Pro Thr Arg Asn Glu Thr Ile Leu Glu Phe Ala Lys Leu Asp
                245                 250                 255

Phe Gly Ile Leu Gln Ser Leu Tyr Cys Glu Glu Leu Asn Ile Leu Thr
                260                 265                 270

Met Trp Trp Lys Glu Leu Gln Leu Gln Asp His Leu Ser Phe Ala Arg
            275                 280                 285

Asp Arg Met Val Glu Met His Phe Trp Met Leu Gly Val Leu Phe Glu
        290                 295                 300

Pro Gln Tyr Ser Tyr Gly Arg Thr Met Leu Thr Lys Leu Phe Ile Phe
305                 310                 315                 320

Val Ser Ile Phe Asp Asp Ile Tyr Asp Asn Tyr Ser Thr Leu Glu Glu
                325                 330                 335

Ser Lys Leu Phe Thr Glu Ala Ile Glu Arg Trp Asp Glu Glu Ala Ala
                340                 345                 350

Glu Glu Leu Pro Gly Tyr Met Lys Phe Phe Tyr Lys Lys Val Leu Thr
            355                 360                 365

Thr Met Lys Ser Ile Glu Thr Asp Leu Lys Leu Gln Gly Asn Lys His
        370                 375                 380

Val Asp Tyr Val Lys Asn Leu Leu Ile Asp Ala Thr Arg Cys Phe Tyr
385                 390                 395                 400

Asn Glu Val Lys Trp Arg Ser Glu Gly Ala Asp Gln Val Ala Ala Thr
                405                 410                 415

Val Glu Glu His Leu Lys Ile Ser Val Pro Ser Ser Cys Cys Met His
                420                 425                 430

Val Pro Val Tyr Ala Phe Val Ala Met Gly Asn Asp Val Thr Thr Asp
            435                 440                 445

Asp Ala Ile Asn Trp Gly Met Ala Tyr Pro Lys Ile Ile Thr Ser Ser
        450                 455                 460

Cys Ile Val Gly Arg Leu Leu Asn Asp Ile Ala Ser His Glu Arg Glu
465                 470                 475                 480

Gln Gly Ser Ser Ser Ser Ser Ser Thr Val Glu Ala Cys Met Arg
                485                 490                 495

Glu His Gly Gly Ile Thr Lys Glu Ala Tyr Ala Lys Leu Arg Glu
                500                 505                 510

Leu Val Glu Glu Ser Trp Met Asp Ile Ala Gly Glu Cys Leu Arg Pro
            515                 520                 525

Ala Ala Ala Gln Pro Pro Leu Leu Glu Ala Val Asn Ala Thr
        530                 535                 540

Arg Val Leu Asp Phe Val Tyr Lys Asp Gln Asp Ala Tyr Thr His
545                 550                 555                 560

Pro Ser Ser Leu Lys Asp Thr Ile His Ser Ile Tyr Ile Leu Ser Val
                565                 570                 575

<210> SEQ ID NO 24
<211> LENGTH: 560
<212> TYPE: PRT
<213> ORGANISM: Citrus junos

<400> SEQUENCE: 24
```

```
Met Lys Asp Met Ser Ile Pro Leu Leu Ala Val Ser Ser Thr
1               5                   10                  15

Glu Glu Thr Val Arg Pro Ile Ala Asp Phe His Pro Thr Leu Trp Gly
            20                  25                  30

Asn His Phe Leu Lys Ser Ala Ala Asp Val Glu Thr Ile Asp Ala Ala
        35                  40                  45

Thr Gln Glu Gln His Ala Ala Leu Lys Gln Glu Val Arg Arg Met Ile
    50                  55                  60

Thr Thr Thr Ala Asn Lys Leu Ala Gln Lys Leu His Met Ile Asp Ala
65              70                  75                  80

Val Gln Arg Leu Gly Val Ala Tyr His Phe Glu Lys Glu Ile Glu Asp
                85                  90                  95

Glu Leu Gly Lys Val Ser His Asp Leu Asp Ser Asp Leu Tyr Val
            100                 105                 110

Val Ser Leu Arg Phe Arg Leu Phe Arg Gln Gln Gly Val Lys Ile Ser
            115                 120                 125

Cys Asp Val Phe Asp Lys Phe Asp Asp Glu Gly Lys Phe Lys Glu
    130                 135                 140

Ser Leu Ile Asn Asp Ile Arg Gly Met Leu Ser Leu Tyr Glu Ala Ala
145             150                 155                 160

Tyr Leu Ala Ile Arg Gly Glu Asp Ile Leu Asp Glu Ala Ile Val Phe
                165                 170                 175

Thr Thr Thr His Leu Lys Ser Val Ile Ser Ile Ser Asp His Ser His
            180                 185                 190

Ala Asn Ser Asn Leu Ala Glu Gln Ile Arg His Ser Leu Gln Ile Pro
    195                 200                 205

Leu Arg Lys Ala Ala Ala Arg Leu Glu Ala Arg Tyr Phe Leu Asp Ile
    210                 215                 220

Tyr Ser Arg Asp Asp Leu His Asp Glu Thr Leu Leu Lys Phe Ala Lys
225                 230                 235                 240

Leu Asp Phe Asn Ile Leu Gln Ala Ala His Gln Lys Glu Ala Ser Ile
                245                 250                 255

Met Thr Arg Trp Trp Asn Asp Leu Gly Phe Pro Lys Lys Val Pro Tyr
            260                 265                 270

Ala Arg Asp Arg Ile Ile Glu Thr Tyr Ile Trp Met Leu Leu Gly Val
    275                 280                 285

Ser Tyr Glu Pro Asn Leu Ala Phe Gly Arg Ile Phe Ala Ser Lys Val
    290                 295                 300

Val Cys Met Ile Thr Thr Ile Asp Asp Thr Phe Asp Ala Tyr Gly Thr
305                 310                 315                 320

Phe Glu Glu Leu Thr Leu Phe Thr Glu Ala Val Thr Arg Trp Asp Ile
                325                 330                 335

Gly Leu Ile Asp Thr Leu Pro Glu Tyr Met Lys Phe Ile Val Lys Ala
            340                 345                 350

Leu Leu Asp Ile Tyr Arg Glu Ala Glu Glu Leu Ala Lys Glu Gly
            355                 360                 365

Arg Ser Tyr Gly Ile Pro Tyr Ala Lys Gln Met Met Gln Glu Leu Ile
    370                 375                 380

Ile Leu Tyr Phe Thr Glu Ala Lys Trp Leu Tyr Lys Gly Tyr Val Pro
385                 390                 395                 400

Thr Phe Asp Glu Tyr Lys Ser Val Ala Leu Arg Ser Ile Gly Leu Arg
                405                 410                 415

Thr Leu Ala Val Ala Ser Phe Val Asp Leu Gly Asp Phe Ile Ala Thr
```

```
            420                 425                 430
Lys Asp Asn Phe Glu Cys Ile Leu Lys Asn Ala Lys Ser Leu Lys Ala
                435                 440                 445

Thr Glu Thr Ile Gly Arg Leu Met Asp Asp Ile Ala Gly Tyr Lys Phe
            450                 455                 460

Glu Gln Lys Arg Gly His Asn Pro Ser Ala Val Glu Cys Tyr Lys Asn
465                 470                 475                 480

Gln His Gly Val Ser Glu Glu Ala Val Lys Glu Leu Leu Leu Glu
                    485                 490                 495

Val Ala Asn Ser Trp Lys Asp Ile Asn Glu Glu Leu Leu Asn Pro Thr
                500                 505                 510

Thr Val Pro Leu Pro Met Leu Gln Arg Leu Leu Tyr Phe Ala Arg Ser
            515                 520                 525

Gly His Phe Ile Tyr Asp Asp Gly His Asp Arg Tyr Thr His Ser Leu
            530                 535                 540

Met Met Lys Arg Gln Val Ala Leu Leu Leu Thr Glu Pro Leu Ala Ile
545                 550                 555                 560

<210> SEQ ID NO 25
<211> LENGTH: 555
<212> TYPE: PRT
<213> ORGANISM: Citrus junos

<400> SEQUENCE: 25

Met Ser Ala Gln Val Leu Ala Thr Val Ser Ser Thr Glu Lys Thr
1               5                   10                  15

Val Arg Pro Ile Ala Gly Phe His Pro Asn Leu Trp Gly Asp Tyr Phe
                20                  25                  30

Leu Thr Leu Ala Ser Asp Cys Lys Thr Asp Thr Thr His Gln Glu
            35                  40                  45

Glu Tyr Glu Ala Leu Lys Gln Glu Val Arg Ser Met Ile Thr Ala Thr
        50                  55                  60

Ala Asp Thr Pro Ala Gln Lys Leu Gln Leu Val Asp Ala Val Gln Arg
65                  70                  75                  80

Leu Gly Val Ala Tyr His Phe Glu Gln Glu Ile Glu Asp Ala Met Glu
                85                  90                  95

Lys Ile Tyr His Asp Asp Phe Asp Asn Asn Asp Val Asp Leu Tyr
            100                 105                 110

Thr Val Ser Leu Arg Phe Arg Leu Leu Arg Gln Gln Gly Phe Lys Val
        115                 120                 125

Pro Cys Asp Val Phe Ala Lys Phe Lys Asp Glu Gly Lys Phe Lys
    130                 135                 140

Ala Ser Leu Val Arg Asp Val His Gly Ile Leu Ser Leu Tyr Glu Ala
145                 150                 155                 160

Gly His Leu Ala Ile Arg Gly Glu Gly Ile Leu Asp Glu Ala Ile Ala
                165                 170                 175

Phe Thr Arg Thr His Leu Gln Ser Met Val Ser Gln Asp Val Cys Pro
            180                 185                 190

Asn Asn Leu Ala Glu Gln Ile Asn His Thr Leu Asp Cys Pro Leu Arg
        195                 200                 205

Arg Ala Leu Pro Arg Val Glu Thr Arg Phe Phe Leu Ser Val Tyr Pro
    210                 215                 220

Arg Asp Asp Lys His Asp Lys Thr Leu Leu Lys Phe Ser Lys Leu Asp
225                 230                 235                 240
```

```
Phe Asn Leu Val Gln Arg Ile His Gln Lys Glu Leu Ser Ala Ile Thr
                245                 250                 255

Arg Trp Trp Lys Asp Leu Asp Phe Thr Thr Lys Leu Pro Tyr Ala Arg
            260                 265                 270

Asp Arg Ile Val Glu Leu Tyr Phe Trp Ile Val Gly Thr Tyr Phe Glu
        275                 280                 285

Pro Lys Tyr Thr Leu Ala Arg Lys Ile Met Thr Lys Thr Ile Tyr Thr
    290                 295                 300

Ala Ser Ile Ile Asp Asp Thr Phe Asp Ala Tyr Gly Phe Phe Glu Glu
305                 310                 315                 320

Leu Lys Leu Phe Ala Glu Ala Val Gln Arg Trp Asp Ile Gly Ala Met
                325                 330                 335

Asp Ile Leu Pro Glu Tyr Met Lys Val Leu Tyr Lys Ala Leu Leu Asp
            340                 345                 350

Thr Phe Asn Glu Ile Glu Gln Asp Leu Ala Lys Glu Gly Arg Ser Ser
        355                 360                 365

Cys Leu Pro Tyr Gly Lys Glu Lys Met Gln Glu Leu Val Gln Met Tyr
    370                 375                 380

Phe Val Gln Ala Lys Trp Phe Ser Glu Gly Tyr Val Pro Thr Trp Asp
385                 390                 395                 400

Glu Tyr Tyr Pro Val Gly Leu Val Ser Cys Gly Tyr Phe Met Leu Ala
                405                 410                 415

Thr Asn Ser Phe Leu Gly Met Cys Asp Val Ala Asn Lys Glu Ser Phe
            420                 425                 430

Glu Trp Ile Ser Arg Thr Leu Arg Phe Gln Gln Arg His Gln Phe Ile
        435                 440                 445

Cys Arg Leu Arg Asn Asp Ile Val Ser His Gln Phe Glu Gln Lys Arg
    450                 455                 460

Gly His Ile Ala Ser Gly Val Glu Cys Tyr Ile Lys Gln Tyr Gly Val
465                 470                 475                 480

Ser Ala Glu Glu Val Val Thr Val Phe Thr Glu Val Glu Asn Ala
                485                 490                 495

Trp Lys Asp Met Asn Glu Glu Phe Leu Lys Pro Thr Ala Phe Pro Val
            500                 505                 510

Ala Leu Ile Glu Arg Pro Phe Asn Ile Ala Arg Val Ile Glu Phe Leu
        515                 520                 525

Asn Lys Lys Gly Asp Trp Tyr Thr His Ser His Ala Ile Lys Asp Gln
    530                 535                 540

Ile Ala Ala Val Leu Arg Asp Pro Val Thr Ile
545                 550                 555

<210> SEQ ID NO 26
<211> LENGTH: 548
<212> TYPE: PRT
<213> ORGANISM: Citrus paradisi

<400> SEQUENCE: 26

Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60
```

```
Leu Ile Asp Glu Val Gln Arg Leu Gly Val Ala Tyr His Phe Glu Lys
 65                  70                  75                  80

Glu Ile Glu Asp Ala Ile Leu Lys Leu Cys Pro Ile Tyr Ile Asp Ser
                 85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
            115                 120                 125

Asp Glu Gly Arg Phe Lys Ser Ser Leu Ile Asn Asp Val Gln Gly Met
            130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
            195                 200                 205

Phe Met Ser Met Ile Asn Ser Thr Ser Asp His Leu Tyr Asn Lys Thr
210                 215                 220

Leu Leu Asn Phe Ala Lys Leu Asp Phe Asn Ile Leu Leu Glu Pro His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
            275                 280                 285

Ile Met Thr Gln Leu Asn Tyr Ile Leu Ser Ile Ile Asp Asp Thr Tyr
            290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
            355                 360                 365

Asn Gln Lys Val Ile Gly Ala Tyr Ser Val Gln Ala Lys Trp Phe Ser
            370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
            435                 440                 445

Gly His Glu Phe Glu Gln Lys Arg Gly His Val Ala Ser Ala Ile Glu
            450                 455                 460

Cys Tyr Thr Lys Gln His Gly Val Ser Lys Glu Glu Ala Ile Lys Met
465                 470                 475                 480
```

Phe Glu Glu Glu Val Ala Asn Ala Trp Lys Asp Ile Asp Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
            515                 520                 525

Thr His Ser Tyr Leu Ile Lys Asp Gln Ile Ala Ser Val Leu Gly Asp
            530                 535                 540

His Val Pro Phe
545

<210> SEQ ID NO 27
<211> LENGTH: 1224
<212> TYPE: DNA
<213> ORGANISM: Arabidopsis thaliana

<400> SEQUENCE: 27
agtaatttag ctgagaagtc ttggtgggag tctctatcgt cgtcgtatcc aaagctcttc      60
aatggagacc gatctcaagt caaccttct caacgtttat tctgttctca gtctgacct      120 tcttcatgac ccttccttcg aattcaccaa tgaatctcgt ctctggggtg atcggatgct      180
ggactacaat gtacgtggag ggaaactcaa tcggggtctc tctgttgttg acagtttcaa      240
acttttgaag caaggcaatg atttgactga gcaagaggtc ttcctctctt gtgctctcgg      300
ttggtgcatt gaatggctcc aagcttattt ccttgtgctt gatgacatta tggataactc      360
tgtcacccgc cgtggtcaac cttgctggtt cagagttcct caggttggta tggttgccat      420
caatgatggg attctacttc gcaatcacat ccacaggatt ctcaaaaagc atttccgtga      480
taagccttac tatgttgacc ttgttgattt gtttaatgag gttgagttgc aaacagcttg      540
tggccagatg atagatttga tcaccacctt tgaaggcgaa aaggatttgt ccaagtactc      600
attgtcaatc caccgtcgta ttgtccagca caaaacggct tattactcat tttatctccc      660
tgttgcttgt gcgttgctta tggcgggcga aaatttggaa aaccatattg acgtgaaaaa      720
tgttcttgtt gacatgggaa tctacttcca agtgcaggat gattatctgg attgttttgc      780
tgatcccgag acgcttggca agatagggaac agatatagaa gatttcaaat gctcttggtt      840
ggtggttaag gcattagaac gctgcagcga agaacaaact aagatattat atgagaacta      900
tggtaaaacc gacccatcga acgttgctaa agtgaaggat ctctacaaag agctggatct      960
tgagggagtg ttcatggagt atgagagcaa aagctacgag aagctgactg gagcgattga      1020
gggacaccaa agtaaagcaa tccaagcagt gctaaaatcc ttcttggcta agatctacaa      1080
gaggcagaag tagtagagac agacaaacat aagtctcagc cctcaaaaat ttcctgttat      1140
gtctttgatt cttggttggt gatttgtgta attctgttaa gtgctctgat tttcaggggg      1200
aataataaac ctgcctcact ctgt      1224

<210> SEQ ID NO 28
<211> LENGTH: 343
<212> TYPE: PRT
<213> ORGANISM: Arabidopsis thaliana

<400> SEQUENCE: 28

Met Glu Thr Asp Leu Lys Ser Thr Phe Leu Asn Val Tyr Ser Val Leu
1               5                   10                  15

Lys Ser Asp Leu Leu His Asp Pro Ser Phe Glu Phe Thr Asn Glu Ser
            20                  25                  30

-continued

```
Arg Leu Trp Val Asp Arg Met Leu Asp Tyr Asn Val Arg Gly Gly Lys
        35                  40                  45

Leu Asn Arg Gly Leu Ser Val Val Asp Ser Phe Lys Leu Leu Lys Gln
 50                  55                  60

Gly Asn Asp Leu Thr Glu Gln Glu Val Phe Leu Ser Cys Ala Leu Gly
 65                  70                  75                  80

Trp Cys Ile Glu Trp Leu Gln Ala Tyr Phe Leu Val Leu Asp Asp Ile
                 85                  90                  95

Met Asp Asn Ser Val Thr Arg Arg Gly Gln Pro Cys Trp Phe Arg Val
               100                 105             110

Pro Gln Val Gly Met Val Ala Ile Asn Asp Gly Ile Leu Leu Arg Asn
             115                 120                 125

His Ile His Arg Ile Leu Lys Lys His Phe Arg Asp Lys Pro Tyr Tyr
             130                 135             140

Val Asp Leu Val Asp Leu Phe Asn Glu Val Glu Leu Gln Thr Ala Cys
145                 150                 155                 160

Gly Gln Met Ile Asp Leu Ile Thr Thr Phe Glu Gly Glu Lys Asp Leu
                165                 170             175

Ser Lys Tyr Ser Leu Ser Ile His Arg Arg Ile Val Gln His Lys Thr
            180                 185             190

Ala Tyr Tyr Ser Phe Tyr Leu Pro Val Ala Cys Ala Leu Leu Met Ala
        195                 200             205

Gly Glu Asn Leu Glu Asn His Ile Asp Val Lys Asn Val Leu Val Asp
        210             215             220

Met Gly Ile Tyr Phe Gln Val Gln Asp Asp Tyr Leu Asp Cys Phe Ala
225                 230                 235             240

Asp Pro Glu Thr Leu Gly Lys Ile Gly Thr Asp Ile Glu Asp Phe Lys
                245             250             255

Cys Ser Trp Leu Val Val Lys Ala Leu Glu Arg Cys Ser Glu Glu Gln
                260             265             270

Thr Lys Ile Leu Tyr Glu Asn Tyr Gly Lys Thr Asp Pro Ser Asn Val
            275             280             285

Ala Lys Val Lys Asp Leu Tyr Lys Glu Leu Asp Leu Glu Gly Val Phe
290                 295                 300

Met Glu Tyr Glu Ser Lys Ser Tyr Glu Lys Leu Thr Gly Ala Ile Glu
305                 310             315                 320

Gly His Gln Ser Lys Ala Ile Gln Ala Val Leu Lys Ser Phe Leu Ala
            325                 330             335

Lys Ile Tyr Lys Arg Gln Lys
            340
```

REPELLENT COMPOSITIONS AND GENETIC APPROACHES FOR CONTROLLING HUANGLONGBING

CROSS-REFERENCE TO RELATED APPLICATIONS

This application is a continuation of U.S. patent application Ser. No. 13/501,739 filed Apr. 12, 2012, now U.S. Pat. No. 9,078,448, which is a 371 filing of International patent application no. PCT/BR2010/000353 filed Oct. 26, 2010, which claims the benefit of U.S. provisional application No. 61/255,705 filed Oct. 28, 2009, the entire content of each of which are expressly incorporated herein by reference thereto.

FIELD OF INVENTION

The invention relates to repellent compositions comprising sesquiterpenes to control Huanglongbing (HLB) in citrus plants. Methods for controlling HLB through genetic modification of citrus plants are also disclosed.

BACKGROUND OF THE INVENTION

Huanglongbing (HLB), also known as citrus vein phloem degeneration (CVPD), citrus greening disease, yellow shoot disease (translated from Chinese huang-lunpin), likubin in Taiwan (translated from Chinese as Immediate Withering Disease), leaf mottle yellows in the Philippines, and citrus dieback in India, is probably the worst disease of citrus caused by a vectored pathogen. The causative agent is a motile bacterium, *Candidatus* Liberibacter spp., which is transmitted by Asian citrus psyllids (*Sternorrhyncha: Psyllidae*), also known as *Diaphorina citri* or, in Africa, by *Trioza erytreae*, the African citrus psyllid.

Distribution of HLB is primarily in tropical and subtropical Asia. It has been reported in all citrus-growing regions in Asia. The disease has affected crops in China, Taiwan, India, Sri Lanka, Malaysia, Indonesia, Myanmar, the Philippines, Pakistan, Thailand, the Ryukyu Islands, Nepal, Réunion, Mauritius, and Afghanistan. Areas outside Asia such as Saudi Arabia, Brazil and Florida in the U.S. have also reported the disease.

Although existing insecticidal and repellent compositions may be useful in controlling HLB, the safety of these compositions has been questioned as many of these compositions are excessively toxic to other organisms in the ecosystem. In addition, many of these compositions are extraordinarily long-lived, and persist within the environment to which they are applied almost indefinitely. Moreover, many insect species have evolved resistance to many of the known insecticidal and repellent compositions. Thus, a need exists for a relatively non-toxic, shorter-lived, effective repellent composition, such as a biological repellent composition.

It is long known in Vietnam that guava grown in proximity to or intercropped with citrus has a protectant or repellant effect against the Asian citrus psyllid. Guavas are plants in the myrtle family (Myrtaceae) genus *Psidium*, which contains about 100 species of tropical shrubs and small trees. The most frequently-encountered species, and the one often simply referred to as "the guava," is the Apple Guava (*Psidium guajava*).

The protective effect of interplanting guava and citrus is likely due to volatiles produced from the guava leaves because the protective effect is present year round. Although fifty-seven components including 27 terpenes (or sesquiterpenes) along with 14 alcohols and 4 esters have been identified in guava leaf oil using Gas Chromatography-Mass Spectrometry (GC-MS) obtained from a hydrodistillation of guava leaves, the exact mechanism underlying the protective effect of guava is not known. A recent report (Rouseff et al., "Sulfur Volatiles in Guava (*Psidium guajava* L.) Leaves: Possible Defense Mechanism", J. Agric. Food Chem, 56:8905-10, 2008) suggests that sulfur volatiles such as dimethyl disulfide are responsible for the repulsive effect of guava, not the major volatiles such as β-caryophyllene since the latter is also present in citrus. However, sulfur volatiles contained in guava leaves are emitted at tiny levels and only for a period of about 30 minutes after wounding, indicating that these compounds have nothing or little to do with what is observed in citrus-guava intercroppings in Vietnam. On the other hand, β-caryophyllene is present in undamaged citrus leaves at concentrations generally below 0.2% of total volatiles, while it represents usually more than 50% of total volatiles emitted by guava leaves.

There remains a need, for controlling HLB in citrus plants, and the present embodiments of the invention provide a novel solution to this problem.

SUMMARY OF THE INVENTION

It has been found that sesquiterpenes such as β-caryophyllene and α-copaene produced from the guava leaves repel *Diaphorina citri* and/or *Tryoza erytrae* psyllid insects. Thus, the invention satisfies a need of the industry for controlling HLB in citrus plants by providing a biological repellent composition comprising sesquiterpenes. Methods for controlling HLB through genetic modification of citrus plants to over-express genes coding sesquiterpene synthases are also provided.

Thus, the invention relates in general to a method for controlling HLB in citrus plants, which comprises expressing at least one gene encoding a polypeptide having sesquiterpene synthase activity in citrus plants to produce additional sesquiterpenes in order to repel *Diaphorina citri* and/or *Tryoza erytrae* psyllid insects so as to control HLB, wherein the sesquiterpene over-accumulated is β-caryophyllene, α-copaene, or combinations thereof. In this method, the at least one gene has β-caryophyllene synthase and/or α-copaene synthase activity.

In certain embodiments, the expression of the at least one gene is driven by its own promoter and terminator regions. In other preferred embodiments, the expression of the at least one gene is driven by a heterologous regulator region providing strong constitutive, tissue-specific or inducible expression. More preferably, the heterologous regulator region provides strong tissue-specific expression in the cytosol, chloroplasts or mitochondria.

In additional embodiments, the present method further comprises expressing a gene encoding a farnesyl pyrophosphase synthase to enhance the accumulation of the sesquiterpene produced by the polypeptide having sesquiterpene synthase activity.

The invention also relates to a method for controlling Huanglongbing (HLB) disease of citrus plants comprising applying at least one purified sesquiterpene, which repels *Diaphorina citri* and/or *Tryoza erytrae* psyllid insects, so as to control the HLB disease of citrus plants, wherein the at least one sesquiterpene is selected from the group consisting of β-caryophyllene and α-copaene, or combinations thereof. In this method, the at least one purified sesquiterpene is purified from an organism selected from the group consisting of plants, bacteria and yeasts. In a preferred embodiment, the at least one purified sesquiterpene is purified from the guava plant, preferably, the leave extracts of the guava plant.

In some preferred embodiments, the at least one sesquiterpene is applied to the citrus plants through slow delivery systems as those already used by entomologists to deliver pheromones.

BRIEF DESCRIPTION OF THE FIGURES

FIGS. 1A and B show the nucleotide sequences of SEQ ID NOs:1 and 3, and protein sequences of SEQ ID NOs:2 and 4.

FIG. 7 shows alignments of the amino acid sequences of beta-caryophyllene synthase QHS1 from *Artemisia annua* (Accession No. AAL79181) (SEQ ID NO: 18), beta-caryophyllene synthase from *Mikania micrantha* (Accession No. ACN67535) (SEQ ID NO: 19), beta-caryophyllene synthase from *Cucumis sativus* (Accession No. AAU05952) (SEQ ID NO: 20), beta-caryophyllene/alpha-humulene synthase from *Arabidopsis thaliana* (Accession No. AAO85539) (SEQ ID NO: 21), (E)-beta-caryophyllene synthase from *Zea mays* (Accession No. ABY79206) (SEQ ID NO: 22) and (E)-beta-caryophyllene/beta-elemene synthase from *Oryza sativa* (Accession No. ABJ16553) (SEQ ID NO: 23). Highlighted in black and highlighted in gray are respectively identical and similar residues in these sequences.

FIG. 8 shows (A) alignments of the amino acid sequences of beta-caryophyllene synthase QHS1 from *Artemisia annua* (Accession No. AAL79181) (SEQ ID NO: 18), beta-caryophyllene synthase from *Mikania micrantha* (Accession No. ACN67535) (SEQ ID NO: 19), beta-caryophyllene synthase from *Cucumis sativus* (Accession No. AAU05952) (SEQ ID NO: 20), and beta-caryophyllene/alpha-humulene synthase from *Arabidopsis thaliana* (Accession No. AAO85539) (SEQ ID NO: 21), and (B) alignments of the amino acid sequences of (E)-beta-caryophyllene synthase from *Zea mays* (Accession No. ABY79206) (SEQ ID NO: 22) and (E)-beta-caryophyllene/beta-elemene synthase from *Oryza sativa* (Accession No. ABJ16553) (SEQ ID NO: 23). Highlighted in black and highlighted in gray are respectively identical and similar residues in these sequences.

FIG. 9 shows alignments of the amino acid sequences of beta-caryophyllene synthase QHS1 from *Artemisia annua* (Accession No. AAL79181) (SEQ ID NO: 18), beta-caryophyllene synthase from *Mikania micrantha* (Accession No. ACN67535) (SEQ ID NO: 19), beta-caryophyllene synthase from *Cucumis sativus* (Accession No. AAU05952) (SEQ ID NO: 20), (E)-beta-farnesene synthase from *Citrus junos* (Accession No. AAK54279) (SEQ ID NO: 24), terpene synthase from *Citrus junos* (Accession No. AAG01339) (SEQ ID NO: 25), putative terpene synthase from *Citrus×paradisi* (Accession No. AAM00426) (SEQ ID NO: 26), and beta-caryophyllene/alpha-humulene synthase from *Arabidopsis thaliana* (Accession No. AAO85539) (SEQ ID NO: 21). Highlighted in black and highlighted in gray are respectively identical and similar residues in these sequences. Primers designed for amplifying beta-caryophyllene synthase genes are underlined.

FIG. 10 shows partial DNA sequence corresponding to citrus sesquiterpene synthase (SEQ ID NO:3) and primers, namely, B63R (SP3) (SEQ ID NO: 29), B62R (SP2) (SEQ ID NO: 30), B61F (SEQ ID NO: 31) and B48r (SP1) (SEQ ID NO: 32), designed for rapid amplification of its 5'- and 3'-ends employing RACE methodology.

FIG. 11 shows alignments of the nucleotide (SEQ ID NO: 27) and amino acid (SEQ ID NO: 28) sequences of farnesyl pyrophosphate synthase 1 (FPPS1) from *Arabidopsis thaliana* (Accession No. X75789). Underlined are sequences used to design primers for amplifying a full-length cDNA encoding a functional FPP synthase gene.

DETAILED DESCRIPTION OF THE INVENTION

Figure 2:
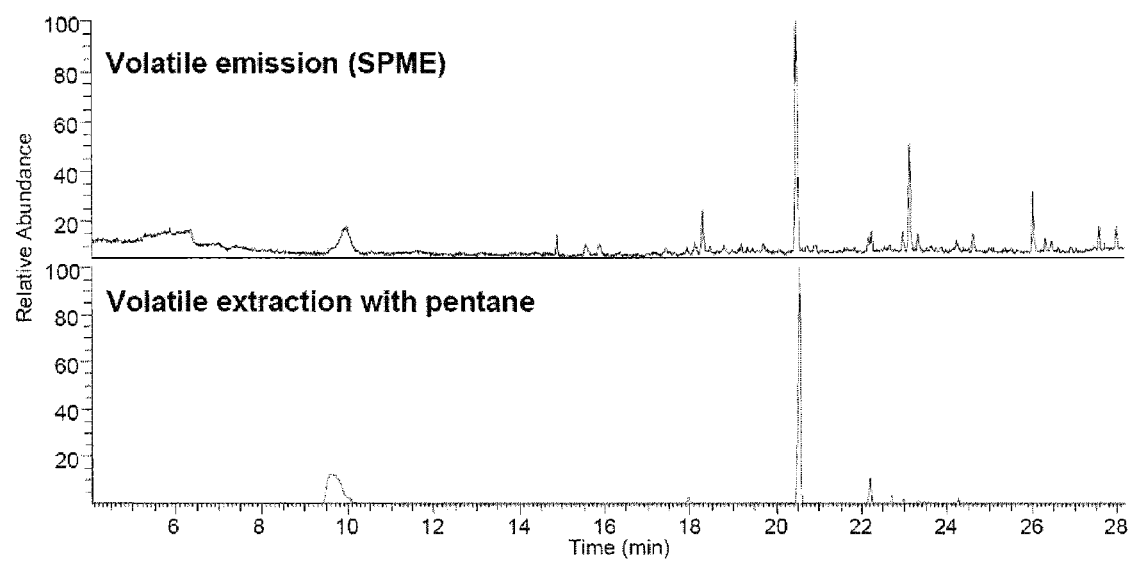
FIG. 2 shows volatile terpenes emitted (upper chromatogram) and extracted (lower chromatogram) from guava leaves.

The invention relates to methods for controlling HLB based on the observation that sesquiterpenes produced by the guava leaves repel the HLB vectors, *Diaphorina citri* and/or *Tryoza erytrae* psyllid insects.

A terpene is an unsaturated hydrocarbon based on an isoprene unit ($C_5H_8$), which may be acyclic or cyclic. A sesquiterpene is a terpene based on a $C_{1-5}$ structure.

The guava, like other aromatic plants or essential-oil-plants, accumulates large amounts of sesquiterpenes in their leaves. Typically, sesquiterpenes such as β-caryophyllene and α-copaene represents 50-60% of the total amount of volatiles emitted by guava leaves. In guava plants, the sesquiterpenes are often synthesized and accumulated in specialized anatomical structures, glandular trichomes or secretory cavities, localized on the leaves and stems surface. The sesquiterpenes accumulated in the plants can be extracted by different means such as steam distillation that produces the so-called essential oil containing the concentrated sesquiterpenes.

In certain embodiments of the invention, as a method to control HLB, at least one sesquiterpene extracted from guava plants, preferably β-caryophyllene, is applied to the citrus plants through spray or slow delivery systems. Slow delivery systems have been already used by entomologists to deliver pheromones. In such systems, pure β-caryophyllene is disposed in a PVC resin that preserves and releases the chemical compound. This resin is applied directly to citrus trees in the orchards. It has the property of releasing the compound over a period of 3-4 months.

The price and availability of the plant natural extracts are dependent on the abundance, the oil yield and the geographical origin of the plants. Because of the complexity of their structure, production of individual sesquiterpene molecules by chemical synthesis is often limited by the cost of the process and may not always be chemically or financially feasible. Therefore, a biochemical route for the production of sesquiterpene molecules would be of great interest. The engineering of a biochemical route for the production of sesquiterpene molecules requires a clear understanding of the biosynthesis of sesquiterpenes and the isolation of the genes encoding enzymes involved in specific biosynthetic steps.

The biosynthesis of sesquiterpenes in plants has been extensively studied. The common five-carbon precursor to all terpenes is isopentenyl pyrophosphate (IPP). Most of the enzymes catalyzing the steps leading to IPP have been cloned and characterized. Two distinct pathways for IPP biosynthesis coexist in the plants. The mevalonate pathway is found in the cytosol and endoplasmic reticulum and the non-mevalonate pathway (or deoxyxylulose 5-phosphate (DXP) pathway) is found in the plastids. In the next step IPP is repetitively condensed by prenyl transferases to form the acyclic prenyl pyrophosphate terpene precursors for the sesquiterpenes, farnesyl-pyrophosphate (FPP). These precursors serve as substrate for the sesquiterpene synthases, which catalyze complex multiple step cyclizations. Thus, the first committed step of β-caryophyllene biosynthesis is the cyclization of the universal sesquiterpene precursor FPP by a sesquiterpene synthase. A set of genes encoding β-caryophyllene synthases has been cloned from plants. These synthases are usually involved in the production of different sesquiterpenes. For example, a single protein encoded by a β-caryophyllene synthase gene from *Arabidopsis* is capable of converting FPP into the sesquiterpene products (−)-α-copaene, α-humulene, and (−)-(E)-β-caryophyllene (Chen et al., Biosynthesis and emission of terpenoid volatiles from *Arabidopsis* flowers, Plant Cell 15: 481-494 (2003); Tholl et al., Two sesquiterpene synthases are responsible for the complex mixture of sesquiterpenes emitted from *Arabidopsis* flowers, The Plant J. 42: 757-771 (2005)). A β-caryophyllene synthase from maize produces δ-elemene, α-humulene, and (−)-(E)-β-caryophyllene (Kollner et al. A maize (E)-β-caryophyllene synthase implicated in indirect defense responses against herbivores is not expressed in most American maize varieties, The Plant Cell 20:482-494 (2008)). β-caryophyllene synthases have been also isolated from *Artemisia annua* (Cai et al., A cDNA clone for β-caryophyllene synthase from *Artemisia annua*, Phytochem 61:523-529 (2002)), cucumber (Mercke et al., Combined transcript and metabolite analysis reveals genes involved in spider mite induced volatile formation in cucumber plants, Plant Phys. 135: 2012-2024), rice (Cheng et al., The rice (E)-β-caryophyllene synthase (OsTPS3) accounts for the major inducible volatile sesquiterpenes, Phytochem 68: 1632-1641 (2007)) and oregano (Degenhardt et al., Restoring a maize root signal that attracts insect-killing nematodes to control a major pest, PNAS 106:13213-218 (2009)).

Chimeric genes encoding sesquiterpene synthases have been used to genetically transform plants with the aim to attract/repel pollinators (Kessler et al., Field experiments with transformed plants reveal the sense of floral scents, Science 321: 1200-1202 (2008)), to attract pest-killing insects (Kappers et al., Genetic engineering of terpenoid metabolism attracts bodyguards to *Arabidopsis*, Science 309: 2070-2072 (2005); Schnee et al., The products of a single maize sesquiterpene synthase form a volatile defense signal that attracts natural enemies of maize herbivores, PNAS 103: 1129-1134 (2006)) and nematodes (Degenhardt et al., Restoring a maize root signal that attracts insect-killing nematodes to control a major pest, PNAS 106:13213-218 (2009)), and directly to kill insect pests (Wu et al., Redirection of cytosolic or plastidic isoprenoid precursors elevates terpene production in plants, Nature Biotechnology, 24: 1441-1447 (2006)), indicating that transgenic strategies addressed to increase the accumulation of such sesquiterpenes, including β-caryophyllene, could be an ecologically sound alternative, that alone or in combination with a reduced use of pesticides, would prevent damages caused by pest-transmitted devastating diseases.

One embodiment of the present invention relates to the isolation of nucleic acids encoding for sesquiterpene synthases from citrus plants, citrus-related plants belonging to the Rutaceae family, guava, guava-related plants from the Myrtaceae family, or any other living organism. As used herein, a sesquiterpene synthase is any enzyme that catalyzes the synthesis of a sesquiterpene. One can determine whether a polypeptide encoded by a nucleic acid of the invention has sesquiterpene synthase activity by the enzyme characterization assay described in the examples herein.

In an embodiment of the nucleic acid of the invention, the nucleic acid is chosen from (a) a nucleic acid comprising the nucleotide sequence substantially as set out in SEQ ID NO:1; or (b) a nucleic acid encoding the polypeptide substantially set out in SEQ ID NO:2, wherein the polypeptide encoded by said nucleic acid has sesquiterpene synthase activity.

In another embodiment of the nucleic acid of the invention, the nucleic acid is chosen from (a) a nucleic acid comprising the nucleotide sequence substantially as set out in SEQ ID NO:3; or (b) a nucleic acid encoding the polypeptide substantially set out in SEQ ID NO:4, wherein the polypeptide encoded by said nucleic acid has sesquiterpene synthase activity.

Preferably, a nucleic acid and/or polypeptide of the invention is isolated from citrus plants. In an embodiment, the nucleic acid is isolated from guava plants.

Preferably, the nucleic acid according to the invention comprises SEQ ID NO:1.

In a particular embodiment, the invention relates to certain isolated nucleotide sequences including those that are substantially free from contaminating endogenous material. The terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al., Molecular Cloning: A Laboratory Manual, 2nd ed., Cold Spring Harbor Laboratory, Cold Spring Harbor, N.Y. (1989), Current Protocols in Molecular Biology edited by F. A. Ausubel et al., John Wiley and Sons, Inc. (1987), and Innis, M. et al., eds., PCR Protocols: A Guide to Methods and Applications, Academic Press (1990).

As described herein, the nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art. In general, nucleic acid molecules within the scope of the invention include sequences that hybridize to sequences of the invention at temperatures 5° C., 10° C., 15° C., 20° C., 25° C., or 30° C. below the melting temperature of the DNA duplex of sequences of the invention, including any range of conditions subsumed within these ranges.

In another embodiment, the nucleic acids of the invention comprises a sequence substantially as set out in SEQ ID NO:1 or SEQ ID NO:3. In one embodiment, the nucleic acids are at least 70%, at least 85%, at least 90%, or at least 95% identical to nucleotides SEQ ID NO:1 or SEQ ID NO:3, and each nucleic acid encodes a protein that has sesquiterpene synthase activity, as demonstrated, for example, in the enzyme assay described in the examples, with increased stability and efficacy as compared with that of the polypeptide encoded by SEQ ID NO:1 or SEQ ID NO:3. In one embodiment, the nucleic acid comprises the nucleotide sequence SEQ ID NO:1. In another embodiment, the nucleic acid comprises the nucleotide sequence SEQ ID NO:3.

In yet another embodiment, the nucleic acid comprises a contiguous stretch of at least 50, 100, 250, 500, or 750 contiguous nucleotides of SEQ ID NO:1 or SEQ ID NO:3. Such contiguous fragments of these nucleotides may also contain at least one mutation so long as the mutant sequence retains the functionality of the original sequence and the capacity to hybridize to these nucleotides under low or high stringency conditions, such as for example, moderate or high stringency conditions. Such a fragment can be derived, for example, from nucleotide (nt) 200 to nt 1700, from nt 800 to nt 1700, from nt 1000 to nt 1700, from nt 200 to nt 1000, from nt 200 to nt 800, from nt 400 to nt 1600, or from nt 400 to nt 1000 of SEQ ID NO:1 or SEQ ID NO:3.

As described above, polypeptides encoded by the nucleic acids of the invention are encompassed by the invention. The isolated nucleic acids of the invention may be selected from a nucleic acid encoding the polypeptide substantially set out in SEQ ID NO:2 or SEQ ID NO:4. In one embodiment, the polypeptides are at least 70%, at least 85%, at least 90%, or at least 95% identical to SEQ ID NO:2 or SEQ ID NO:4, and the polypeptides have sesquiterpene synthase activity, as demonstrated, for example, in the enzyme assay described below.

Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). The present invention thus encompasses any nucleic acid derived from SEQ ID NO:1 or SEQ ID NO:3 capable of encoding a polypeptide substantially set out in SEQ ID NO:2 or SEQ ID NO:4.

Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (Gene 42:133, 1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462.

In one embodiment, the invention provides for isolated polypeptides. As used herein, the term "polypeptides" refers to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention. Antibodies are defined to be specifically binding if they bind polypeptides of the invention with a $K_a$ of greater than or equal to about $10^7 M^{-1}$, such as greater than or equal to $10^8 M^{-1}$.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the sesquiterpene synthases of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc), or an improved expression level in a desired expression system. A variant or site direct mutant may be made by any method known in the art. As stated above, the invention provides recombinant and non-recombinant, isolated and purified polypeptides, such as from guava or citrus plants. Variants and derivatives of native polypeptides can be obtained by isolating naturally-occurring variants, or the nucleotide sequence of variants, of other or same plant lines or species, or by artificially programming mutations of nucleotide sequences coding for native guava or citrus polypeptides. Alterations of the native amino acid sequence can be accomplished by any of a number of conventional methods.

Accordingly, the present invention provides a method for preparing a variant functional sesquiterpene synthase, the method comprising the steps of (a) selecting any of nucleic acids from the group consisting of SEQ ID NO: 1 or 3, (b) altering the nucleic acid sequence to obtain a population of mutant nucleic acids, and, (c) transforming host cells with the mutant nucleic acid to express polypeptides, and, (d) screening the polypeptides for a functional polypeptide having at least one modified property. The modified property may be any desired property, for example the properties mentioned above. The alteration of the selected nucleic acid may be performed by random mutagenesis, site-specific mutagenesis or DNA shuffling, for example. The alteration may be at least one point mutation, deletion or insertion. For example, polypeptides having an amino acid sequence encoded by a nucleic acid obtained from shuffling techniques, involving at least any of SEQ ID NO: 1 or 3, are also encompassed by the present invention. The steps of the method according to this embodiment of the invention, such as screening the polypeptides for a functional polypeptide, are known to the skilled person who will routinely adapt known protocols to the specific modified property that is desired.

For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion. The present invention also encompasses nucleic acids obtained from altering a nucleic acid of the present invention, for example in order to obtain a variant polypeptide.

There are several methods known in the art for the creation of transgenic plants. These include, but are not limited to: electroporation of plant protoplasts, liposome-mediated transformation, *Agrobacterium*-mediated transformation, polyethylene-glycol-mediated transformation, microinjection of plant cells, and transformation using viruses. In one embodiment, direct gene transfer by particle bombardment is utilized. In another embodiment, *Agrobacterium*-mediated transformation is utilized.

*Agrobacterium tumefaciens*-mediated transformation is the most common method used to transform citrus plants. It uses a disarmed *A. tumefaciens* strain carrying the gene(s) of interest in its genome as a vector to transform citrus cells or tissues by cocultivation for a few days.

Genetic transformation is used naturally by *Agrobacterium* species as a system to insert fragments of their DNA in infected plant cells. Expression of the genes transferred by the bacteria in plant cells leads to the elicitation of crown gall tumors in plants usually at wound sites. In *A. tumefaciens* the transferred DNA is called T-DNA and it resides in a megaplasmid called Ti (from Tumor-Inducing) plasmid.

Disarmed Ti plasmids can be engineered by removing T-DNA genes involved in tumor formation. Then, heterologous genes with the appropriate regulatory regions can be inserted into a new chimeric T-DNA region that once incorporated in *Agrobacterium* cells carrying a disarmed Ti plasmid can be used to integrate and express the foreign genes in plant cells. From transformed plant cells it is possible to regenerate whole transgenic plants by using standard tissue culture systems.

Direct gene transfer by particle bombardment provides another example for transforming plant tissue. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either $CaCl_2$ or ethanol precipitation methods which are commonly known in the art.

DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue.

The DNA used for coating the particles may comprise an expression cassette suitable for driving the expression of the gene of interest that will comprise a promoter operably linked to the gene of interest.

Methods for performing direct gene transfer by particle bombardment are disclosed in U.S. Pat. No. 5,990,387 to Tomes et al. In one embodiment, transfected DNA is integrated into a chromosome of a non-human organism such that a stable recombinant systems results. Any chromosomal integration method known in the art may be used in the practice of the invention, including but not limited to, recombinase-mediated cassette exchange (RMCE), viral site specific chromosomal insertion, adenovirus, and pronuclear injection.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes. All publications mentioned in this application are incorporated by reference to disclose and describe the methods and/or materials in connection with which the publications are cited.

Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

EXAMPLES

The following examples are intended to illustrate the preferred embodiments of the invention without limiting the scope as a result.

Material

Citrus plants used in the present examples were obtained from The Citrus Germplasm Bank (Instituto Valenciano de Investigaciones Agrarias (IVIA), Moncada, Valencia, Spain). Guava seeds were obtained from local growers from Vietnam and Brazil and were grown in a green house at the IVIA. Other available sources of Guava mature plants were Politechnical University and Botanical Garden from Valencia (Spain).

Example 1

Analysis of Leaf Volatile Content and Emission from Citrus and Guava Plants

Volatile content and emission was studied in leaves from different genotypes (*Psidium guajava, Citrus sinensis, Citrus aurantifolia* and *Citrus clementina*). Analyses were conducted using leaves at different developmental stages, collected at different hours of the day and in different seasons. Each sample was analyzed at least four times (two biological replicates plus two technical replicates).

To determine volatile content, collected leaf tissue was immediately frozen in liquid nitrogen and stored at −80° C. until extraction. Freeze ground material (200 mg) was weighted in screw-cap Pyrex tubes and immediately 3 mL of cold pentane was added. Samples were homogenized on ice for 30 s with a Yellowline homogenizer (model DI 25). The suspension was vortexed for 15 s and 3 mL of Milli-Q water were added, further vortexed for 30 s and centrifuged at 1800 g for 10 min at 4° C. The organic phase was recovered with a Pasteur pipette and the aqueous phase re-extracted two times more with 3 mL of pentane. An aliquot of 2 µL of the pooled organic phases was directly injected into the GC-MS for volatile analysis (see below).

As headspace analysis gives a more realistic picture of the volatile profile emitted by plants and detected by insects that respond to plant volatiles, static headspace sampling with a solid phase microextraction (SPME) device was performed. Leaf samples were enclosed in 50 mL screw-cap Pyrex tubes carrying a septum on the top and containing 1 mL of milli-Q water for avoiding leaf hydric stress. SPME fiber (100 µm poly(dimethyl) siloxane, Supelco, Bellefonte, Pa.) was exposed, at a controlled temperature of 22° C., between 1 and 4 hours. Immediately afterwards, fiber was transferred to GC injector (220° C.) and thermal desorption was prolonged to 4 mins.

Figure 3:
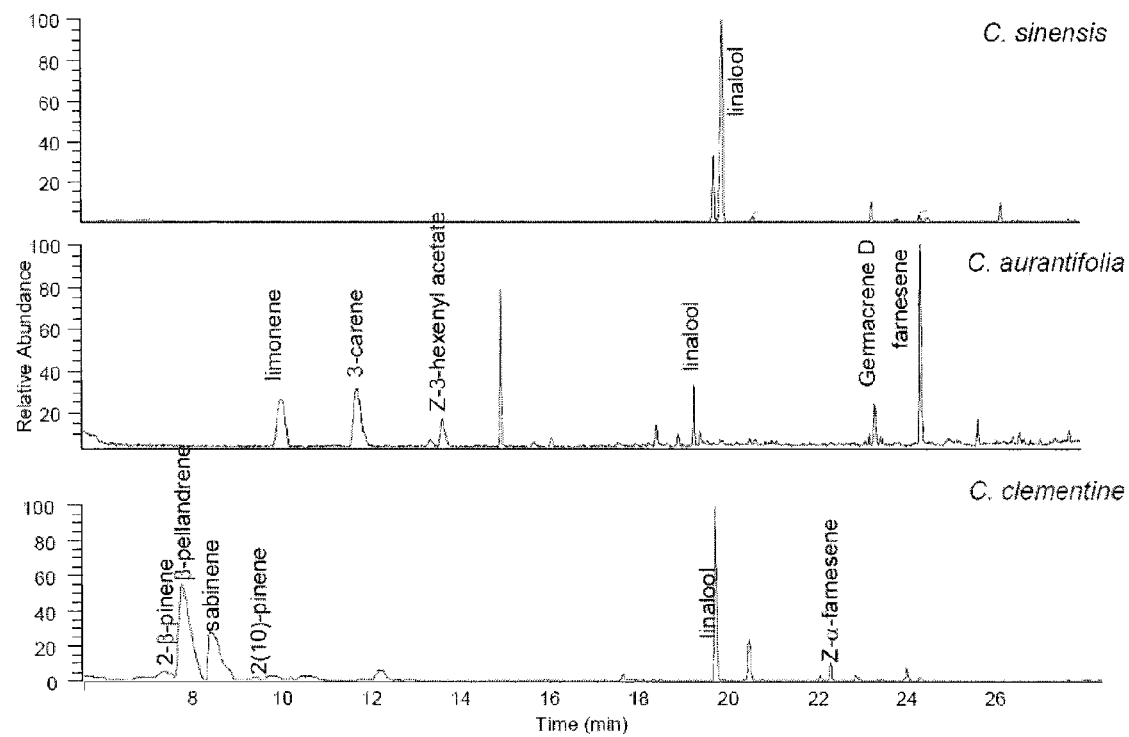
FIG. 3 shows representative gas chromatographic separation of volatiles emitted from the leaves of different citrus genotypes.
Figure 4:
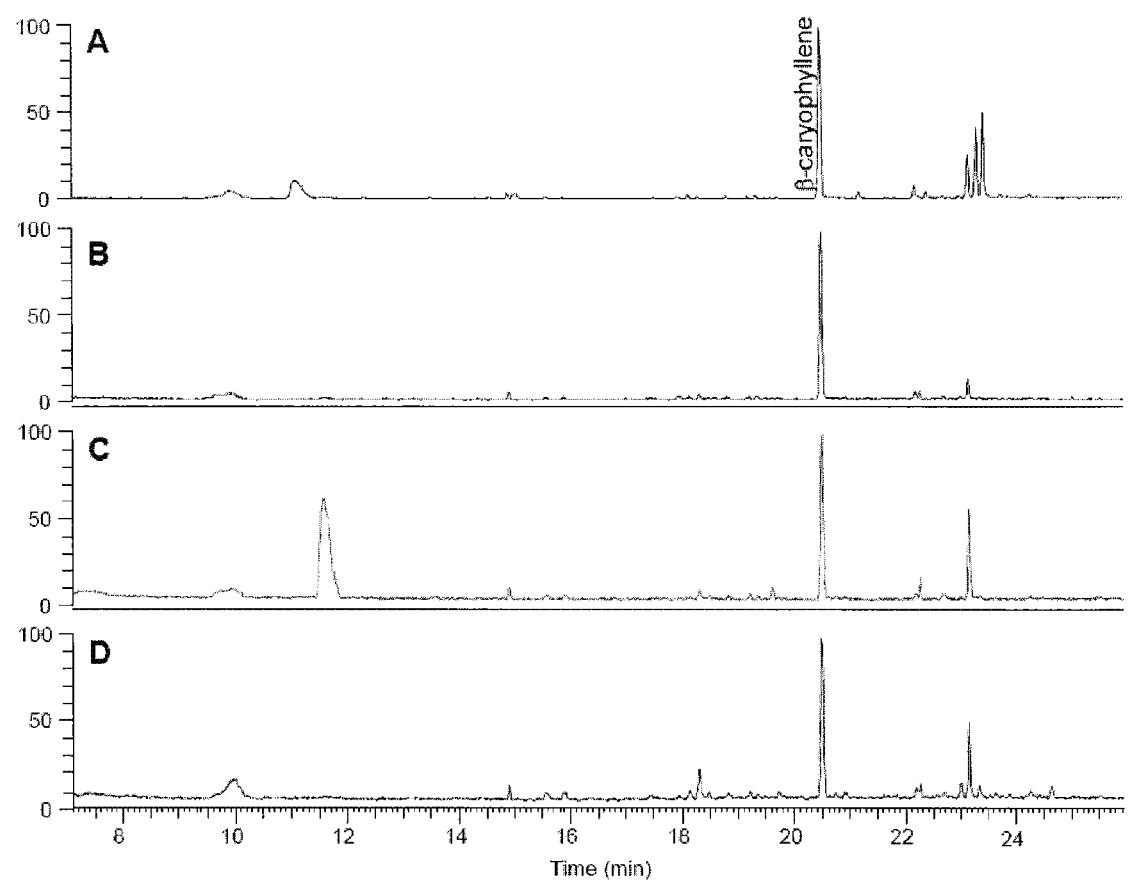
FIG. 4 shows representative gas chromatographic separation of volatiles emitted from guava leaves at different developmental stages: A, flush; B, young; C, mature; D, old.

Results showed that main compounds identified through volatile content were also the major volatiles emitted by leaves (for a representative example, see FIG. 2). As described in the literature, more than 80% of total volatiles contained and emitted by citrus leaves were monoterpenes, with linaool being the most abundant one in all the genotypes and sampling dates analysed (FIG. 3). In these samples, β-caryophyllene was not detected or detected at very low levels and not in all the replicates. In guava leaves, sesquiterpenes were the predominant volatiles and, in all the samples analysed, β-caryophyllene constituted at least 50% of total compounds (FIG. 4).

Example 2

GC-MS Analysis

A Thermo Trace GC Ultra coupled to a Thermo DSQ mass spectrometer with electron ionization mode (EI) at 70 eV was used. The ion source and the transfer line were at 200 and 260° C., respectively. Volatile compounds were separated on a HP-INNOWax (Agilent J&C Columns) column (30 m×0.25 mm i.d.×0.25 µm film). The column temperatures were programmed from 40° C. for 5 min, raised to 150° C. at 5° C. min$^{-1}$, then raised to 250° C. at 20° C. min$^{-1}$ and held 2 min at 250° C. The injector temperature was 220° C. Helium was the carrier gas at 1.5 mL min$^{-1}$ in the splitless mode. Electron impact mass spectra were recorded in the 30-400 amu range with a scanning speed of 0.5 scans$^{-1}$. Compounds were identified by matching of the acquired mass spectra with those stored in reference libraries (NIST, MAINLIB, REPLIBT) or from authentic standard compounds when available.

Example 3

Response of *D. citri* to Guava Volatiles

A series of experiments were designed in order to investigate the effect of guava leaf volatiles on *D. citri* behaviour. *D. citri* adults of mixed sex were obtained from continuously reared cultures on *C. limonia* seedlings maintained in Fundecitrus (Araraquara, Brazil) at 25±1° C., 70±10 relative humidity and a L14:D10 photoperiod.

Figure 6:
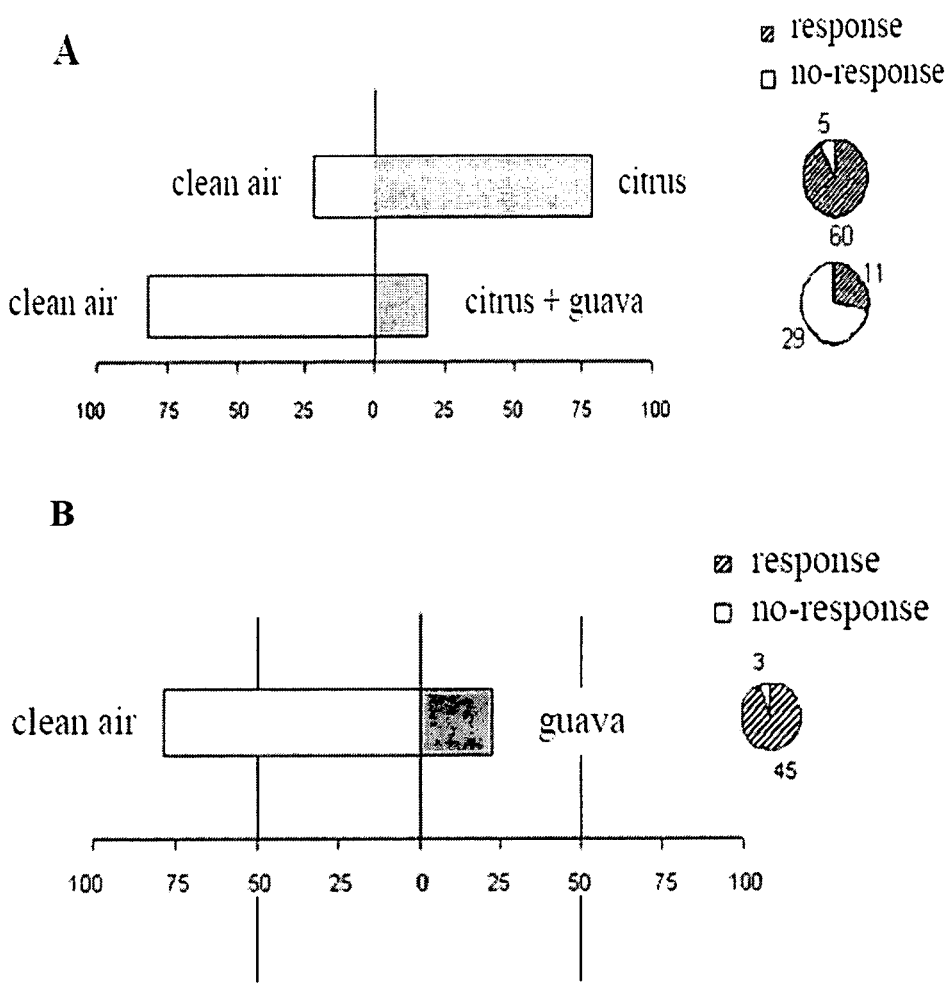
FIG. 6 shows representative percentage and number of selections of *Diaphorina citri* to citrus volatiles±guava odor (A) and to guava volatiles versus clean air (B) in two arms and four arms olfactometers, respectively.

A Y-tube olfactometer with one 12.5 cm long entrance arm and two 21.0 cm long test arms (0.6 cm inner diameter) was used for behavioural assays. Charcoal cleaned air (granulated 4-8 mm. Applichem GmbH, Darmstadt, Germany) was pumped (0.4 L min$^{-1}$) through two glass jars of 2 L containing the volatile sources, consisting of air or guava seedlings. 40 psyllids were assayed in each experiment, and each experiment was conducted at least per triplicate. Position of psyllids was determined after 10 min and those which had passed 10.0 cm after branching were recorded as 'responsive'. Results showed that guava volatiles repelled or immobilized psyllids or limited citrus attractiveness (FIG. 6(A)). Further studies were conducted employing a four-arm olfactometer. Charcoal cleaned air was humidified by passage through a glass cylinder filled with water and separated into four flows (0.4 L min$^{-1}$) each of which was directed to one of the four olfactometer fields. The air flowing into the test field of the olfactometer passed through a glass cylinder (1 L) containing the samples or clean air. 40 psyllids were assayed in each experiment, and each experiment was conducted at least per triplicate. Results from guava versus clean air clearly indicated that guava volatiles had a repellent effect (FIG. 6(B)).

Effect of pure β-caryophyllene (puriss >98.5%; Sigma-Aldrich, Germany) and α-copaene (puriss >90.0%; Sigma- Aldrich, Germany) on *D. citri* was also evaluated employing a four-arm olfactometer. In each observation, a psyllid was placed in the middle of the olfactometer permeated by air coming from each of its four stretched-out arms. In two of the arms clean air was pumped, while in the remaining arms air was pumped through glass vials containing 10 µL of pure compounds. Each observation lasted five min, and the first and final choices of every individual psyllid were recorded. At least 29 psyllids were employed for studying behavioral response to each compound. In the preliminary test with clean air, no significant differences were obtained between the arms, indicating that all of them were equivalent and did not introduce any bias during choice tests. Assays conducted with β-caryophyllene and α-copaene showed a higher level of psyllids entering the unscented arm, envisaging the repellent effect of these compounds (Table 1).

TABLE 1

Table 1: Representative results from Y-tube olfactometric assays. Percentage of individuals that chose each compound in four-arm olfactometer trials examining responses of psyllids to treatment odor sources versus a clean air control.

|   | Clean air | $\chi^2$ | p | n |
|---|---|---|---|---|
| β-caryophyllene | | | | |
| First choice | 42.3% | 57.7% | 1.23 | 0.4054 | 29(26) |
| Final choice | 32.0% | 68.0%* | 6.48 | 0.0237 | 29(25) |
| α-copaene | | | | |
| First choice | 42.0% | 58.0% | 0.76 | 0.4862 | 34(33) |
| Final choice | 33.0% | 67.0%** | 7.33 | 0.0138 | 34(33) | n: total sample size (with number of individuals that made a choice in parentheses).
Data were compared using chi-square test (*$p < 0.05$; **$p < 0.01$).

These results have been reproduced when lower doses of the pure compounds were used in olfactometric assays.

Example 4

Isolation of Total RNA

Leaves were collected from Citrus and Guava plants, immediately frozen in liquid nitrogen and grounded using a mortar and pestle. Total RNA was extracted using the Qiagen RNeasy Mini. As described by Keszei et al. (Phytochem. 71: 844-852. 2010) the extraction buffer was modified by adding 2% PVP (Sigma-Aldrich) and 120 mg/mL of sodium-isoascorbate (to saturation) (Sigma-Aldrich) to inhibit the oxidative conjugation of phenolics to the RNA. Typically, an average of 100 µg total RNA was obtained from 200 mg of grounded tissue. The concentration of RNA was estimated from the OD at 260 nm. The integrity of the RNA was evaluated on an agarose gel by verifying the integrity of the ribosomic RNA bands.

Example 5

Reverse Transcription (RT) and PCR Amplification

Synthesis of cDNAs was performed with 1 µg of total RNA. RT was carried out in the presence of 500 ng of oligo-dT and 200 units of SuperScript II Reverse transcriptase (Gibco BRL, Germany). Samples were incubated 5 min at 65° C., 50 min at 42° C. and 15 min at 70° C. For PCR amplification primers containing start and stop codons of SEQ ID NO:1 and SEQ ID NO:3 were designed (Table 2).

TABLE 2 primers employed for amplifying cDNAs corresponding to sequences SEQ ID NO: 5 (B25F) and SEQ ID NO: 6 (B26R), SEQ ID NO: 7 (B27F) and SEQ ID NO: 8 (B28R). The start and stop codons are underlined.

| | Primer | Primer sequence (5'→3') | Orientation |
|---|---|---|---|
| SEQ ID NO: 5 | B27F | CACC<u>ATG</u>TCCGCTCAAGTTC | S |
| SEQ ID NO: 6 | B28R | TCAGATGG<u>TAA</u>CAGGGTCTC | AS |
| SEQ ID NO: 7 | B27F | GC<u>ATG</u>AGGGATGTTAAGAG | S |
| SEQ ID NO: 8 | B28R | CTGTTTTCTTTGAAGAC<u>TAG</u>GC | AS |

S, Sense;
AS, Antisense.

The thermal cycler conditions were: 5 min at 95° C.; 35 cycles of 30 sec at 94° C., 30 sec at 56° C. and 150 sec at 72° C.; and finally 10 min at 72° C. The sizes of the PCR products were evaluated on a 1% agarose gel. The bands corresponding to the expected size were excised from the gel, purified using the QIAquick™ Gel Extraction Kit (Qiagen) and cloned in the pTZ57R/T (Fermentas GMBH). Inserted DNA fragments were then subject to DNA sequencing and the sequence compared against the GenBank non-redundant protein database (NCBI) using the BLASTX algorithm (Altschul, S. F., Gish, W., Miller, W., Myers, E. W., and Lipman, D. J. (1990) Basic local alignment search tool. J. Mol. Biol. 215, 403-410).

Example 6

Construction of Expression Plasmids for Sesquiterpene Synthase Activity Assay

Each expression cassette prepared comprises a transcription initiation or transcriptional control region (s) (e.g. a promoter), the coding region for the protein of interest, and a transcriptional termination region. In order to avoid possible toxicity of the sesquiterpene compound when it is accumulated in a microbial host, an inducible promoter was selected. For functional expression of the sesquiterpene synthases, the cDNAs were sub-cloned in the pF3K WG (BYDV) Flexi® Vector from Promega, designed for in vitro expression of proteins. This vector carries the lethal barnase gene, which is replaced by the DNA fragment of interest and acts as a positive selection for successful ligation of the insert, and a kanamycin resistance gene for selection of bacterial colonies. Additionally, it allows the directional cloning of PCR products in SgfI and PmeI restriction sites. In this plasmid the cDNA is placed downstream of the SP6 promoter.

Inserts were amplified by PCR using an amino-terminal PCR oligonucleotide including the start codon and SgfI site and a carboxy-terminal PCR primer including the stop codon and PmeI site (Table 3). In the forward primer six in-frame histidine codons where added in order to create a N-terminal tagged protein. The amplified cDNAs were purified, and ligated into pF3K WG (Promega) plasmid according to the manufacturer protocol. Constructs were verified by digestion and DNA sequencing.

All amplifications of cDNA for expression were performed using the Pfu DNA polymerase (Promega), in a final volume of 50 µL containing 5 µL of Pfu DNA polymerase 10× buffer, 200 µM each dNTP, 0.4 µM each forward and reverse primer, 2.9 units Pfu DNA polymerase and 5 µL of 1 µL of cDNA (prepared as described above). The thermal cycling conditions were as follows: 2 min at 95° C.; 25 cycles of 30 sec at 95° C., 30 sec at 52° C. and 4 min at 72° C.; and 10 min at 72° C. The PCR products were purified on an agarose gel and eluted using the QIAquick® Gel Extraction Kit (Qiagen).

TABLE 3 primers employed for cloning SEQ ID NO: 1 in pF3K WG Flexi Vector (Promega) corresponding to sequence SEQ ID NO: 9 (SQS5F) and SEQ ID NO: 10 (SQS5R). Restriction sites are marked in italics. Nucleotides encoding HHHHHH are bold-lettered. The start and stop codons are underlined.

| Primer | Primer sequence (5'→3') | Orientation |
|---|---|---|
| SQS5F | GCGATCGCC<u>ATG</u>CATCACCATCACCATCACGGATCCGCTCAAGTTCTAGC (SEQ ID NO: 9) | S |
| SQS5R | GTTTAAAC<u>TCA</u>GATGGTAACAGGGTCTCT (SEQ ID NO: 10) | AS |

S, Sense;
AS, Antisense.

Example 7

Sesquiterpene Synthase Expression and Enzyme Assays

In a standard protein expression experiment, the expression plasmids containing the sesquiterpene synthase cDNA as well as the empty plasmid (negative control) were transformed into XL1-Blue E. coli cells (Stratagene). Single colonies of transformed E. coli were used to inoculate 5 ml LB medium. Liquid cultures of the bacteria harboring the expression construct or the empty plasmid were grown at 37° C. to an $OD_{600}$ of 0.8. Plasmid DNA was isolated from bacteria using QIAprep spin miniprep kit (Qiagen) following manufacturer instructions. 2 µg of purified plasmid DNA were employed for in vitro transcription/translation in wheat germ extract cell free expression system from Promega (TnT® SP6 High-yield wheat germ protein expression system) in a final volume of 50 µL. Following incubation at 25° C. for 2 hours protein production was confirmed analyzing an aliquot of 1 µL by Sodium dodecyl sulfate polyacrylamide gel electrophoresis (SDS-PAGE) and western blotting following standard procedures. Nitrocellulose membranes were probed with monoclonal Anti His G HRP antibody from Invitrogen.

Figure 5:
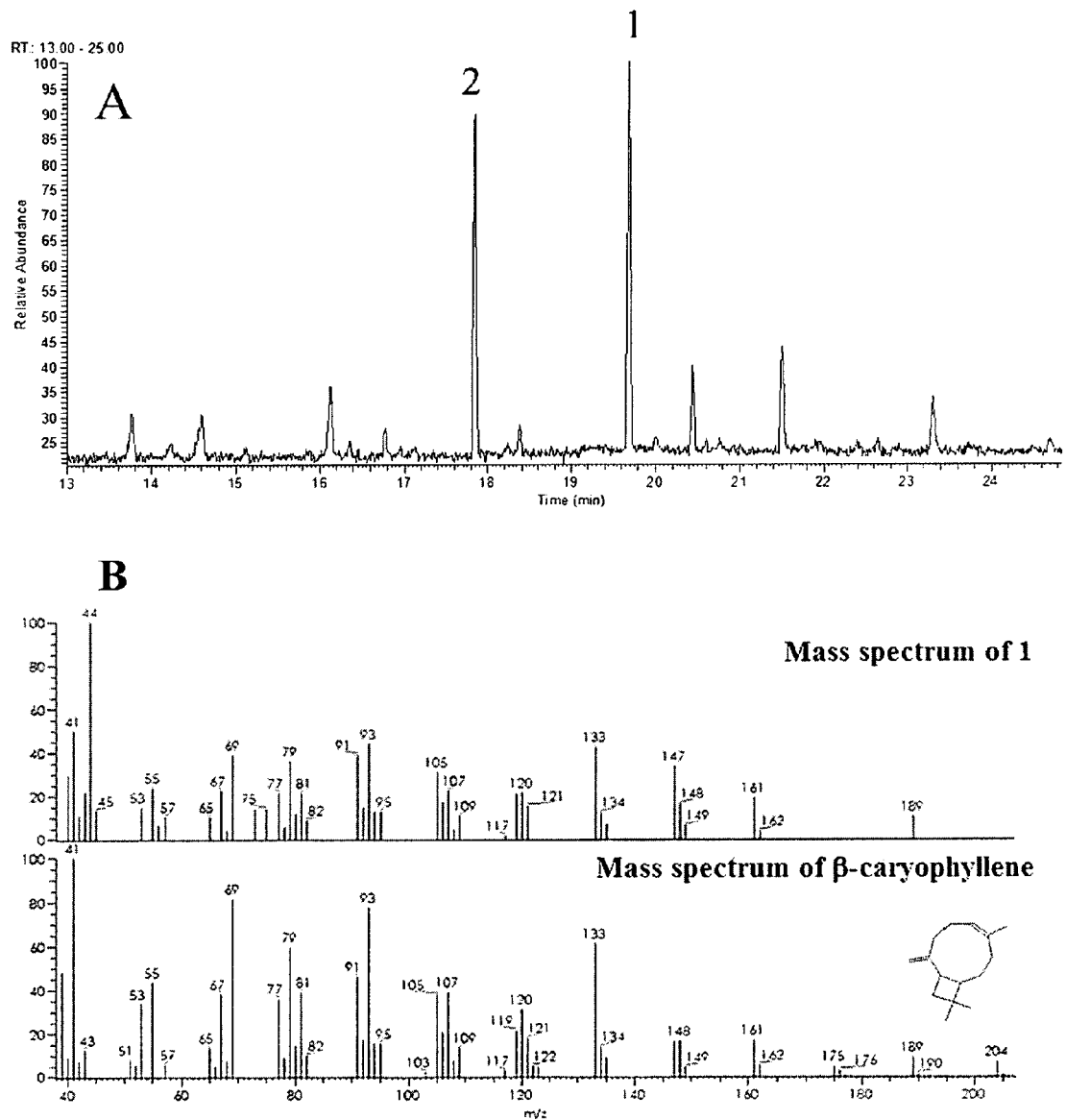
FIG. 5 shows (A) representative total ion chromatogram of sesquiterpene products of SEQ ID NO:2. Assays were conducted with crude protein extracts from in vitro expression with farnesyl diphosphate as substrate. Peak 2 corresponds to an internal standard. (B) shows a comparison of TIC fragmentation pattern of background-corrected peak 1 and spectra of β-caryophyllene obtained from libraries.

The enzymatic assays were performed in 15 mL Teflon sealed glass tubes using 49 µL of protein extract in a final volume of 1 mL reaction buffer (25 mM potassium phosphate buffer pH 6.8; 10 mM MgCl2; 1 mM MnSO4; 1 mM DTT) supplemented with 100 µM FPP (Sigma). The medium was overlaid with 1 ml pentane to trap volatile products and the tubes incubated over-night at 30° C. The pentane phase, containing the sesquiterpene, was recovered and the medium extracted with a second volume of pentane. 2 µL of the combined pentane fractions were analyzed by Gas Chromatography as described above. In this way, caryophyllene synthase activity was attributed to sequence SEQ ID NO:2 (FIG. 5).

Example 8

Figure 9:
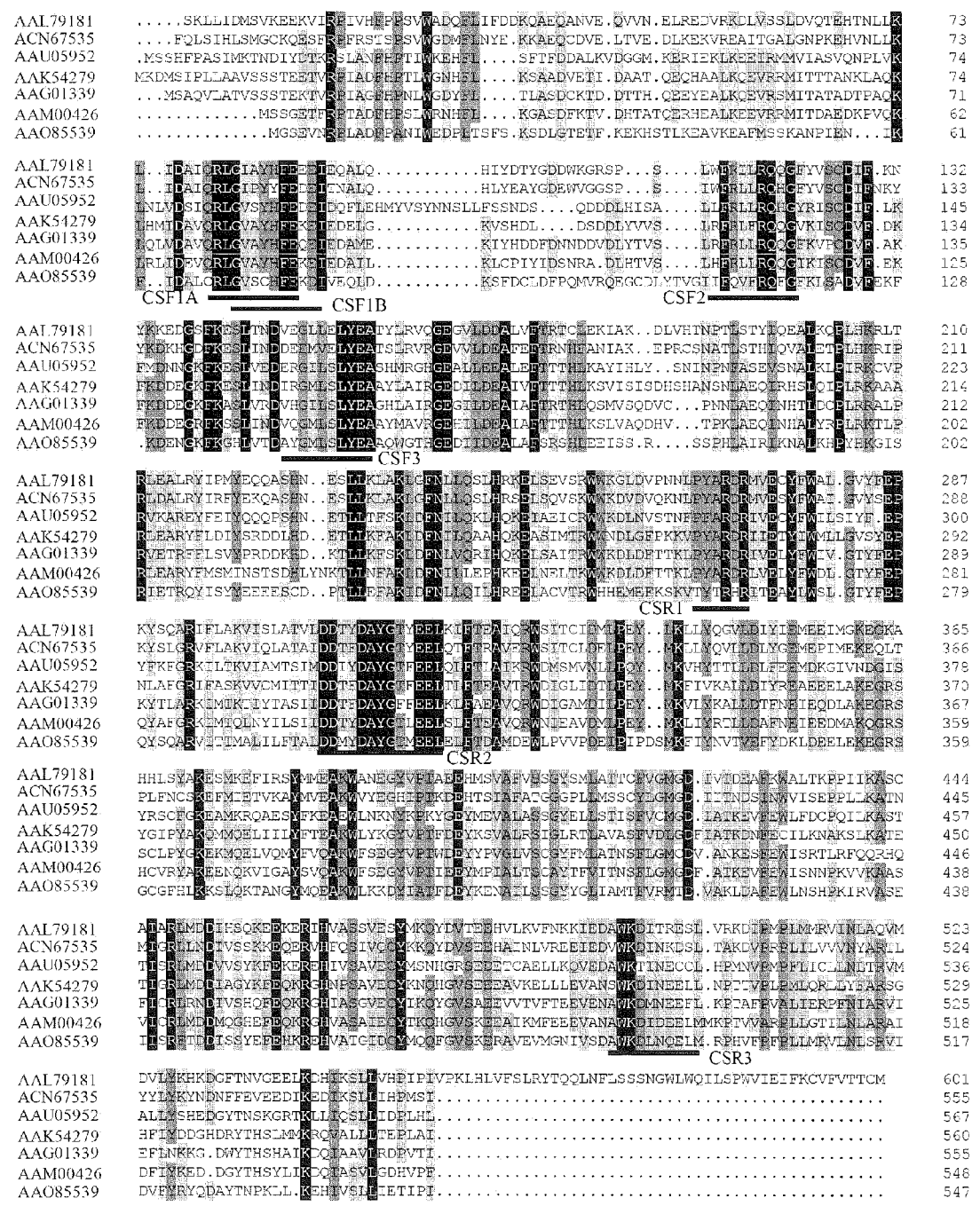

Isolating Partial Sequences Corresponding to Sesquiterpene Synthases Using RT-PCR The deduced amino-acid sequences of plant β-caryophyllene synthases were aligned to identify conserved regions and design plant β-caryophyllene synthase-specific oligonucleotides (FIG. 7). Aminoacid sequences from plant sesquiterpene synthases with demonstrated β-caryophyllene synthase activity were obtained from the NCBI database. Homology analysis showed low (around 21%) protein identity between known plant β-caryophyllene synthases. However, higher homology was found if protein sequences were separated in two groups (FIG. 8). The first group (FIG. 8A) contained the sequences of the β-caryophyllene synthases from dicotyledonous plants, as Arabidopsis (Chen et al., Biosynthesis and emission of terpenoid volatiles from Arabidopsis flowers, Plant Cell 15: 481-494 (2003); Tholl et al. Two sesquiterpene synthases are responsible for the complex mixture of sesquiterpenes emitted from Arabidopsis flowers, The Plant J. 42: 757-771 (2005)), cucumber (Mercke et al Combined transcript and metabolite analysis reveals genes involved in spider mite induced volatile formation in cucumber plants. Plant Phys. 135: 2012-2024), Mikania Micrantha (Wang et al. Cloning, expression and wounding induction of β-caryophyllene synthase gene from Mikania micrantha H.B.K. and allelopathic potential of β-caryophyllene, Alleophaty J. 24:35-44 (2009)) and Artemisia annua (Cai et al. A cDNA clone for β-caryophyllene synthase from Artemisia annua. Phytochem 61:523-529 (2002)). The second group (FIG. 8B) contained sequences of β-caryophyllene synthases from monocotyledonous plants as maize (Kollner et al. A maize (E)-β-caryophyllene synthase implicated in indirect defense responses against herbivores is not expressed in most american maize varieties, The Plant Cell 20:482-494 (2008)), and rice (Cheng et al. The rice (E)-β-caryophyllene synthase (OsTPS3) accounts for the major inducible volatile sesquiterpenes. Phytochem 68: 1632-1641 (2007). β-caryophyllene synthases from monocotyledonous presented an overall identity of 47%, M Micrantha and Artemisia annua β-caryophyllene synthases showed 58% homology, while that from Arabidopsis and cucumber showed low identity (around 17%) with the rest of amino acid sequences. In order to gain insight into citrus sesquiterpene synthases, amino acid sequences from the NCBI database were aligned with β-caryophyllene synthases from dicotyledonous plants (FIG. 9). Sequences employed for analysis were (E)-β-farnesene synthase from Citrus junos (AAK54279), putative terpene synthase from Citrus junos (AAG01339), putative terpene synthase from Citrus paradisi (AAM00426), and valencene synthase from Citrus sinensis (AAQ04608). Metal ion-binding motif (DDxxD) and $RRx_8W$ domain, both characteristic of plant sesquiterpene synthases (both mono- and dicotiledonous) were identified in all the peptidic sequences. In addition, other conserved amino acids were identified, localized mostly in the central region of the sequences. Based on these conserved regions among plants, degenerated primers from β-caryophyllene synthases and citrus sesquiterpene synthases were designed (underlined in FIG. 9) in order to isolate β-caryophyllene synthase from guava plants. Detailed sequence of these primers is provided in Table 4. The highest sequence homology was found in the central part of the sequences. Three regions containing sufficiently conserved amino acids were selected and degenerated oligonucleotides specific for these regions were designed (i.e.

four forward (CSF1A, CSF1B, CSF2, CSF3) and three reverse primers (CSR3, CSR2, CSR1) were deduced) (Table 4). Partial sequences were amplified, cloned and sequenced following standard procedures. On the basis of these sequences, new primers were designed and amplification of 5' and 3' ends was performed employing the 5'/3' RACE Kit (Roche, Mannheim, Germany) following the instructions of the manufacturer.

TABLE 4

CSF1A, CSF1B, CSF2, CSF3 and CSR1, CSR2 and CSR3 are primers designed based on conserved motifs in order to amplify partial sequences corresponding to sesquiterpene synthases. FPPF and FPPR, are primers designed for amplifying FPP synthase from Arabidopsis thaliana.

| | Primer | Primer sequence (5'→3') | Orientation |
|---|---|---|---|
| SEQ ID NO: 11 | CSF1A | TKGGKGTRKCKTATCAYTTTGA | S |
| SEQ ID NO: 12 | CSF1B | GGAGTRKCMTAYCATTTTGAA | S |
| SEQ ID NO: 13 | CSF2 | GGSATGTTAAGTTTGTAYGARGC | S |
| SEQ ID NO: 14 | CSF3 | GATGAYACWTWTGACGCKTAYGG | S |
| SEQ ID NO: 15 | CSR3 | CCRTAMGCGTCAWTWGTRTCATC | AS |
| SEQ ID NO: 16 | CSR2 | TCCTCATTCATATCTTTCCA | AS |
| SEQ ID NO: 17 | CSR1 | CTATCTCTTGCAAAAGG | AS |

S, Sense;
AS, Antisense.
K: G or T;
R: A or G;
M: C or A; W:
T or A;
Y: T or C.

Example 9

Isolation of Full-Length Sequences Corresponding to Sesquiterpene Synthase Genes. 3'- and 5'-RACE Synthesis of first-strand cDNAs from leaf tissues and PCR amplifications were performed as described above. Combinations of sense and antisense primers detailed in Table 3 were used for PCR. PCR products were ligated into pTZ57R/T (Fermentas GMBH) and sequenced. Sequence information allowed rapid amplification of cDNA ends by RACE-PCR strategy, using the 5'/3' RACE Kit (Roche, Mannheim, Germany) according to the manufacturer instructions.

For example, CSF1B and CSR1 amplified a band of 621 bp with high homology to sesquiterpene synthase genes from NCBI database. On basis of this sequence, new specific primers were designed for 5'-end (B62R and B63R) and 3'-end (B61F) amplification (FIG. 10). For 5'-end amplification, first strand cDNA was synthesized using the specific primer CSR1 (Table 4). A homopolymeric A-tail was added to the 3' end of purified cDNA and then it was PCR amplified using the gene specific primer B62R and specific oligo-dT anchor primer. A band of about 800 bp was amplified, gel-purified QIAquick Gel Extraction Kit (Qiagen) and further amplified by a second PCR using the nested gene specific primer B63R and the PCR anchor primer. The amplification product (700 bp) was purified from agarose gel, ligated into pTZ57R/T (Fermentas GMBH) and sequenced. For 3'-end amplification, cDNA was synthesized using oligo dT-anchor primer, and PCR amplification was performed with PCR anchor primer and the gene specific primer B61F. The amplification product (900 bp) was purified from agarose gel, ligated into pTZ57R/T (Fermentas GMBH) and sequenced.

Obtained sequences were first compared against the GenBank non-redundant protein database (NCBI) using the BLASTX algorithm (Altschul, S. F., Gish, W., Miller, W., Myers, E. W., and Lipman, D. J. (1990) Basic local alignment search tool. J. Mol. Biol. 215, 403-410) and then compared against the initial DNA sequence to ensure that significant DNA sequence overlap was obtained.

Example 10

Cloning of FPPS and Transit Peptides

With the aim of further increasing sesquiterpene content and emission in transgenic citrus plants, a FPP synthase gene cassette was introduced in binary plasmids for plant transformation (see below). A similar strategy was adopted by Wu et al. (Redirection of cytosolic or plastidic isoprenoid precursors elevates terpene production in plants. Nature Biotech 24: 1441-1447(2006)) who employed transgenic co-expression of FPP synthase and amorphadiene synthase in plastids for successful, high-level synthesis of amorphadiene in transgenic tobacco (*Nicotiana tabacum*) plants. To date, no FPP synthase has been isolated from citrus fruits, although one nucleotide sequence from CFGP (Citrus Functional Genomic Project) database, namely acL9351contig1, presents high identity (78%; 87% homology) with a FPP synthase from *Arabidopsis* (Acc. No. X75789). In order to select a FPP synthase gene, a search in public NCBI database was performed. FPP synthase protein is highly conserved among dicotyledonous plants. For example, FPP synthase proteins from such unrelated species as *Arabidopsis* (Acc. No. Q09152), *Malus domestica* (Acc. No. AAM08927), *Vitis vinifera* (Acc. No. AAX76910), *Gossypum hirsutum* (Acc. No. CAA72793) and *Hevea brasilensis* (Acc. No. AAM98379) showed an overall identity of 79% (89% homology). Identity of FPP synthase proteins from mono and dicotyledonous plants is also high. For example, FPPS from *Zea mays* (Acc. No. AC634051) is 71% identical (85% similar) to that of *Arabidopsis*. Finally, the high degree of similarity between FPPS from plants and FPPS from other kingdoms, i.e. *Saccharomyces cerevisae* FPPS (Acc. No. EDN63217) is 66% homologous to that of *Arabidopsis*, suggest a good conservation of this protein along evolution. Thus, any FPPS from a dicotyledonous plant was though to be suitable for increasing FPP production in citrus plants. As that from *Arabidopsis* had been well characterized and its activity demonstrated (Cunillera et al. *Arabidopsis thaliana* contains two differentially expressed farnesyl diphosphate synthase genes. J. Biol. Chem 221: 7774-7780 (1996)), primers were designed based on AtFPS1 sequence (Acc. No. X75789) in order to amplify a full length cDNA encoding a functional FPP synthase (FIG. 11). Total RNA was extracted from *Arabidosis thaliana* (ecotype Columbia) leaves using the Qiagen RNeasy Mini Kit following the manufacturer instructions and cDNA was synthesized as described above. Amplification of cDNA was performed employing Pfu DNA polymerase (Promega) and the same reaction mix as described above. The thermal cycling conditions were: 2 min at 95° C., 30 cycles of 30 sec and 95° C., 30 sec at 50° C. and 1.5 min at 72° C., and 10 min at 72° C. PCR product was purified from agarose gel with the QIAquick®-Gel extraction Kit (Qiagen), ligated into pTZ57R/T (Fermentas GMBH) and its identity confirmed by sequencing.

Besides this, shifting sesquiterpene biosynthesis from cytosol to plastids or mitochondria can improve results of metabolic engineering. First, this can avoid possible detrimental effects of sesquiterpene accumulation in cytosol and, second, avoiding competition for cytosolic pool of FFP by introduced sesquiterpene synthase and endogenous FPP-utilizing enzymes can provide a substantial substrate pool for this engineered pathway without compromising plant growth. This strategy has been successfully employed before by Wu et al. (Redirection of cytosolic or plastidic isoprenoid precursors elevates terpene production in plants. Nature Biotech 24: 1441-1447(2006)) who performed transgenic co-expression of FFP synthase and amorphadiene synthase in plastids for successful, high-level synthesis of amorphadiene in transgenic tobacco (*Nicotiana tabacum*) plants. Switching the subcellular localization of the introduced sesquiterpene synthase to the mitochondrion has been also previously employed by Kappers et al. (Genetic engineering of terpenoid metabolism attracts bodyguards to *Arabidopsis*. Science 309: 2070-2072 (2005)), who reported that FPP is readily available in this organele for sesquiterpene biosynthesis.

The transit peptide (TP) of the small sub-unit of Rubisco (SSU) from *Pissum sativum* (Acc. No. X00806) was synthesised as three overlapping oligonucleotide fragments and subsequently PCR-amplified introducing NdeI and ClaI restriction sites in its 5'- and 3'-ends, respectively. The PCR product was ligated in pTZ57R/T (Fermentas GMBH) generating pTZ-TPssu plasmid and sequenced. The CoxIV sequence (from *Saccahromyces cerevisae*, Acc. No. X01048) was synthesized as two complementary oligonucleotide fragments and subsequently PCR-amplified introducing NdeI and ClaI restriction sites in its 5'- and 3'-ends, respectively. The PCR product was ligated in pTZ57R/T (Fermentas GMBH) generating pTZ-mtTP plasmid and sequenced.

Example 11

Expression Vector Construction

For generating the expression vectors, plasmids pMOG 180 (Mogen International, ampicillin resistance) and pROK binary vector (kanamycin resistance, Invitrogen), both carrying the constitutive CaMV 35S promoter and Nopaline synthase (NOS) terminator sequences were employed. The T-DNA from pROK also carried the Neomycin Phosphotransferase II (NPTII) gene under the control of the NOS promoter and terminator sequences.

Cloned sesquiterpene synthases and FPPS1 were PCR-amplified from pTZ57R/T (Fermentas GMBH) adding convenient restriction sites for ligation of transit peptides (NdeI, ClaI) and in pMOG vector (BamHI), ligated again in pTZ57R/T (Fermentas GMBH) and sequenced, generating plasmids pTZ-CsCS+rest, pTZ-PgCS+rest, pTZ-CsCoS+rest, pTZ-PgCoS+rest and pTZ-FPPS+rest. All these plasmids and those carrying transit peptides (pTZ-TPssu and pTZ-mtTP, see example above) were 10-fold over digested with NdeI and ClaI restriction enzymes from Takara (Shuzo, Co. Ltd). Digested fragments of adecuate size were excised from agarose gel and purified using QIAquick®-Gel extraction Kit (Qiagen) following manufacturer instructions. After plasmids dephosphorilation with Antartic Phosphatase (New England Biolabs), ligation of fragments corresponding to both transit peptides was performed with T4-Ligase (Invitrogen), according to the manufacturer instructions. Correct orientation and maintenance of ORFs from inserts was checked by sequencing and digestion. The resulting plasmids harboring TPssu for plastid import were denominated as pTZ-TPssu-CsCS, pTZ-TPssu-PgCS, pTZ-TPssu-CsCoS, pTZ-TPssu-PgCoS and pTZ-TPssu-FPPS, while those with mitochondrial import signal were named pTZ-mtTP-CsCS, pTZ-mtTP-PgCS, pTZ-mtTP-CsCoS, pTZ-mtTP-PgCoS and pTZ-mtTP-FPPS. Plasmids with FPPS, harboring or not transit peptide, were 10-fold over digested with BamHI and ligated between CaMV 35S promoter and Nopaline synthase (NOS) terminator of pMOG 180 vector. Resulting plasmids were named pMOG-FPPS, pMOG-TPssu-FPPS and pMOG-mtTP-FPPS. Correct orientation and maintenance of ORFs from inserts was checked by sequencing and digestion. Cassettes from these three plasmids were PCR amplified with specific primers for CaMV 35S promoter and NOS terminator containing AseI restriction sites for subcloning purposes. PCR products were over-digested with AseI and ligated in pROK vector, generating pROK-FPPS, pROK-TPssu-FPPS and pROK-mtTP-FPPS vectors. ORFs from sesquiterpene synthase genes were amplified from pTZ-CsCS, pTZ-TPssu-CsCS, pTZ-mtTPCsCS, pTZ-CsCoS, pTZ-TPssu-CsCoS, pTZ-mtTP-CsCoS, pTZ-PgCS, pTZ-TPssu-PgCS, pTZ-mtTP-PgCS, pTZ-PgCoS, pTZ-TPssu-PgCoS and pTZ-mtTP-PgCoS with specific primers for pTZ57R/T plasmid containing XbaI restriction site.

Amplified products were gel-purified, over digested with XbaI (New England Biolabs) and ligated into expression vectors pROK, pROK-FPPS, pROK-TPssu-FPPS and pROK-mtTP-FPPS. Correct orientation and maintenance of ORFs from inserts was checked by sequencing and digestion. Resulting plasmids expressing sesquiterpene synthase peptides directed to cytosol were named pROK-CsCs, pROK-CsCoS, pROK-PgCS, pROK-PgCoS. Resulting plasmids expressing FPPS plus a sesquiterpene synthase peptide, both directed to cytosol, were named pROK-FPPS-CsCs, pROK-FPPS-CsCoS, pROK-FPPS-PgCS, pROK-FPPS-PgCoS. Plasmids expressing sesquiterpene synthase peptides directed to chloroplast were named pROK-TPssu-CsCs, pROK-TPssu-CsCoS, pROK-TPssu-PgCS, pROK-TPssu-PgCoS, while those expressing sesquiterpene synthase peptides directed to mitochondrion were named pROK-mtTP-CsCs, pROK-mtTP-CsCoS, pROK-mtTP-PgCS, pROK-mtTP-PgCoS. Resulting plasmids expressing FPPS plus a sesquiterpene synthase peptide, both directed to chloroplast, were named pROK-TPssu-FPPS-TPssu-CsCs, pROK-TPssu-FPPS-TPssu-CsCoS, pROK-TPssu-FPPS-TPssu-PgCS, pROK-TPssu-FPPS-TPssu-PgCoS. Resulting plasmids expressing FPPS plus a sesquiterpene synthase peptide, both directed to mitochondrion, were named pROK-mtTP-FPPS-mtTP-CsCs, pROK-mtTP-FPPS-mtTP-CsCoS, pROK-mtTP-FPPS-mtTP-PgCS, pROK-mtTP-FPPS-mtTP-PgCoS.

Each construct was incorporated by electroporation into *A. tumefaciens* competent cells. NPTII was used as selectable marker gene as its expression provided to plant cells resistance to aminoglycoside antibiotics, as kanamycin, neomycin, geneticin, and others.

Example 12

Transformation of Citrus Plants with a Sesquiterpene Synthase Gene from Guava or Citrus The sweet orange (*Citrus sinensis* L. Osb.) varieties Valencia and Pera were transformed with a β-caryophyllene synthase gene or a α-copaene syntase gene from sweet orange or from *Psidium guajava*, under the control of the constitutive CaMV 35S promoter and Nopaline synthase (NOS) terminator.

The strain EHA 105 of *A. tumefaciens* was used in this example for transformation of mature citrus explants. Bacteria were cultured overnight in an orbital shaker at 28° C. and 200 rpm in Luria Broth (LB) medium containing the proper antibiotics to grow the binary systems. Bacterial cells were pelleted at 3500 rpm for 10 min, resuspended and diluted to $4 \times 10^7$ or $4 \times 10^8$ cells/ml in liquid inoculation medium, which consisted of MS salt solution, 0.2 mg/L thiamine hydrochloride, 1 mg/L pyridoxine hydrochloride, 1 mg/L nicotinic acid, and 3% (w/v) sucrose, pH 5.7.

For the transformation of sweet orange mature tissues, buds were collected from trees maintained in a greenhouse and were grafted onto seedlings of a vigorous rootstock under glasshouse conditions (18-27° C.), and newly elongated shoots were used as starting material. Stem pieces (20 cm in length) were stripped of their leaves and thorns disinfected for 10 min in a 2% (v/v) sodium hypochlorite solution and rinsed three times with sterile distilled water. Internodal stem segments (about 1 cm long) were cut transversely and incubated for 15 min in 10-cm-diameter plates containing 15 ml of the bacterial suspension in inoculation medium by gentle shaking. The infected explants were blotted dry on sterile filter paper and placed horizontally on plates with the cocultivation medium for a 3-day co-cultivation period. Inoculation medium consisted of 4.3 g/L MS salts, 10 mL/L vitamin stock solution, 30 g/L sucrose, pH 5.7. 10. Co-cultivation medium consisted of inoculation medium plus 2 mg/L 2,4-D, 2 mg/L IAA, 1 mg/L 2, i-P, 8 g/L agar, pH 5.7.

After co-cultivation, the explants were blotted dry with sterile filter paper and transferred to shoot regeneration medium (SRM), which consisted of MS salts, 0.2 mg/L thiamine hydrochloride, 1 mg/L pyridoxine hydrochloride, 1 mg/L nicotinic acid, 3% (w/v) sucrose, 1% (w/v) agar, pH 5.7, plus 100 mg/L kanamycin for the selection of transgenic shoots, and 250 mg/L vancomycin and 500 mg/L cefotaxime to control bacterial growth. This medium was supplemented with 3 mg/L BAP. Cultures were maintained in the dark for 4 weeks at 26° C. and then were transferred to 16-h photoperiod, 45 μEm-2 s-1 illumination, and 26° C.

Shoots regenerating from explants cultured in the kanamycin-containing selection medium were excised from the explants and cut in two pieces. The basal portion was PCR-assayed and, if the reaction was positive for the gene of interest, the apical part was grafted in vitro onto a nontransgenic decapitated in vitro-grown seedling. About 3-4 weeks after shoot-tip grafting, plantlets were again grafted on a vigorous seedling rootstock in a greenhouse at 18 to 27° C.

Methods for transforming mature citrus tissues are disclosed in U.S. Pat. No. 6,103,955 to Peña et al. The transformation resulted in plants that produced high amounts of β-caryophyllene or α-copaene, constitutively. Three independently transformed lines were selected, based on that trait. Behavioral bioassays in olfactometers revealed that transgenic citrus plants did not attract but repelled citrus psyllids.

Example 13

Production of β-caryophyllene and α-copaene and its Use to Repel *Diaphorina citri* in the Field Through a Slow-delivery System β-caryophyllene is a widespread compound in the vegetable kingdom, i.e. it is present in many oleoresins of the majority of conifers of the *Pinaceae* family. However, this sesquiterpene is typically produced in low abundance in the host organism. The oil of the clove tree Eugenia caryophyllata (*Syzygium aromaticum*) contains β-caryophyllene in considerable amount and serves as a preparative source for the isolation of this compound. α-copaene is found as a minor component in the essential oils of leaves from various plant species, such as guava, while is abundant in roots and seeds of copaiba (*Copaifera officinalis* (Jacq) L.) and angelica (*Angelica archangelica* L.) (Jacobson et al. Optical isomers of α-copaene derived from several plant sources. J. Agric. Food Chem 35 (5): 798-800 (1987)).

Nowadays, despite using modern techniques, isolation of these sesquiterpenes from plant sources suffers from low yields and high consumption of natural resources (i.e. Quispe-Condori et al. Obtaining β-caryophyllene from *Cordia verbenacea* de Candolle by supercritical fluid extraction. J. of Supercritical Fluids 46:27-32 (2008), Jacobson et al. Optical isomers of α-copaene derived from several plant sources. J. Agric. Food Chem 35 (5): 798-800 (1987)). Furthermore, β-caryophyllene and α-copaene concentration in plants depends on factors difficult to control, such as weather conditions and plant diseases. On the other hand, although chemical synthesis of β-caryophyllene had been accomplished decades ago (Corey et al. Total synthesis of d,l-caryophyllene and d,l-iscaryophyllene. J. Am. Chem. Soc. 86:485-492 (1964)) it is still difficult to scale for industrial production.

Thus, this invention also provides methods for biosynthesis and metabolic engineering of β-caryophyllene and α-copaene with the goal of developing cost effective methods for stable production at large scale and with consistent quality.

An attractive alternative strategy is to engineer metabolic pathways for production of β-caryophyllene in a diverse host. Even a cell, which cannot synthesize sesquiterpenes, contains farnesyl pyrophosphate if it synthesizes steroids or terpenes. Since every cell contains at least either steroids or terpenes, theoretically almost all hosts are capable of synthesizing sesquiterpenes using the DNA sequences of the present invention as far as a suitable host-vector system is available. Host-vector systems are known, for example, for plants such as *Nicotiana tabacura, Petunia hybrida* and the like, microorganisms such as bacteria, for example *Escherichia coli, Zymornonas mobilis* and the like, yeasts, for example *Saccharomyces cerevisiae* and the like, and fungus (i.e. ascomycetes and basidiomycetes species).

Engineering of β-caryophyllene production in a heterologous host may require availability of its precursor (FPP) in sufficient amount in order to avoid competition for FPP pool by exogenous and endogenous FPP-utilizing enzymes that could result in detrimental effects. To that end different approaches would be efficient: (i) switching enzyme cellular compartmentation from cytosol to mitochondria or plastid employing known peptide transit signals (i.e. Kappers et al. Genetic engineering of terpenoid metabolism attracts bodyguards to *Arabidopsis*. Science 309: 2070-2072 (2005)), (ii) co-expressing β-caryophyllene synthase and FPP synthase genes (i.e. Wu et al. Redirection of cytosolic or plastidic isoprenoid precursors elevates terpene production in plants. Nature Biotechnology 24: 1441-1447 (2006)), (iii) engineering the host with a heterologous MVA/MEP pathway (i.e. Yu et al. Molecular cloning and functional characterization of α-humulene synthase, a possible key enzyme of zerumbone biosynthesis in shampoo ginger (*Zingiber zerumbet* Smith). Planta 227:1291-1299 (2008)), (iv) increasing expression of HMGR, a putative rate-limiting step in the MVA pathway, (v) optimizing the flux through the MEP pathway, i.e. upregulation of DXR in transgenic peppermint plants resulted in a 50% increase of essential oil yield (Mahmoud and Croteau. Metabolic engineering of essential oil yield and composition in mint by altering expression of deoxyxylulose phosphate reductoisomerase and menthofuran synthase. Proc. Natl. Acad. Sci. U.S.A 98: 8915-8920 (2001)). Combinations of these approaches, i.e., coexpression of β-caryophyllene synthase and FPP synthase genes while diverting subcellular compartment of both enzymes could also be employed. In addition, optimization of the β-caryophyllene synthase gene to reflect host codon usage bias may increase β-caryophyllene production in some organisms.

In order to express the DNA sequences of the present invention in a host, it is necessary to insert the genes into a vector to introduce it into the host. Any of various known vectors can be used, such as pBIN19, pC2200, pROK or the like for plant cells (Nicotiana tabacura, Petunia hybrida); pUC19, pET101 or the like for E. coli; and YEp13 or the like for yeast.

Furthermore, it is necessary to transcribe the DNA sequences of the present invention into mRNA in the host. For this purpose, a variety of promoters such as CaMV35S, NOS, TR1', TR2' (for plants); lac, $Tc^r$, CAT, trp (for E. coli); $Tc^r$, CAT (for Zymomonas mobilis); ADH1, GAL7, PGK, TRP1 (for yeast) and the like can be used in the present invention. In the case of prokaryotic hosts, it is necessary to place a ribosome-binding site (SD sequence in E. coli) several nucleotides-upstream from the initiation codon (ATG).

The transformation of the host with the vector thus obtained can be conducted by any appropriate method, which is conventionally used in the fields of genetic manipulation or cell biology. Appropriate publications or reviews can be referenced; for example, for the transformation of microorganisms, T. Maniatis, E. F. Fritsch and J. Sambrook: "Molecular Cloning A Laboratory Manual", Cold Spring Harbor Laboratory (1982).

Culturing conditions of the transformants are essentially the same as those commonly used for the nontransformed host. Yielding of the microbial cultures could be improved if β-caryophyllene is removed from bioreactors, i.e. using ion exchange resins or pervaporation, thus avoiding possible inhibitory effects on growing. β-caryophyllene can be recovered by different methods well known for those skilled in the art, for example, pervaporation of microbial cultures or leaves distillation.

Pure β-caryophyllene is disposed in a PVC resin that preserves and releases the chemical compound. This resin is applied directly to citrus trees in the orchards. It has the property of releasing the compound over a period of 3-4 months. PVC-resin dispensers for release rate studies are prepared by mixing 40% by weight vinyl chloride/vinyl acetate emulsion copolymer (Vinnol E5/65C, Wacker Chemicals Ltd., UK) with a 1:1 mixture of the plasticizers Cereclor (S45, ICI Ltd., UK) and di-(2-ethylhexyl)-phthalate (DEHP, Sigma Aldrich Ltd., UK). The chemical compounds of interest are include with antioxidant and UV screener Waxoline Black (WB, ICI Ltd., UK) that are added to the prepolymer as required, typically 1% each by weight. The prepolymer are mixed and degassed on a rotary evaporator for 1 h under vacuum, poured into a mould composed of two glass plates with suitable spacers (0.1 cm) and cured by heating to 150° C. for 15 min. The resulting PVC sheets are removed from the moulds and cut into 1 cm squares.

The embodiments and examples illustrated and discussed in this specification are intended only to teach those skilled in the art the best way known to the inventors to make and use the invention. The above-described embodiments of the invention may be modified or varied, without departing from the invention, as easily appreciated by those skilled in the art in light of the above teachings. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method for controlling Huanglongbing (HLB) in citrus plants comprising expressing at least one gene encoding a polypeptide, wherein the polypeptide has β-caryophyllene synthase or α-copaene synthase activity in citrus plants to produce an increased amount of β-caryophyllene, α-copaene, or combinations thereof which amount is sufficient to repel *Diaphorina citri* and/or *Tryoza erytrae* psyllid insects so as to control HLB.

2. The method of claim 1, wherein the expression of the at least one gene is driven by a constitutive promoter and terminator regions.

3. The method of claim 1, wherein the expression of the at least one gene is driven by a heterologous regulator region providing strong constitutive, tissue-specific or inducible expression.

4. The method of claim 3, wherein the heterologous regulator region provides strong expression in the cytosol, chloroplasts or mitochondria.

5. The method of claim 1, which further comprises expressing a gene encoding a polypeptide, wherein the polypeptide has farnesyl pyrophophase synthase activity in citrus plants, to enhance the accumulation of the increased amount of β-caryophyllene, α-copaene, or combinations thereof produced by the polypeptides having β-caryophyllene or α-copaene synthase activity.

6. A method for controlling Huanglongbing (HLB) disease of citrus plants comprising applying an amount of purified β-caryophyllene, α-copaene, or combinations thereof to citrus plants which amount is sufficient to repel *Diaphorina citri* and/or *Tryoza erytrae* psyllid insects, so as to control the HLB disease of citrus plants.

7. The method of claim 6, wherein the purified β-caryophyllene, α-copaene, or combinations thereof is purified from an organism selected from the group consisting of plants, genetically modified plants, genetically modified bacteria, and genetically modified yeasts; wherein the genetically modified plants, the genetically modified bacteria, and the genetically modified yeasts are able to overproduce β-caryophyllene, α-copaene, or combinations thereof.

8. The method of claim 7, wherein the purified β-caryophyllene, α-copaene, or combinations thereof is purified from a guava plant.

9. The method of claim 8, wherein the purified β-caryophyllene, α-copaene, or combinations thereof is purified from leaf, fruit or stem extracts of the guava plant.

10. The method of claim 6, wherein the purified β-caryophyllene, α-copaene, or combinations thereof is applied to the citrus plants through slow delivery systems.

\* \* \* \* \*

UNITED STATES PATENT AND TRADEMARK OFFICE
CERTIFICATE OF CORRECTION

PATENT NO. : 9,572,349 B2  Page 1 of 1
APPLICATION NO. : 14/733376
DATED : February 21, 2017
INVENTOR(S) : Alquezar García et al.

It is certified that error appears in the above-identified patent and that said Letters Patent is hereby corrected as shown below:

In the Claims

Column 68:
Line 57 (Claim 5, Line 3), delete "pyrophophase" and insert -- pyrophosphase --.

Signed and Sealed this
Eleventh Day of April, 2017

Michelle K. Lee
*Director of the United States Patent and Trademark Office*